US006946560B2

(12) United States Patent
Buchwald et al.

(10) Patent No.: US 6,946,560 B2
(45) Date of Patent: *Sep. 20, 2005

(54) LIGANDS FOR METALS AND IMPROVED METAL-CATALYZED PROCESSES BASED THEREON

(75) Inventors: Stephen L. Buchwald, Newton, MA (US); David W. Old, Somerville, MA (US); John P. Wolfe, Brighton, MA (US); Michael Palucki, Belle Meade, NJ (US); Ken Kamikawa, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/420,950

(22) Filed: Apr. 22, 2003

(65) Prior Publication Data

US 2004/0010149 A1 Jan. 15, 2004

Related U.S. Application Data

(60) Division of application No. 10/004,101, filed on Oct. 23, 2001, which is a continuation of application No. 09/231,315, filed on Jan. 13, 1999, now Pat. No. 6,307,087, which is a continuation-in-part of application No. 09/113,478, filed on Jul. 10, 1998, now Pat. No. 6,395,916.

(51) Int. Cl.$^7$ ............... C07D 211/70; C07D 207/04; C07F 15/00; C07C 209/00
(52) U.S. Cl. ............... 546/339; 548/577; 556/13; 556/136; 564/405
(58) Field of Search ............... 546/339; 548/577; 556/13, 136; 564/405

(56) References Cited

U.S. PATENT DOCUMENTS

| | | | |
|---|---|---|---|
| 4,383,112 A | 5/1983 | Laidler et al. | |
| 4,604,474 A | 8/1986 | Kumobayashi et al. | 556/7 |
| 4,691,037 A | 9/1987 | Yoshikawa et al. | 556/18 |
| 4,723,033 A | 2/1988 | Erickson | |
| 4,739,084 A | 4/1988 | Takaya et al. | 556/21 |
| 4,739,085 A | 4/1988 | Takaya et al. | 556/21 |
| 4,877,908 A | 10/1989 | Petit et al. | |
| 4,885,376 A | 12/1989 | Verkade | |
| 4,954,644 A | 9/1990 | Sayo et al. | 556/14 |
| 4,992,519 A | 2/1991 | Mukherjee | 568/315 |
| 4,994,590 A | 2/1991 | Takaya et al. | 556/21 |
| 5,008,457 A | 4/1991 | Burk | |
| 5,012,002 A | 4/1991 | Kumobayashi et al. | 568/17 |
| 5,099,077 A | 3/1992 | Petit et al. | |
| 5,144,050 A | 9/1992 | Chan et al. | 556/20 |
| 5,162,586 A | 11/1992 | Villacorta et al. | |
| 5,177,230 A | 1/1993 | Burk | |
| 5,187,135 A | 2/1993 | Kolich et al. | |
| 5,187,136 A | 2/1993 | Klobucar et al. | |
| 5,187,281 A | 2/1993 | Kolich et al. | |
| 5,206,399 A | 4/1993 | Sayo et al. | 556/20 |
| 5,210,202 A | 5/1993 | Petit et al. | |
| 5,223,632 A | 6/1993 | Ishizaki et al. | 556/21 |
| 5,231,202 A | 7/1993 | Hayashi et al. | 556/21 |
| 5,268,492 A | 12/1993 | Yamamoto et al. | |
| 5,274,146 A | 12/1993 | Ishizaki et al. | 556/14 |
| 5,312,939 A | 5/1994 | Hori et al. | 556/14 |
| 5,322,956 A | 6/1994 | Burk | |
| 5,334,791 A | 8/1994 | Cavell et al. | |
| 5,347,045 A | 9/1994 | Herrmann et al. | 562/35 |
| 5,440,062 A | 8/1995 | Villacorta et al. | |
| 5,481,045 A | 1/1996 | Herrmann et al. | 568/454 |
| 5,508,458 A | 4/1996 | Zhao | |
| 5,510,503 A | 4/1996 | Laue et al. | 556/21 |
| 5,510,554 A | 4/1996 | Regnat et al. | 585/466 |
| 5,530,150 A | 6/1996 | Takaya et al. | |
| 5,565,398 A | 10/1996 | Herrmann et al. | 502/166 |
| 5,631,393 A | 5/1997 | Kohlpaintner et al. | 556/17 |
| 5,648,548 A | 7/1997 | Takaya et al. | 568/17 |
| 5,663,426 A | 9/1997 | Albanese et al. | 562/35 |
| 5,693,868 A | 12/1997 | Sayo et al. | 568/8 |
| 5,710,337 A | 1/1998 | Unruh et al. | 568/16 |
| 5,710,338 A | 1/1998 | Unruh et al. | 568/16 |
| 5,736,480 A | 4/1998 | Davis et al. | 502/155 |
| 5,739,396 A | 4/1998 | Trost et al. | |
| 5,756,760 A | 5/1998 | Miyano et al. | 548/413 |
| 5,756,838 A | 5/1998 | Davis et al. | |
| 5,767,276 A | 6/1998 | Zhang | |
| 5,777,087 A | 7/1998 | Kohlpaintner et al. | |
| 5,780,692 A | 7/1998 | Sakaguchi et al. | 568/814 |
| 5,789,333 A | 8/1998 | Angelici et al. | |

(Continued)

FOREIGN PATENT DOCUMENTS

EP 0 118 257 A1 9/1984
EP 0 135 392 A2 3/1985

(Continued)

OTHER PUBLICATIONS

Database CAPLUS on STN Chemical Abstracts (Columbus, Ohio USA) Fabbri et al., CA:121:108962 "Binaphthyl–substituted chiral phosphines and oxides from binaphthophospholes and nucleophiles" abs of Synethetic Comm., 1994, vol. 24, No. 9, pp. 1271–1278.

(Continued)

Primary Examiner—Johann Richter
Assistant Examiner—Ebenezer Sackey
(74) Attorney, Agent, or Firm—Dana M. Gordon; Foley Hoag LLP

(57) ABSTRACT

One aspect of the present invention relates to novel ligands for transition metals. A second aspect of the present invention relates to the use of catalysts comprising these ligands in transition metal-catalyzed carbon-heteroatom and carbon-carbon bond-forming reactions. The subject methods provide improvements in many features of the transition metal-catalyzed reactions, including the range of suitable substrates, reaction conditions, and efficiency.

19 Claims, 1 Drawing Sheet

U.S. PATENT DOCUMENTS

| | | | |
|---|---|---|---|
| 5,789,609 A | 8/1998 | Tamao et al. | 556/18 |
| 5,789,624 A | 8/1998 | Unruh et al. | 568/454 |
| 5,808,162 A | 9/1998 | Sayo et al. | 568/10 |
| 5,817,877 A | 10/1998 | Hartwig et al. | 564/399 |
| 5,824,830 A | 10/1998 | Ikariya | 585/269 |
| 5,827,794 A | 10/1998 | Davis et al. | 502/162 |
| 5,847,222 A | 12/1998 | Yokozawa et al. | 568/16 |
| 5,977,361 A | 11/1999 | Hartwig et al. | 544/264 |
| 6,100,398 A | 8/2000 | Hartwig et al. | 544/264 |
| 6,143,834 A | 11/2000 | Tamao et al. | 525/326.2 |
| 6,274,745 B1 | 8/2001 | Inanaga et al. | 549/416 |
| 6,307,087 B1 * | 10/2001 | Buchwald et al. | 558/388 |
| 6,395,916 B1 | 5/2002 | Buchwald et al. | 556/413 |

FOREIGN PATENT DOCUMENTS

| | | |
|---|---|---|
| EP | 0 156 607 A2 | 10/1985 |
| EP | 0 156 607 B1 | 10/1985 |
| EP | 0 174 057 A2 | 3/1986 |
| EP | 0 174 057 B1 | 3/1986 |
| EP | 0 118 257 B1 | 12/1986 |
| EP | 0 235 450 A1 | 9/1987 |
| EP | 0 135 392 B1 | 2/1988 |
| EP | 0 466 405 B1 | 1/1992 |
| EP | 0 466 405 A1 | 1/1992 |
| EP | 0 503 884 A1 | 9/1992 |
| EP | 0 667 350 A1 | 8/1995 |
| EP | 0 731 105 | 9/1996 |
| EP | 0 529 908 B1 | 5/1997 |
| EP | 0 802 173 A1 | 10/1997 |
| EP | 0 826 694 A1 | 3/1998 |
| EP | 0 849 274 A1 | 6/1998 |
| EP | 0 647 648 B1 | 3/1999 |
| JP | 51132190 A | 11/1976 |
| JP | 5-97880 | 4/1993 |
| JP | 5-239076 | 9/1993 |
| JP | 0 733 0786 | 12/1995 |
| JP | 8311090 | 11/1996 |
| JP | 0 923 528 9 | 9/1997 |
| WO | WO 89/10916 | 11/1989 |
| WO | WO 92/09552 | 6/1992 |
| WO | WO 95/22405 | 8/1995 |
| WO | WO 97/13763 | 4/1997 |
| WO | WO 97/24351 | 7/1997 |
| WO | WO 97/47633 | 12/1997 |
| WO | WO 98/12202 | 3/1998 |
| WO | WO 98/15515 | 4/1998 |

OTHER PUBLICATIONS

Database CAPLUS on STN Chemical Abstract (Columbus, Ohio USA), Old et al., CA 133:43406 "Efficient Palladium-–Catalyzed N–Arylation of Indoles" abse of Organic Letters. 200, vol. 2, No. 10, pp. 1403–1406.

Database CAPLUS on STN Chemical Abstracts (Columbus, Ohio USA) Tomori et al. CA:133:266921 "An Improved Synthesis of Functionalized Biphneyl–Based Phosphine Ligands" abs of Journal or Organic Chemistry. 2000, vol. 65, No. 17, pp. 5334–5341.

Database CAPLUS on STN Chemical Abstracts (Columbus, Ohio USA), Van Der Winkel et al., CA:114:229033 "Investigations of highly crowded phosphino lambda 3, lambda 5–diphosphaphenanthrene" abs of Heteroatom Chemistry. 1991, vol. 2, No. 1, pp. 17–28.

Database CAPLUS on STN Chemical Abstracts (Columbus, Ohio USA), Huang et al., CA:139:117168 Expanding Pd–Catalyed Bond Forming Processes: The First Amidation of Aryl Sulfonates, Aqueous Amination and Complementary with Cu–Catalyzed Reactions, abs of J. Amer. Chem. Soc. 2003, vol. 125, No. 22, pp. 6653–6655.

International Search Report, PCT/US03/38945 mailed on Oct. 12, 2004.

Vyskočil, ŠtěÅn, Synthesis of 2–Amino–2'–diphenylphosphino–1,1'–binaphthyl (MAP) and its Accelerating Effect on the Pd(O)–Catalyzed N–Arylation, Tetrahedron Letters 39 (1998): 9289–9292.

European Search Report EP 03 00 9560 prepared on Jul. 4, 2003.

Ahman, J., et al., "Asymmetric Arylation of Ketone Enolates," J. Am. Chem. Soc., 120, pp. 1918–1919, 1998.

Benincori, T., et al., "(Diphenylphosphino)–biheteroaryls: the First Example of a New Class of Chiral Atropisomeric Chelating Diphosphine Ligands for Transition Metal Catalysed Stereoselective Reactions," J. Chem. Soc., Chem. Commun., pp. 685–686, 1995.

Fiaud, J., et al., "Preparation of Optically Pure 1,2,5–Triphenylphospholane. Use as Ligand for Enantioselective Transition–Metal Catalysis," Tetrahedron Letters, vol. 32, No. 38, pp. 5089–5092, 1991.

Frejd, T., et al., "2,2'–Dimethyl–6,6'–bis(diphenylphosphino)biphenyl (BIPHEMP) as a Chiral Ligand for Transition Metal Catalyzed Asymmetric Synthesis of Binaphthyls and for Asymmetric Hydrogenation. A Comparison with BINAP," Acta Chemica Scandinavica 43, pp. 670–675, 1989.

Hiroi, K., et al., "Asymmetric Induction Reactions. VI. [1,2] Asymmetric Synthesis of a Cyclopentene Derivative by Transition Metal–Catalyzed Asymmetric Vinylcyclopropane–Cyclopentene Rearrangements with Chiral Phosphine Ligands," Chem. Pharm. Bull., 42(3) pp. 470–474 (1994).

Shirakawa, E., et al, "Carbostannylation of Alkynes Catalyzed by an Iminiphosphine—Palladium Complex," J. Am. Chem. Soc., 120, pp. 2975–2976, 1998.

Sodeoka, M., et al., Stable Diaqua Palladium (II) Complexes of BINAP and Tol–BINAP as Highly Efficient Catalysts for Asymmetric Aldol Reactions, SYNLETT, pp. 463–466, May 1997.

Sodeoka, M., et al., "Asymmetric Synthesis Using Palladium Catalysts," Pure & Appl. Chem., vol. 70, No. 2, pp. 411–414, 1998.

Tamao, K., et al., "Optically Active 2,2'–bis(Diphenylphosphinomethyl)–1,1'–Binaphthyl: A New Chiral Bidentate Phosphine Ligand for Transition–Metal Complex Catalyzed Asymmetric Reactions," Tetrahedron Letters, No. 16, pp. 1389–1392, 1977.

Tanner, D., et al., "$C_2$–Symmetric Bis(Aziridines): A New Class of Chiral Ligands for Transition Metal–Mediated Asymmetric Synthesis," Tetrahedron Letters, vol. 35, No. 26, pp. 4631–4634, 1994.

Tokunoh, R., et al., "Synthesis and Crystal Structure of a New $C_2$–Symmetric Chiral Bis–sulfoxide Ligand and Its Palladium (II) Complex," Tetrahedron Letters, vol. 36, No. 44, pp. 8035–8038, 1995.

Trost, B., et al., "Asymmetric Ligands for Transition–Metal–Catalyzed Reactions: 2–Diphenylphosphinobenzoyl Derivatives of $C_2$–Symmetric Diols and Diamines," Angew. Chem. Int. Ed. Engl. 31 No. 2, 1992.

Trost, B., et al., "Synthesis of 2,2'-Bis(diphenylphosphino)-1,1'-binaphthyl (BINAP), an Atropisomeric Chiral Bis(triaryl)phosphine, and Its Use in the Rhodium(I)-Catalyzed Asymmetric Hydrogenation of α-(Acylamino) acrylic Acids," J. Am. Chem. Soc., 102, pp. 1932–1934, 1980.

Vyskocil, S., et al., "Derivatives of 2–Amino–2'diphenylphosphino–1,1'–binaphthyl (MAP) and their Application in Pd(0)–Catalyzed Allylic Substitution," Am. Chem. Soc., Newsletter and Abstracts, 216th ACS National Meeting, Boston, MA Aug. 23–27, 1998, #538.

Wolfe, J., et al., "An Improved Catalyst System for Aromatic Carbon–Nitrogen Bond Formation: The Possible Involvement of Bis(Phosphine) Palladium Complexes as Key Intermediates," J. Am. Chem. Soc., 118, pp. 7215–7216, 1996.

Bei, X. et al., "A Convenient Palladium/Ligand Catalyst for Suzuki Cross–Coupling Reactions of Arylbornonic Acids and Aryl Chlorides", Tetrahedron Letters, 40:3855–3858 (1999).

Bei, X. et al., "General and Efficient Palladium–Catalyzed Aminations of Aryl Chlorides", Tetrahedron Letters, 40:1237–1240 (1999).

Bei, X. et al., "Phenyl Backbone–Derived P,O– and P,N–Ligands for Palladium/Ligand–Catalyzed Aminations of Aryl Bromides, Iodides, and Chlorides. Synthesis and Structures of $(P,O)_n$–Palladium(II)Aryl(Br) Complexes", Organometallics, 18:1840–1853 (1999).

Beller, M. et al., "First Palladium–Catalyzed Aminations of Aryl Chlorides", Tetrahedron Letters, 38:2073–2074 (1997).

Beller, M., "Palladacycles as Efficient Catalysts for Aryl Coupling Reactions", Agnew. Chem. Int. Ed. Engl., 34:1848 1849 (1995).

Brenner, E. et al., "New Efficient Nickel(0) Catalysed Amination of Aryl Chlorides", Tetrahedron Letters, 39:5359–5362 (1998).

Burnagin, N. et al., "Ligandless Palladium catalyzed Reactions of Arylboronic Acids and Sodium Tetraphenylborate with Aryl Halides in Aqueous Media", Tetrahedron, 53:14437–14450 (1997).

Cho, S. Y. et al, "The assymetric synthesis of cyclopentane derivatives by palladium–catalyzed coupling of prochiral alkylboron compounds", Tetrahedron:Assymetry, 9:3751–3754 (1998).

Cornils, B., "Industrial Aqueous Biphasic Catalysis: Status and Directions", Org. Proc. Res. Dev., 2:121–127 (1998).

Firooznia, F. et al., "Synthesis of 4–Substituted Phenylalanines by Cross–Coupling Reactions: Extension of the Methodology to Aryl Chlorides", Tetrahedron Letters, 39:3985–3988 (1998).

Galland, J.–C. et al., "Cross–Coupling of Chloroarenes with Boronic Acids using a Water–Soluble Nickle Catalyst", Tetrahedron Letters, 40:2323–2326 (1999).

Hamann, B. et al., "Sterically Hindered Chelating Alkyl Phosphines Provide Large Rate Accelerations in Palladium–Catalyzed Amination of Aryl Iodides, Bromides, and Chlorides, and the First Amination of Aryl Tosylates", J. Am. Chem. Soc, 120:7369–7370 (1998).

Herrmann, W. et al., "Chelating N–heterocycle carbene ligands in palladium–catalyzed heck–type reactions", J. Organometallic Chem., 557:93–96 (1998).

Indolese, A., "Suzuki–Type Coupling of Chloroarenes with Arylboronic Acids Catalysed by Nickel Complexes", Tetrahedron Lettters, 38:3512–3516 (1997).

Kawatsura, M. et al., "Simple, Highly Active Palladium Catalysts for Ketone and Malonate Arylation: Dissecting the Importance of Chelation and Steric Hindrance", J. Am. Chem. Soc., 121–1473–1478 (1999).

Littke, A. et al., "A Convenient and General Method for Pd–Cata;yzed Suzuki Cross–Couplings of Aryl Chlorides and Arylboronic Acids", Agnew. Chem Int. Ed., 37:3387–3388 (1998).

Mann, G. et al, "Palladium–Catalyzed C–N($sp^2$) Bond Formation: N–Arylation of Aromatic and Unsaturated Nitrogen and the Reductive Elimination Chemistry of Palladium Azolyl and Methyleneamido Complexes", J. Am. Chem. Soc. 120:827–828 (1998).

Mann, G. et al., "Palladium–Catalyzed C–O Coupling Involving Unactivated Aryl Halides. Sterically Induced Reductive Elimination To Form the C–O Bond in Diaryl Ethers", J. Am. Chem. Soc., 121–3224–3225 (1999).

Mitchell, M. B. et al., "Coupling of Heteroaryl Chlorides tieh Arylboronic Acids in the Presence of [1,4–Bis–(Diphenylphosphine)Butane]Palladium(II) Dichloride", Tetrahedron Letters, 20:273–2276 (1991).

Muratake, H. et al., "Intramolecular Cyclization Using Palladium–Catalyzed Arylation toward Formyl and Nitro Groups", Tetrahedron Letters, 40:2355–2358 (1999).

Muratake, H. et al., "Palladium–Catalyzed Intramolecular α–Arylation of Aliphatic Ketones", Tetrahedron Letters, 38:7581–7582 (1997).

Nishiyama, M. et al., "Synthesis of N–Arylpiperazines from Aryl Halides and Piperazine under a Palladium Tri–tert–butylphosphine Catalyst", Tetrahedron Letters, 39:617–620 (1998).

Reddy, N. P. et al., "Palladium–Catalyzed Amination of Aryl Chlorides", Tetrahedron Letters, 27:4807–4810 (1997).

Reirmeier, T. et al., "Palladium–catalyzed C–C– and C–N–coupling reactions of Aryl Chlorides", Topics in Catalysis, 4:301–309 (1997).

Saito, S. et al., "Synthesis of Biaryls via a Nickle(0)–Catalyzed Cross Coupling Reaction of Chloroarenes with Arylboronic Acids", J. Org. Chem., 62:8024–8030 (1997).

Shen, W., "Palladium Catalyzed Coupling of Aryl Chlorides with Arylboronic Acids", Tetrahedron Letters, 38:5575–5578 (1997).

Thompson, W. et al., "An Efficient Synthesis of Arylpyrazines and Bipyridines", J. Org. Chem., 53:2052–2055 (1988).

Uemura, M. et al., "Catalytic asymmetric induction of planar chirality: Palladium–catalyzed asymmetric cross–coupling of meso tricarconyl(arene)chromium complexes with alkenyl– and arylboronic acids", J. Organometallic Chem., 473:129–137 (1994).

Wang, D. et al., "New polymerization catalyzed by palladium complexes: synthesis of poly(p–phenylenevinylene) derivatives", Chem. Commun., 529–530 (1999).

Yamamoto, T. et al., "Palladium–Catalyzed Synthesis of Triarylamines from Aryl Halides and Diarylamines", Tetrahedron Letters, 39:2367–2370 (1998).

Aranyos et al., "Novel Electron–Rich Bulky Phosphine Ligands Facilitate the Palladium–Catalyzed Preparation of Diaryl Ethers", J. AM. Chem. Soc. 121: 4369–4378 (1999).

Bronco, S. and Consiglio, G., "Regio– and Stereoregular Copolymerisation of Propene with Carbon Monoxide Catalysed by Palladium Complexes Containing Atropisomeric Diphosphine Ligands", Macromol. Chem. Phys. 197: 355–365 (1996).

Chemical Abstracts vol. 123; No. 15, Oct. 9, 1995, Abstract No. 197945; Colombus, Ohio, US.

Chemical Abstracts vol. 124 No. 25, Jun. 17, 1996; Abstract No. 343650, Columbus Ohio, US.

Chemical Abstracts vol. 127 No. 21; Nov. 24, 1997, Abstract No. 293410, Colombus Ohio.

Cho, Y. S. and Shibasaki, M.; "Synthesis and Evaluation of a New Chiral Ligand: 2–diphenylarsino–2' –diphenylphosphino–1,1'—binaphthyl (BINAPAS)", Tetrahedron Letters 39 : 1773–1776 (1998).

Crameri et al., "Practical Synthesis of (S)–2–(4–fluorophenyl)–3–methylbutanoic acid, key building block for the calcium antagonist Mibefradil", Tetrahedron : Asymmetry 8 (21): 3617–3623 (1997).

Ding, K. et al., "Highly Efficient and Practical Optical Resolution of 2–Amino–2'–hydroxy–1,1'–binaphthyl by Molecular Complexation with N–Benzylcinchonidium Chloride: A Direct Transformation to Binaphthyl Amino Phosphine ", Chem. Eur. J. 5 (6): 1734–1737 (1999).

Empsall, D. H. et al., "Complexes of Platinum and Paladium with Tertiary Dimethoxyphenyl–Phosphines: Attempts to Effect O– or C–Metallation", Journal of the Chemical Society Dalton Transactions No. 3 : 257–262 (1978).

Gill, F. D. et al., "Transition Metal–Carbon Bonds. Part XXXIII. [1] Internal Metallations of Secondary and Tertiary Carbon Atoms by Platinum(II) and Palladium (III).", Journal of the Chemical Society , Dalton Transactions No. 3: 270–278 (1973).

Gladiali, S. et al., "Synthesis, Crystal Structure, Dynamic Behavior and Reactivity of Dinaphthol (2,1–b:1',2'–diphospholes and Related Atropisomeric Phosphacyclic Derivatives", J. Org. Chem. 59 (21): 6363–6371 (Oct. 21, 1994).

Gladiali, S. et al., "Novel Heterobidentate Ligands for Asymmetric Catalysis: Synthesis and Rhodium–catalysed Reactions of S–Alkyl (R)–2– Diphenylphosphino–1, 1'–binaphthyl–2'–thiol ", Tetrahedron: Asymmetry 5 (7): 1143–1146 (1994).

Hayashi Tami " Asymmetric Hydrosilylation of Olefins Catalyzed by MOP–Palladi Complexes", Acta Chem. Scand. 50 (3): 259–266 (1996).

Hattori, T. et al., " Nucleophilic Aromatic Substitution Reactions of 1–Methoxy–2–(diphenylphosphinyl)naphthalene with C–, N–, and O–Nucleophiles Facile Synthesis of Diphenyl(1– substituted –2–naphthyl)Phosphines", Synthesis, No. 2 : 199–202 (Feb. 1994).

Herrmann, A. et al., "Palladacycles: Efficient New Catalysts for the Heck Vinylation of Aryl Halides", Chemistry, A European Journal, 3 (8) :1357–1364 (Aug. 1997).

Langer et al., "Catalytic Asymmetric Hydrosilylation of Ketones Using Rhodium–( I)–Complexes of Chiral Phosphinooxazoline Ligands ", Tetrahedron : Asymmetry 7(6): 1599–1602 (1996).

Jones et al., "O– and C– Metallation of 2–Alkoxyphenylphosphines by Platinum (II)", Journal of the Chemical Society, Dalton Transactions, No. 9 : 992–999 (1974).

Old, W. et al., " A Highly Active Catalyst for Palladium–Catalyzod Cross–Coupling Reactions: Room–Temperature Suzuki Couplings and Amination of Unactivated Aryl Chlorides", J. Am. Chem. Soc. 120: 9722–9723 (1998).

Palucki et al., "Synthesis of Oxygen Heterocycles via a Palladium Catalyzed C–O Bond–Forming Reaction", J. Am. Chem. Soc. 118: 10333–10334 (1996).

Palucki et al., " Palladium–Catalyzed Intermolecular Carbon–Oxygen Bond Formation: A New Synthesis of Aryl Ethers", J. Am. Chem. Soc. 119 : 3395–3396 (1997).

Vyskocil et al., " Derivatives of 2–Amino–2'–dephenylphosphino–1,1' –binaphthyl (MAP) and Their Application in Asymmetric Palladium(0)– Catalyzed Allylic Substitution", J. Org. Chem. 63 (22) : 7738–7748 (1998).

Wolfe, P. J. and Buchwald, L. S. " A Highly Active Catalyst for the Room–Temperature Amination and Suzuki Coupling of Aryl Chlorides", Angewandte Chemie. International Edition 38 (16) : 2413–2416 (1999).

Wolfe, P. J. et al. "Highly Active Palladium Catalysts for Suzuki Coupling Reactions", J. Am. Chem. Soc. 121(41):9550–9561 (Oct. 20, 1999).

International Search Report.

Driver M. S. and Hartwig F. J. A Second Generation Catalyst for Aryl Halide Animation : Mixed Secondary Amines From Aryl Halides and Primary Amines Catalyzed by (DPPF) $PdCl_2$), J. Am. Chem. Soc. 118 : 7217–7218 (1996).

Guram S. A. et al.; "A Simple Catalytic Method for the Conversion of Aryl Bromides to Arylamines ", Angew. Chem. Int. Ed. Engl. 34 : 1348–1350 (1995).

Kang, et al, " Catalytic Asymmmetric Allylic Alkylation With a Novel P.S. Bidentale Ligand ", Bull. Korean Chem. Soc. 16(5): 439–443 (1995).

Louie, J. and Hartwig F. J. "Palladium– Catalyzed Synthesis of Arylamines from Aryl Halides. Mechanistic Studies Lead to Coupling in the Absence of Tin Reagents ", Tetrahedron Letters 36(21): 3609–3611 (1995).

Mann, G. and Hartwig, F. J. Palladium Alkoxides : Potential Intermediary in Catalytic Amination, Reductive Elimination of Ethers, and Catalytic Etheration. Comments on Alcohol Elimination from Ir(III) J. Am. Chem. Soc. 118 : 13109–13110 (1996).

Wolfe P. J. and Buchwald L. S. " Palladium Catalyzed Amination of Aryl Iodides ", J. Org. Chem. 61: 1133–1135 (1996).

Zhao, et al. " Synthesis of Arylpiperazines via Palladium–Catalyzed Aromatic Amination Reaction with Unprotected Piperazines", Tetrahedron Letters 37(26): 4463–4466 (1996).

Yoshikawa et al.; "A New Type of Atropisomeric Biphenyl–bisphosphine Ligand, (R)– MOC– BIMOP and Its Use in Efficient Asymmetric Hydrogenation of α– Aminoketone and Itaconic Acid [1)]", Tetrahedron Asymmetry, 3(1): 13–16, (1992).

Bayston et al.; "Preparation and Use of a Polymer Supported BINAP Hydrogenation Catalyst", J.Org. Chem. 63:3137–3140, (1998).

Enev et al.; " a Bis–Steroidal Phosphine as New Chiral Hydrogenation Ligand", J. Org. Chem. 62: 7092–7093, (1997).

Murata et al.; "Synthesis of Atropisomeric Biphenylbisphosphine, 6,6'-Bis(Dicyclohexylphosphino)-3'-Dimethoxy-2,2',4,4'-Tetramethyl—1,1'-Biphenyl and its Use In Rhodium (I)- Catalyzed Asymmetric Hydrogenation [1]", Chem. Pharm. Bull. 39(10): 2767–2769, (1991).

Schmid et al.; "35. Axially Asymmetric Diphosphines in the Biphenyl Series: Synthesis of (6,6'-Dimethoxybiphenyl-2,2'—diyl)bis(diphenylphosphine) ('MeO–BIPHEP') and Analogues via an ortho– Lithiation/ Iodination Ullmann–Reaction Approach", Helvetica Chimica Acta vol. 74: 370–389 (1991).

Uozumi et al.; "Synthesis of Optically Active 2–(Diarylphosphino)– 1,1'—bynaphthyls, Efficient Chiral Monodentate Phosphine Ligands", J. Org. Chem. 58: 1945–1948, (1993).

VyskoČil et al.; "Derivatives of 2– amino– 2'—diphenylphosphino–1,1'–binaphthyl (MAP) and Their Application in Asymmetric Palladium (0)–Catalyzed Allylic Substitution", J. Org. Chem. 63: 7738–7748, (1998).

Zhang et al.; "Synthesis of Partially Hydrogenated BINAP Variants", Tetrahedron Letters 32(49): 7283–7286, (1991).

* cited by examiner

Figure 1. Method of Preparation and Reactions Screened for Various Ligands.
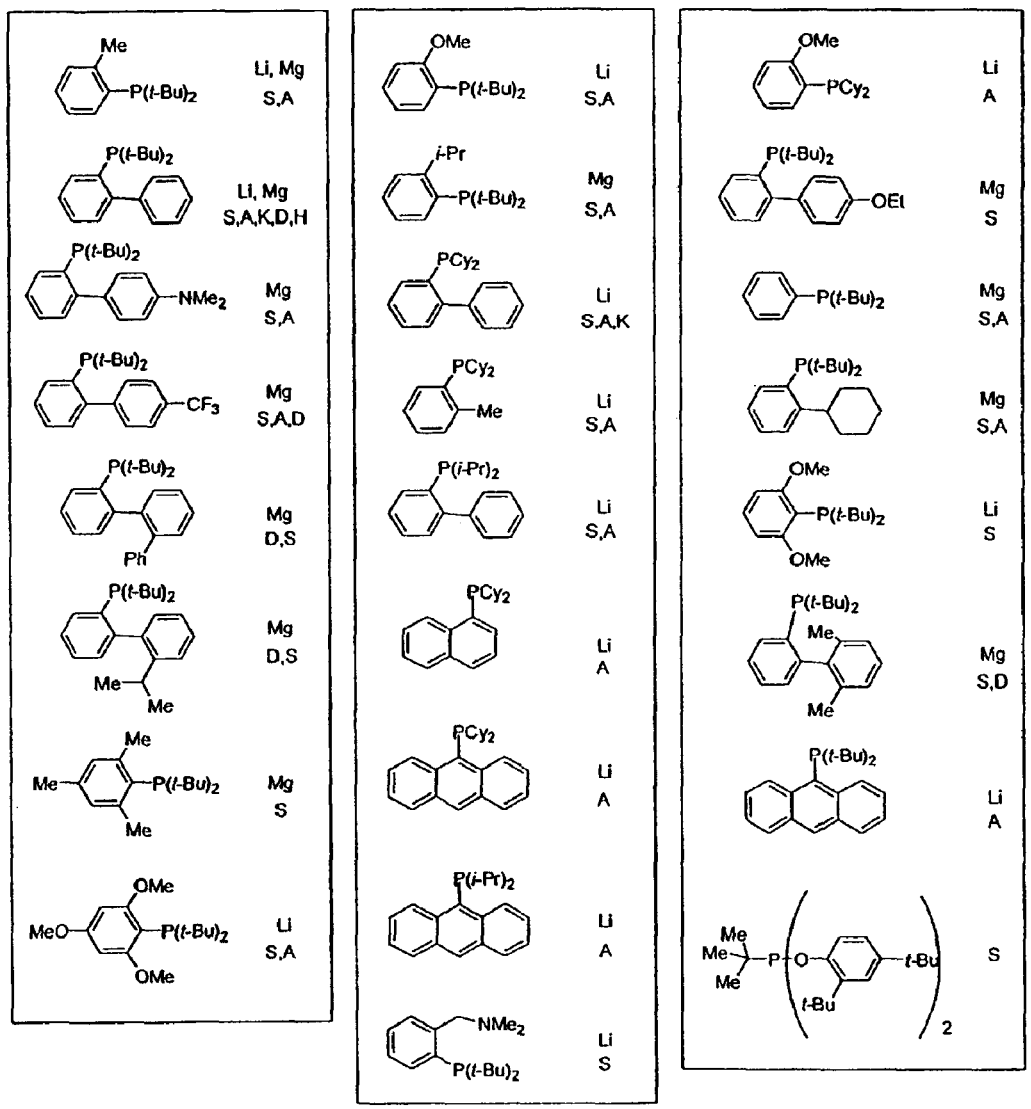
Legend
*Method of Preparation:*
Li= made from organolithium reagent
Mg= made from Grignard reagent
*Reactions Screened:*
S=Used for Suzuki Coupling
A=Used for amination
D=Used for diaryl ether synthesis
K=Used for ketone arylation
H=Used for Heck reaction

LIGANDS FOR METALS AND IMPROVED METAL-CATALYZED PROCESSES BASED THEREON

RELATED APPLICATIONS

This application is a division of U.S. Ser. No. 10/004,101, filed Oct. 23, 2001; which is a continuation of U.S. Ser. No. 09/231,315, filed Jan. 13, 1999, now U.S. Pat. No. 6,307,087; which is a continuation-in-part of U.S. Ser. No. 09/113,478, filed Jul. 10, 1998, now U.S. Pat. No. 6,395,916.

GOVERNMENT FUNDING

This invention was made with support under Grant Number 942 1982-CHE, awarded by the National Science Foundation; the government, therefore, has certain rights in the invention.

BACKGROUND OF THE INVENTION

Transition metal catalyst complexes play important roles in many areas of chemistry, including the preparation of polymers and pharmaceuticals. The properties of these catalyst complexes are recognized to be influenced by both the characteristics of the metal and those of the ligands associated with the metal atom. For example, structural features of the ligands can influence reaction rate, regioselectivity, and stereoselectivity. Bulky ligands can be expected to slow reaction rate; electron-withdrawing ligands, in coupling reactions, can be expected to slow oxidative addition to, and speed reductive elimination from, the metal center; and electron-rich ligands, in coupling reactions, conversely, can be expected to speed oxidative addition to, and slow reductive elimination from, the metal center.

In many cases, the oxidative addition step in the accepted mechanism of a coupling reaction is deemed to be rate limiting. Therefore, adjustments to the catalytic system as a whole that increase the rate of the oxidative addition step should increase overall reaction rate. Additionally, the rate of oxidative addition of a transtion metal catalyst to the carbon-halogen bond of an aryl halide is known to decrease as the halide is varied from iodide to bromide to chloride, all other factors being equal. Because of this fact, the more stable, lower molecular weight, and arguably more easy to obtain, members of the set of reactive organic halides—the chlorides—are the poorest substrates for traditional transition metal catalyzed coupling reactions and the like.

To date, the best halogen-containing substrates for transtion metal catalyzed carbon-heteroatom and carbon-carbon bond forming reactions have been the iodides. Bromides have often been acceptable substrates, but typically required higher temperatures, longer reaction times, and gave lower yields of products.

SUMMARY OF THE INVENTION

One aspect of the present invention relates to novel bidentate ligands for transition metals. A second aspect of the present invention relates to the use of catalysts comprising these ligands in transition metal-catalyzed carbon-heteroatom and carbon-carbon bond-forming reactions. The subject methods provide improvements in many features of the transition metal-catalyzed reactions, including the range of suitable substrates, number of catalyst turnovers, reaction conditions, and efficiency.

Unexpected, pioneering improvements over the prior art have been realized in transition metal-catalyzed: aryl amination reactions; Suzuki couplings to give both biaryl and alkylaryl products; and α-arylations of ketones. The ligands and methods of the present invention enable for the first time, the efficient use of aryl chlorides, inter alia, in the aforementioned reactions. Additionally, the ligands and methods of the present invention enable for the first time transformations utilizing aryl bromides or chlorides to proceed-efficiently at room temperature. Furthermore, the ligands and methods of the present invention enable the aforementioned reactions to occur at synthetically useful rates using extremely small amounts of catalyst, e.g., 0.000001 mol % relative to the limiting reagent.

BRIEF DESCRIPTION OF THE FIGURE

FIG. 1 depicts method of preparation and reactions screened for various ligands.

DETAILED DESCRIPTION OF THE INVENTION

I. Compounds and Methods of the Invention.

In one aspect of the invention, novel ligands for metals, preferably transition metals, are provided. In certain embodiments, the subject ligands are represented by general structure 1:

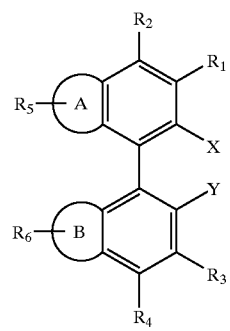

wherein
each of A and B independently represent fused rings selected from a group consisting of monocyclic or polycyclic cycloalkyls, cycloalkenyls, aryls, and heterocyclic rings, said rings comprising from 4 to 8 atoms in a ring structure;
X and Y represent, independently for each occurrence, $NR_2$, $PR_2$, $AsR_2$, $OR$, or $SR$;
R, $R_1$, $R_2$, $R_3$, and $R_4$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;
$R_5$ and $R_6$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or $-(CH_2)_m-R_{80}$;
A and B independently may be unsubstituted or substituted with $R_5$ and $R_6$, respectively, any number of times up to the limitations imposed by stability and the rules of valence;

$R_1$ and $R_2$, and/or $R_3$ and $R_4$, taken together may represent a ring comprising a total of 5–7 atoms in the backbone of said ring; said ring may comprise one or two heteroatoms in its backbone; and said ring may bear additional substituents or be unsubstituted;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 1, and the associated definitions, wherein:

X and Y are not identical;

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;

$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$; and $R_5$ and $R_6$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 1, and the associated definitions, wherein:

X is hydrogen;

Y represents $PR_2$;

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;

$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$; and $R_5$ and $R_6$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 1, and the associated definitions, wherein:

X is hydrogen;

Y represents $PR_2$;

R is selected, independently for each occurrence, from the set comprising alkyl and cycloalkyl;

$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$; and $R_5$ and $R_6$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

The ligands of the present invention may have the same constitution as general structure 1, but differing to the extent that either one or both of fused rings A and B are fused to faces of the phenyl rings of 1 other than those to which they are fused in 1. Additionally, the invention contemplates ligands in which one or more of the ring carbons of the phenyl rings of 1 are replaced with a heteroatom, e.g., N, O, P, or S, as valence and stability permit.

In certain embodiments, the subject ligands are represented by general structure 2:

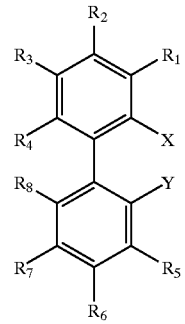

wherein

X and Y represent, independently for each occurrence, $NR_2$, $PR_2$, $AsR_2$, OR, or SR;

R, $R_1$, $R_2$, $R_3$, $R_4$, $R_5$, $R_6$, $R_7$, and $R_8$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

any pair(s) of substituents, with an ortho-relationship therebetween, selected from the group consisting of $R_1$, $R_2$, $R_3$, $R_4$, $R_5$, $R_6$, $R_7$, and $R_8$, taken together may represent a ring comprising a total of 5–7 atoms in the backbone of said ring; said ring may comprise one or two heteroatoms in its backbone; and said ring may bear additional substituents or be unsubstituted;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 2, and the associated definitions, wherein:

X and Y are not identical;

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$; and $R_1$, $R_2$, $R_3$, $R_4$, $R_5$, $R_6$, $R_7$, and $R_8$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 2, and the associated definitions, wherein:

X is hydrogen;

Y represents $PR_2$;

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$; and $R_1$, $R_2$, $R_3$, $R_4$, $R_5$, $R_6$, $R_7$, and $R_8$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 2, and the associated definitions, wherein:

X is hydrogen;
Y represents $PR_2$;
R is selected, independently for each occurrence, from the set comprising alkyl and cycloalkyl;
$R_1$, $R_2$, $R_3$, $R_4$, $R_5$, $R_6$, $R_7$, and $R_8$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the subject ligands are represented by general structure 3:

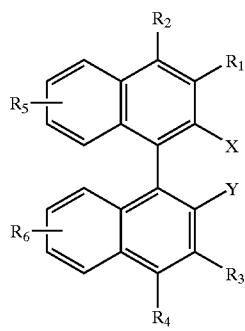

3 wherein
X and Y represent, independently for each occurrence, $NR_2$, $PR_2$, $AsR_2$, OR, or SR;
R, $R_1$, $R_2$, $R_3$, and $R_4$, for each occurrence, independently represent hydrogen, halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;
$R_5$ and $R_6$, for each occurrence, independently represent halogen, alkyl, alkenyl, alkynyl, hydroxyl, alkoxyl, silyloxy, amino, nitro, sulfhydryl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;
the B and B' rings of the binaphthyl core independently may be unsubstituted or substituted with $R_5$ and $R_6$, respectively, any number of times up to the limitations imposed by stability and the rules of valence;
$R_1$ and $R_2$, and/or $R_3$ and $R_4$, taken together may represent a ring comprising a total of 5–7 -atoms in the backbone of said ring; said ring may comprise one or two heteroatoms in its backbone; and said ring may bear additional substituents or be unsubstituted;
$R_{80}$ represents an unsubstituted or substituted aryl, a cycloalkyl, a cycloalkenyl, a heterocycle, or a polycycle;
m is an integer in the range 0 to 8 inclusive; and
the ligand, when chiral, may be provided in the form of a mixture of enantiomers or as a single enantiomer.

In certain embodiments, the ligands are represented by general structure 3, and the associated definitions, wherein:
X and Y are not identical;

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;
$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$; and
$R_5$ and $R_6$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 3, and the associated definitions, wherein:
X is hydrogen;
Y is $PR_2$;
R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;
$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m R_{80}$; and
$R_5$ and $R_6$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the ligands are represented by general structure 3, and the associated definitions, wherein:
X is hydrogen;
Y is $PR_2$;
R is selected, independently for each occurrence, from the set comprising alkyl and cycloalkyl;
$R_1$, $R_2$, $R_3$, and $R_4$ are selected, independently for each occurrence, from the set comprising H, alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$; and
$R_5$ and $R_6$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$.

In certain embodiments, the subject ligands are represented by general structure 4:

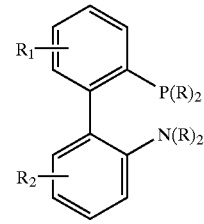

4 wherein
R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;
the A and A' rings of the biphenyl core independently may be unsubstituted or substituted with $R_1$ and $R_2$, respectively, any number of times up to the limitations imposed by stability and the rules of valence;
$R_1$ and $R_2$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 4, and the associated definitions, wherein:

$R_1$ and $R_2$ are hydrogen;

both instances of R on the N depicted explicitly are lower alkyl, preferably methyl; and both instances of R on P depicted explicitly are cycloalkyl, preferably cyclohexyl.

In certain embodiments, the subject ligands are represented by general structure 5:

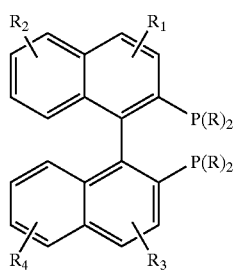

5 wherein

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;

the A, B, A', and B' rings of the binaphthyl core independently may be unsubstituted or substituted with $R_1$, $R_2$, $R_3$, and $R_4$, respectively, any number of times up to the limitations imposed by stability and the rules of valence;

$R_1$, $R_2$, $R_3$, and $R_4$, are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 5, and the associated definitions, wherein:

$R_1$, $R_2$, $R_3$, and $R_4$, are absent; and all instances of R are lower alkyl or cycloalkyl, preferably cyclohexyl.

In certain embodiments, the subject ligands are represented by general structure 6:

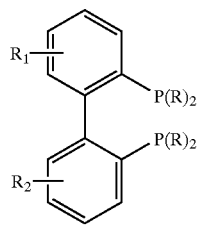

6 wherein

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;

the A and A' rings of the biphenyl core independently may be unsubstituted or substituted with $R_1$ and $R_2$, respectively, any number of times up to the limitations imposed by stability and the rules of valence;

$R_1$ and $R_2$ are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 6, and the associated definitions, wherein:

$R_1$ and $R_2$ are absent; and all instances of R are lower alkyl or cycloalkyl, preferably cyclohexyl.

In certain embodiments, the subject ligands are represented by general structure 7:

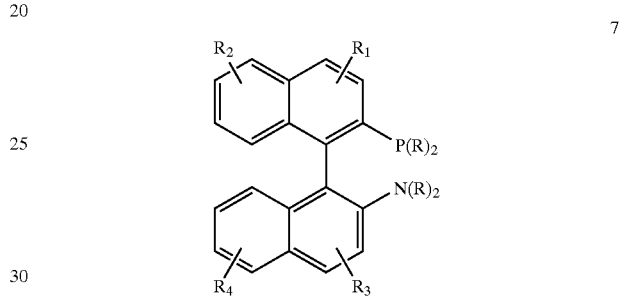

7 wherein

R is selected, independently for each occurrence, from the set comprising alkyl, heteroalkyl, cycloalkyl, heterocycloalkyl, aryl, heteroaryl, aralkyl, heteroaralkyl, and —$(CH_2)_m$—$R_{80}$;

the A, B, A', and B' rings of the binaphthyl core independently may be unsubstituted or substituted with $R_1$, $R_2$, $R_3$, and $R_4$, respectively, any number of times up to the limitations imposed by stability and the rules of valence;

$R_1$, $R_2$, $R_3$, and $R_4$, are selected, independently for each occurrence, from the set comprising alkyl, heteroalkyl, cycloalkyl, heterocycloalkyl, aryl, heteroaryl, aralkyl, heteroaralkyl, halogen, —$SiR_3$, and —$(CH_2)_m$—$R_{80}$;

$R_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the ligands are represented by general structure 7, and the associated definitions, wherein:

$R_1$, $R_2$, $R_3$, and $R_4$, are absent;

both instances of R on the N depicted explicitly are lower alkyl, preferably methyl; and both instances of R on P depicted explicitly are cycloalkyl, preferably cyclohexyl.

In certain embodiments, the subject ligands are represented by general structure 8:

8 wherein

Ar and Ar' are independently selected from the group consisting of optionally substituted aryl and heteroaryl moieties; and X and Y represent, independently for each occurrence, NR$_2$, PR$_2$, AsR$_2$, OR, or SR;

R is selected, independently for each occurrence, from the set comprising alkyl, heteroalkyl, cycloalkyl, heterocycloalkyl, aryl, heteroaryl, aralkyl, heteroaralkyl, and —(CH$_2$)$_m$—R$_{80}$;

R$_{80}$ represents an unsubstituted or substituted aryl, a cycloalkyl, a cycloalkenyl, a heterocycle, or a polycycle;

m is an integer in the range 0 to 8 inclusive; and the ligand, when chiral, may be provided in the form of a mixture of enantiomers or as a single enantiomer.

In certain embodiments, the subject method is represented by the generalized reaction depicted in Scheme 1:

Scheme 1

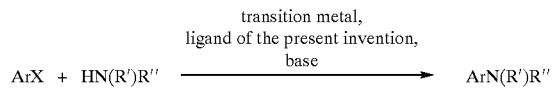

wherein

Ar is selected from the set comprising optionally substituted monocyclic and polycyclic aromatic and heteroaromatic moieties;

X is selected from the set comprising Cl, Br, I, —OS(O)$_2$alkyl, and —OS(O)$_2$aryl;

R' and R" are selected, independently for each occurrence, from the set comprising H, alkyl, heteroalkyl, aryl, heteroaryl, aralkyl, alkoxyl, amino, trialkylsilyl, and triarylsilyl;

R' and R", taken together, may form an optionally substituted ring consisting of 3–10 backbone atoms inclusive; said ring optionally comprising one or more heteroatoms beyond the nitrogen to which R' and R" are bonded;

R' and/or R" may be covalently linked to Ar such that the amination reaction is intramolecular;

the transition metal is selected from the set of groups 5–12 metals, preferably the Group VIIIA metals;

the ligand is selected from the set comprising 1–8 inclusive; and the base is selected from the set comprising hydrides, carbonates, phosphates, alkoxides, amides, carbanions, and silyl anions.

In certain embodiments, the subject method is represented by Scheme 1 and the associated definitions, wherein
the ligand is 2;
the transition metal is palladium; and
the base is an alkoxide, amide, phosphate, or carbonate.

In certain embodiments, the subject method is represented by Scheme 1 and the associated definitions, wherein
the ligand is 2, wherein X is hydrogen, and Y represents P(alkyl)$_2$; and
X represents Cl or Br.

In certain embodiments, the subject method is represented by Scheme 1 and the associated definitions, wherein
the ligand is 4;
the transition metal is palladium; and
the base is an alkoxide, amide, phosphate, or carbonate.

In certain embodiments, the subject method is represented by Scheme 1 and the associated definitions, wherein
the ligand is 4, wherein R$_1$ and R$_2$ are absent; P(R)$_2$ represents PCy$_2$, and N(R)$_2$ represents NMe$_2$; and
X represents Cl or Br.

In certain embodiments, the subject method is represented by Scheme 1 and the associated definitions, wherein: HN(R')R" represents an optionally substituted heteroaromatic compound, e.g., pyrrole, indole, or carbazole.

In certain embodiments, the subject method is represented by Scheme 1 and the associated definitions, wherein: X represents Cl; the ligand is 4, wherein R$_1$ and R$_2$ are absent, P(R)$_2$ represents PCy$_2$, and N(R)$_2$ represents NMe$_2$; the transition metal is palladium; and the base is an alkoxide, amide, phosphate, or carbonate.

In certain embodiments, the subject method is represented by Scheme 1 and the associated definitions, wherein: X represents Br or I; the ligand is 4, wherein R$_1$ and R$_2$ are absent, P(R)$_2$ represents PCy$_2$, and N(R)$_2$ represents NMe$_2$; the transition metal is palladium; the base is an alkoxide, amide, phosphate, or carbonate; and the transformation occurs at room temperature.

In certain embodiments, the subject method is represented by Scheme 1 and the associated definitions, wherein: the ligand is 5; the transition metal is palladium; and the base is an alkoxide, amide, phosphate, or carbonate.

In certain embodiments, the subject method is represented by Scheme 1 and the associated definitions, wherein: X represents Cl; the ligand is 5, wherein R$_1$, R$_2$, R$_3$, and R$_4$ are absent, and all occurrences of R are cyclohexyl; the transition metal is palladium; and the base is an alkoxide, amide, phosphate, or carbonate.

In certain embodiments, the subject method is represented by Scheme 1 and the associated definitions, wherein: the ligand is 2, wherein X and Y both represent PR$_2$; the transition metal is palladium; and the base is an alkoxide, amide, phosphate, or carbonate.

In certain embodiments, the subject method is represented by Scheme 1 and the associated definitions, wherein: X represents Cl; the ligand is 2, wherein X and Y both represent PR$_2$, and R$_1$, R$_2$, R$_3$, R$_4$, R$_5$, R$_6$, R$_7$, and R$_8$ are hydrogen, and all occurrences of R are alkyl; the transition metal is palladium; and the base is an alkoxide, amide, phosphate, or carbonate.

Those of ordinary skill in the art will recognize that in the described embodiments based on Scheme 1, (alkenyl)X may serve as a surrogate for ArX.

In certain embodiments, the methods according to Scheme 1 provide the product in a yield of greater than 50%; in more preferred embodiments, the product is provided in a yield of greater than 70%; and in the most preferred embodiments, the product is provided in a yield of greater than 85%.

In certain embodiments, the subject method is represented by Scheme 1 and the associated definitions, wherein the transition metal and ligand are selected to provide the product at room temperature.

In certain embodiments, the subject method is represented by Scheme 1 and the associated definitions, wherein the transition metal and ligand are selected to provide the product when X is chloride.

In certain embodiments, the subject method is represented by Scheme 1 and the associated definitions, wherein the transition metal and ligand are selected to provide the product utilizing less than 0.01 mol % of the catalyst relative to the limiting reagent.

In certain embodiments, the subject method is represented by Scheme 1 and the associated definitions, wherein the transition metal and ligand are selected to provide the product utilizing less than 0.0001 mol % of the catalyst relative to the limiting reagent.

In certain embodiments, the subject method is represented by Scheme 1 and the associated definitions, wherein the transition metal and ligand are selected to consume the limiting reagent in less than 48 hours.

In certain embodiments, the subject method is represented by Scheme 1 and the associated definitions, wherein the transition metal and ligand are selected to consume the limiting reagent in less than 24 hours.

In certain embodiments, the subject method is represented by Scheme 1 and the associated definitions, wherein the transition metal and ligand are selected to consume the limiting reagent in less than 12 hours.

In certain embodiments, the subject method is represented by the generalized Suzuki coupling reaction depicted in Scheme 2:

Scheme 2

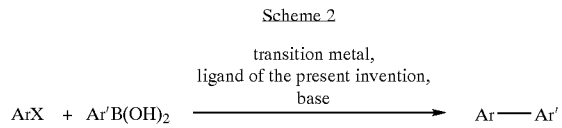

wherein

Ar and Ar' are independently selected from the set comprising optionally substituted monocyclic and polycyclic aromatic and heteroaromatic moieties;

X is selected from the set comprising Cl, Br, I, —OS(O)$_2$alkyl, and —OS(O)$_2$aryl;

Ar and Ar' may be covalently linked such that the reaction is intramolecular;

the transition metal is selected from the set of groups 5–12 metals, preferably the Group VIIIA metals;

the ligand is selected from the set comprising 1–8 inclusive; and the base is selected from the set comprising carbonates, phosphates, fluorides, alkoxides, amides, carbanions, and silyl anions.

In certain embodiments, the subject method is represented by Scheme 2 and the associated definitions, wherein the ligand is 2;

the transition metal is palladium; and the base is an alkoxide, amide, phosphate, or carbonate.

In certain embodiments, the subject method is represented by Scheme 2 and the associated definitions, wherein the ligand is 2, wherein X is hydrogen, and Y represents P(alkyl)$_2$; and X represents Cl or Br.

In certain embodiments, the subject method is represented by Scheme 2 and the associated definitions, wherein the transition metal is palladium;

the ligand is 4; and the base is an alkoxide, amide, carbonate, phosphate, or fluoride.

In certain embodiments, the subject method is represented by Scheme 2 and the associated definitions, wherein the ligand is 4, wherein R$_1$ and R$_2$ are absent; P(R)$_2$ represents PCy$_2$, and N(R)$_2$ represents NMe$_2$;

X represents Cl or Br; and the reaction occurs at room temperature.

Those of ordinary skill in the art will recognize that in the described embodiments based on Scheme 2, (alkenyl)X may serve as a surrogate for ArX, and/or (alkenyl)B(OH)$_2$ may serve as a surrogate for ArB(OH)$_2$.

In certain embodiments, the methods according to Scheme 2 provide the product in a yield of greater than 50%; in more preferred embodiments, the product is provided in a yield of greater than 70%; and in the most preferred embodiments, the product is provided in a yield of greater than 85%.

In certain embodiments, the subject method is represented by Scheme 2 and the associated definitions, wherein the transition metal and ligand are selected to provide the product at room temperature.

In certain embodiments, the subject method is represented by Scheme 2 and the associated definitions, wherein the transition metal and ligand are selected to provide the product when X is chloride.

In certain embodiments, the subject method is represented by Scheme 2 and the associated definitions, wherein the transition metal and ligand are selected to provide the product utilizing less than 0.01 mol % of the catalyst relative to the limiting reagent.

In certain embodiments, the subject method is represented by Scheme 2 and the associated definitions, wherein the transition metal and ligand are selected to provide the product utilizing less than 0.0001 mol % of the catalyst relative to the limiting reagent.

In certain embodiments, the subject method is represented by Scheme 2 and the associated definitions, wherein the transition metal and ligand are selected to consume the limiting reagent in less than 48 hours.

In certain embodiments, the subject method is represented by Scheme 2 and the associated definitions, wherein the transition metal and ligand are selected to consume the limiting reagent in less than 24 hours.

In certain embodiments, the subject method is represented by Scheme 2 and the associated definitions, wherein the transition metal and ligand are selected to consume the limiting reagent in less than 12 hours.

In certain embodiments, the subject method is represented by the generalized Suzuki coupling reaction depicted in Scheme 3:

Scheme 3

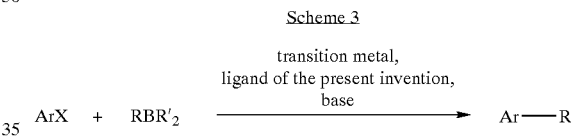

wherein

Ar is selected from the set comprising optionally substituted monocyclic and polycyclic aromatic and heteroaromatic moieties;

R is selected from the set comprising optionally substituted alkyl, heteroalkyl, and aralkyl;

R' is selected, independently for each occurrence, from the set of alkyl and heteroalkyl; the carbon-boron bond of said alkyl and heteroalkyl groups being inert under the reaction conditions, e.g., BR'$_2$ taken together represents 9-borobicyclo[3.3.1]nonyl.

X is selected from the set comprising Cl, Br, I, —OS(O)$_2$alkyl, and —OS(O)$_2$aryl;

Ar and R may be covalently linked such that the reaction is intramolecular;

the transition metal is selected from the set of groups 5–12 metals, preferably the Group VIIIA metals;

the ligand is selected from the set comprising 1–8 inclusive; and the base is selected from the set comprising carbonates, phosphates, fluorides, alkoxides, amides, carbanions, and silyl anions.

In certain embodiments, the subject method is represented by Scheme 3 and the associated definitions, wherein the ligand is 2;

the transition metal is palladium; and the base is an alkoxide, amide, phosphate, or carbonate.

In certain embodiments, the subject method is represented by Scheme 3 and the associated definitions, wherein the ligand is 2, wherein X is hydrogen, and Y represents P(alkyl)$_2$; and X represents Cl or Br.

In certain embodiments, the subject method is represented by Scheme 3 and the associated definitions, wherein X represents Cl or Br;

the transition metal is palladium;

the ligand is 4; and the base is an alkoxide, amide, carbonate, phosphate, or fluoride.

In certain embodiments, the subject method is represented by Scheme 3 and the associated definitions, wherein the ligand is 4, wherein $R_1$ and $R_2$ are absent; $P(R)_2$ represents $PCy_2$, and $N(R)_2$ represents $NMe_2$; and X represents Cl.

Those of ordinary skill in the art will recognize that in the described embodiments based on Scheme 3, (alkenyl)X may serve as a surrogate for ArX.

In certain embodiments, the methods according to Scheme 3 provide the product in a yield of greater than 50%; in more preferred embodiments, the product is provided in a yield of greater than 70%; and in the most preferred embodiments, the product is provided in a yield of greater than 85%.

In certain embodiments, the subject method is represented by Scheme 3 and the associated definitions, wherein the transition metal and ligand are selected to provide the product at room temperature.

In certain embodiments, the subject method is represented by Scheme 3 and the associated definitions, wherein the transition metal and ligand are selected to provide the product when X is chloride.

In certain embodiments, the subject method is represented by Scheme 3 and the associated definitions, wherein the transition metal and ligand are selected to provide the product utilizing less than 0.01 mol % of the catalyst relative to the limiting reagent.

In certain embodiments, the subject method is represented by Scheme 3 and the associated definitions, wherein the transition metal and ligand are selected to provide the product utilizing less than 0.0001 mol % of the catalyst relative to the limiting reagent.

In certain embodiments, the subject method is represented by Scheme 3 and the associated definitions, wherein the transition metal and ligand are selected to consume the limiting reagent in less than 48 hours.

In certain embodiments, the subject method is represented by Scheme 3 and the associated definitions, wherein the transition metal and ligand are selected to consume the limiting reagent in less than 24 hours.

In certain embodiments, the subject method is represented by Scheme 3 and the associated definitions, wherein the transition metal and ligand are selected to consume the limiting reagent in less than 12 hours.

In certain embodiments, the subject method is represented by the generalized α-arylation reaction depicted in Scheme 4:

Scheme 4

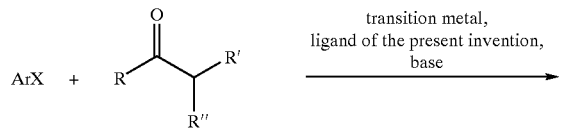

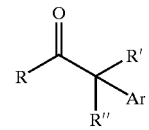

wherein

Ar is selected from the set comprising optionally substituted monocyclic and polycyclic aromatic and heteroaromatic moieties;

R, R', and R" are selected, independently for each occurrence, from the set comprising H, alkyl, heteroalkyl, aralkyl, aryl, heteroaryl;

X is selected from the set comprising Cl, Br, I, —OS(O)$_2$alkyl, and —OS(O)$_2$aryl;

Ar and one of R, R', and R" may be covalently linked such that the reaction is intramolecular;

the transition metal is selected from the set of groups 5–12 metals, preferably the Group VIIIA metals;

the ligand is selected from the set comprising 1–8 inclusive; and the base is selected from the set comprising carbonates, phosphates, fluorides, alkoxides, amides, carbanions, and silyl anions.

In certain embodiments, the subject method is represented by Scheme 4 and the associated definitions, wherein the ligand is 2;

the transition metal is palladium; and the base is an alkoxide, amide, phosphate, or carbonate.

In certain embodiments, the subject method is represented by Scheme 4 and the associated definitions, wherein the ligand is 2, wherein X is hydrogen, and Y represents $P(alkyl)_2$; and X represents Cl or Br.

In certain embodiments, the subject method is represented by Scheme 4 and the associated definitions, wherein X represents Cl or Br;

the transition metal is palladium;

the ligand is 4; and the base is an alkoxide, or amide.

In certain embodiments, the subject method is represented by Scheme 4 and the associated definitions, wherein the ligand is 4, wherein $R_1$ and $R_2$ are absent; $P(R)_2$ represents $PCy_2$, and $N(R)_2$ represents $NMe_2$.

In certain embodiments, the subject method is represented by Scheme 4 and the associated definitions, wherein X represents Br; and the reaction occurs at room temperature.

Those of ordinary skill in the art will recognize that in the described embodiments based on Scheme 4, (alkenyl)X may serve as a surrogate for ArX.

In certain embodiments, the methods according to Scheme 4 provide the product in a yield of greater than 50%; in more preferred embodiments, the product is provided in a yield of greater than 70%; and in the most preferred embodiments, the product is provided in a yield of greater than 85%.

In certain embodiments, the subject method is represented by Scheme 4 and the associated definitions, wherein the transition metal and ligand are selected to provide the product at room temperature.

In certain embodiments, the subject method is represented by Scheme 4 and the associated definitions, wherein the transition metal and ligand are selected to provide the product when X is chloride.

In certain embodiments, the subject method is represented by Scheme 4 and the associated definitions, wherein the transition metal and ligand are selected to provide the product utilizing less than 0.01 mol % of the catalyst relative to the limiting reagent.

In certain embodiments, the subject method is represented by Scheme 4 and the associated definitions, wherein the transition metal and ligand are selected to provide the product utilizing less than 0.0001 mol % of the catalyst relative to the limiting reagent.

In certain embodiments, the subject method is represented by Scheme 4 and the associated definitions, wherein the transition metal and ligand are selected to consume the limiting reagent in less than 48 hours.

In certain embodiments, the subject method is represented by Scheme 4 and the associated definitions, wherein the transition metal and ligand are selected to consume the limiting reagent in less than 24 hours.

In certain embodiments, the subject method is represented by Scheme 4 and the associated definitions, wherein the transition metal and ligand are selected to consume the limiting reagent in less than 12 hours.

In preferred embodiments of the reactions of the invention, there is no need to use large excesses of reactants, e.g., amine, boronic acid, ketone and the like, or aromatic compound. The reactions proceed quickly and in high yield to the desired products using substantially stoichiometric amounts of reagents. For example, in the amination reactions of the invention, the amine may be present in as little as a two-fold excess and preferably in no greater than a 20% excess relative to the aromatic compound. Alternatively, the aromatic compound may be present in as little as a two-fold excess and preferably in no greater than a 20% excess relative to the amine. An analogous discussion applies to the subject Suzuki couplings and α-arylations.

The reactions typically proceed at mild temperatures and pressures to give high yields of the product aryl amines, biaryls, α-aryl ketones, and the like. Thus, yields of desired products greater than 45%, preferably greater than 75%, and even more preferably greater than 80%, may be obtained from reactions at mild temperatures according to the invention. The reaction may be carried out at temperature less than 120° C., and preferably in the range of 20–100° C. In certain preferred embodiments, the reactions are carried out at ambient temperature.

The reactions can be run in a wide range of solvent systems, including polar aprotic solvents. Alternatively, in certain embodiments, the subject reactions may be carried in the absence of added solvent.

The ability to provide synthesis schemes for aryl amines, biaryls, α-aryl ketones, and the like, which can be carried out under mild conditions and/or with non-polar solvents has broad application, especially in the agricultural and pharmaceutical industries, as well as in the polymer industry. In this regard, the subject reactions are particularly well-suited to reactants or products which include sensitive functionalities, e.g., which would otherwise be labile under harsh reaction conditions.

The subject amine arylation, Suzuki coupling, ketone α-arylation reactions and the like can be used as part of combinatorial synthesis schemes to yield libraries of aryl amines, biaryls, α-aryl ketones, and the like. Accordingly, another aspect of the present invention relates to use of the subject method to generate variegated libraries of aryl amines, biaryls, α-aryl ketones, and the like, and to the libraries themselves. The libraries can be soluble or linked to insoluble supports, e.g., through a substituent of a reactant (prior to carrying out a reaction of the present invention), e.g., the aryl group, amine, boronic acid, ketone, or the like, or through a substituent of a product (subsequent to carrying out a reaction of the present invention), e.g., the aryl amine, biaryl, α-aryl ketone, or the like.

The ligands of the present invention and the methods based thereon enable the formation of carbon-heteroatom and carbon-carbon bonds—via transition metal catalyzed aminations, Suzuki couplings, α-arylations of carbonyls, and the like—under conditions that would not yield appreciable amounts of the observed product(s) using ligands and methods known in the art. In preferred embodiments, the ligands and methods of the present invention catalyze the aforementioned transformations at temperatures below 50° C., and in certain embodiments they occur at room temperature. When a reaction is said to occur under a given set of conditions it means that the rate of the reaction is such the bulk of the starting materials is consumed, or a significant amount of the desired product is produced, within 48 hours, and preferably within 24 hours, and most preferably within 12 hours. In certain embodiments, the ligands and methods of the present invention catalyze the aforementioned transformations utilizing less than 1 mol % of the catalyst complex relative to the limiting reagent, in certain preferred embodiments less than 0.01 mol % of the catalyst complex relative to the limiting reagent, and in additional preferred embodiments less than 0.0001 mol % of the catalyst complex relative to the limiting reagent.

The ligands of the present invention and the methods based thereon can be used to produce synthetic intermediates that, after being subjected to additional methods known in the art, are transformed to desired end products, e.g., lead compounds in medicinal chemistry programs, pharmaceuticals, insecticides, antivirals and antifungals. Furthermore, the ligands of the present invention and the methods based thereon may be used to increase the efficiency of and/or shorten established routes to desired end products, e.g., lead compounds in medicinal chemistry programs, pharmaceuticals, insecticides, antivirals and antifungals.

II Definitions

For convenience, before further description of the present invention, certain terms employed in the specification, examples, and appended claims are collected here.

The terms "biphenyl" and "binaphthylene" refer to the ring systems below. The numbers around the peripheries of the ring systems are the positional numbering systems used herein. Likewise, the capital letters contained within the individual rings of the ring systems are the ring descriptors used herein.

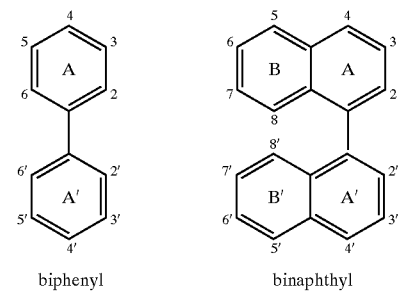

biphenyl            binaphthyl

The term "substrate aryl group" refers to an aryl group containing an electrophilic atom which is susceptible to the subject cross-coupling reaction, e.g., the electrophilic atom bears a leaving group. In reaction scheme 1, the substrate aryl is represented by ArX, and X is the leaving group. The aryl group, Ar, is said to be substituted if, in addition to X, it is substituted at yet other positions. The substrate aryl group can be a single ring molecule, or can be a component of a larger molecule.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The terms "electrophilic atom", "electrophilic center" and "reactive center" as used herein refer to the atom of the substrate aryl moiety which is attacked by, and forms a new bond to the nucleophilic heteroatom of the hydrazine and the like. In most (but not all) cases, this will also be the aryl ring atom from which the leaving group departs.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (s) constant. This well known constant is described in many references, for instance, J. March, *Advanced Organic Chemistry*, McGraw Hill Book Company, New York, (1977 edition) pp. 251–259. The Hammett constant values are generally negative for electron donating groups (s[P]=−0.66 for $NH_2$) and positive for electron withdrawing groups (s[P]=0.78 for a nitro group), (s[P] indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "reaction product" means a compound which results from the reaction of the hydrazine or the like and the substrate aryl group. In general, the term "reaction product" will be used herein to refer to a stable, isolable aryl ether adduct, and not to unstable intermediates or transition states.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through nonadjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

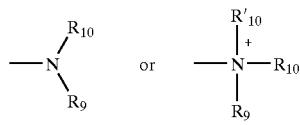

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

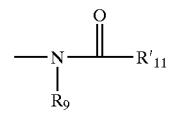

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

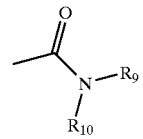

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S-$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

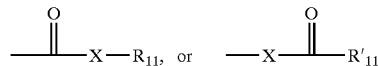

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolfornate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

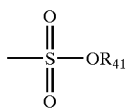

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

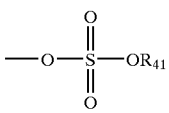

in which $R_{41}$ is as defined above.

The term "sulfonamido" is art recognized and includes a moiety that can be represented by the general formula:

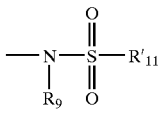

in which $R_9$ and $R'_{11}$ are as defined above.

The term "sulfamoyl" is art-recognized and includes a moiety that can be represented by the general formula:

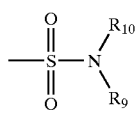

in which $R_9$ and $R_{10}$ are as defined above.

The terms "sulfoxido" or "sulfinyl", as used herein, refers to a moiety that can be represented by the general formula:

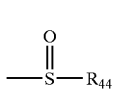

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

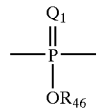

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

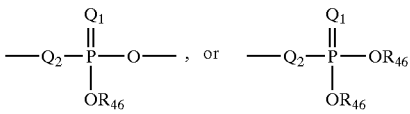

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

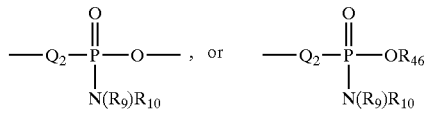

wherein $R_9$ and $R_{10}$ are as defined above, and $Q_2$ represents O, S or N.

A "phosphonamidite" can be represented in the general formula:

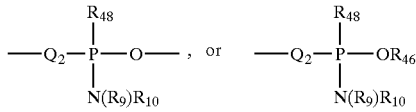

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant (∈) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred polar solvents are DMF, DME, NMP, and acetonitrile.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

A "polar, aprotic solvent" means a polar solvent as defined above which has no available hydrogens to exchange with the compounds of this invention during reaction, for example DMF, acetonitrile, diglyme, DMSO, or THF.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

III. Exemplary Catalyzed Reactions

As described above, one invention of the Applicants' features a transition metal-catalyzed amination reaction which comprises combining an amine with a substrate aryl group bearing an activated group X. The reaction includes at least a catalytic amount of a transition metal catalyst, comprising a novel ligand, and the combination is maintained under conditions appropriate for the metal catalyst to catalyze the arylation of the amine.

The two ligands (24 and 25) shown below are referred to by number in the illustrative embodiments in this section.

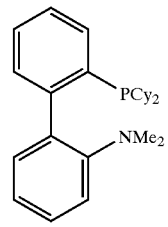

24

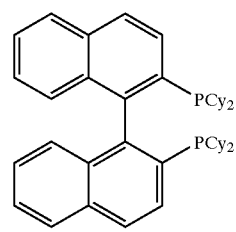

25

In an illustrative embodiment, the subject methods can be used for the intermolecular reaction between an electron-rich aryl chloride and pyrrolidine to give an N-aryl pyrrolidine:

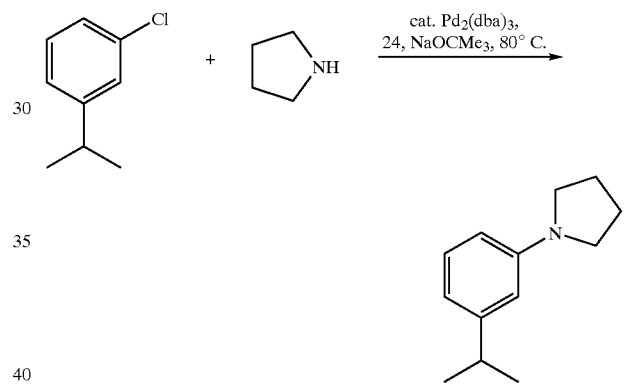

In a second illustrative embodiment, the subject methods can be used to achieve the N-arylation of indole with an electron-rich aryl bromide:

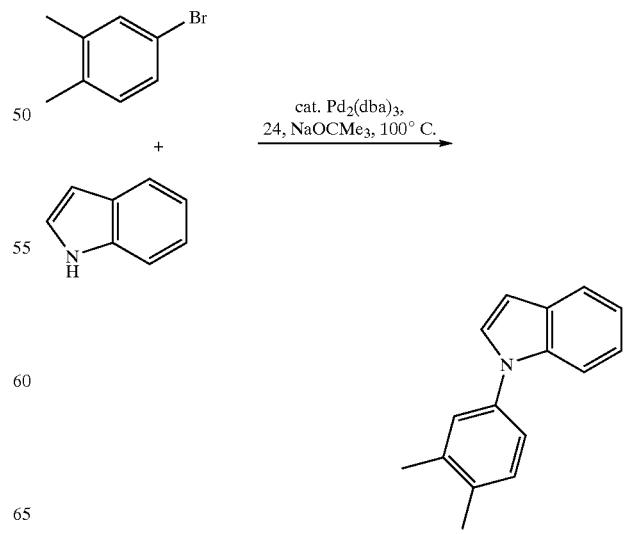

Another aspect of the present invention involves the catalysis by Pd/4 of the amination of electron-poor aryl chlorides, as depicted in the following illustrative transformation.

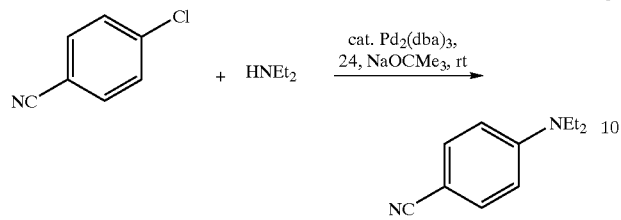

An additional aspect of the present invention centers on the room temperature amination of aryl iodides or bromides, as depicted in the following illustrative transformation involving an aryl iodide.

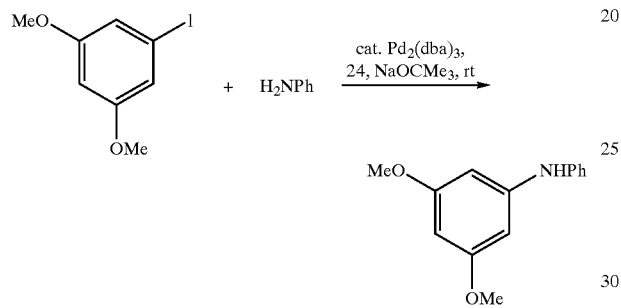

In another illustrative embodiment, the subject methods are exploited in a palladium-catalyzed amination of an electron-neutral aryl chloride.

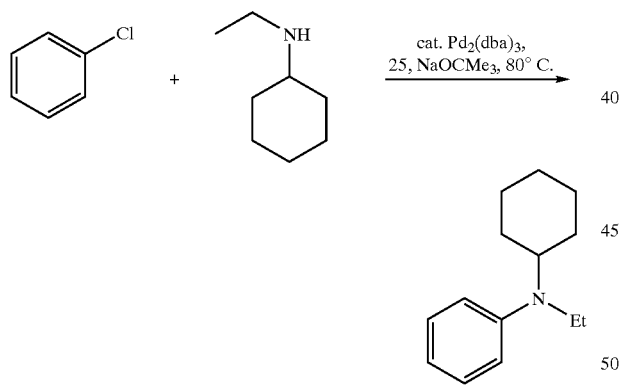

One of ordinary skill in the art will be able to envision intramolecular variants of the subject amination methods. An illustrative embodiment follows:

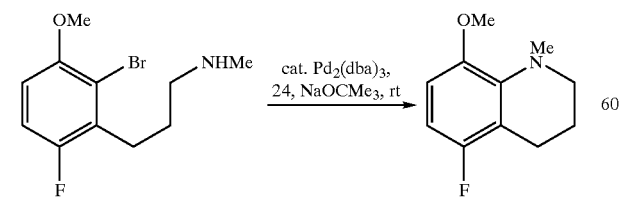

Another aspect of the Applicants' invention features a transition metal-catalyzed Suzuki cross-coupling reaction between an arylboronic acid, arylboronic ester, alkylborane, or the like and a substrate aryl bearing an activated group X. The reaction includes at least a catalytic amount of a transition metal catalyst, comprising a novel ligand, and the combination is maintained under conditions appropriate for the metal catalyst to catalyze the cross-coupling reaction between the boron-containing reactant and the substrate aryl reactant.

In an embodiment illustrative of the Suzuki coupling aspect of the invention, the subject methods may be exploited in the preparation of 3,5-dimethoxybiphenyl, at room temperature, from 1-chloro-3,5-dimethoxybenzene and phenylboronic acid:

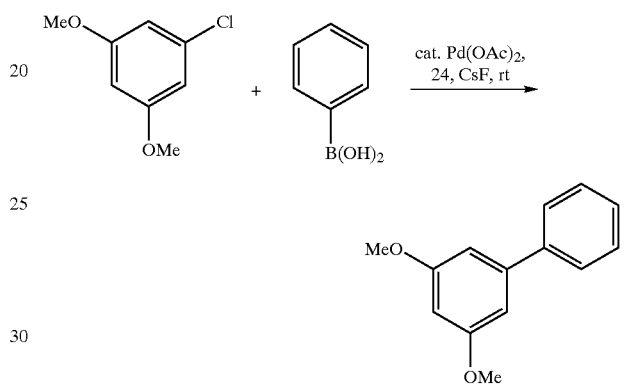

In an second embodiment illustrative of the Suzuki coupling aspect of the invention, the subject methods may be exploited in the formation of a $Sp^2$–$Sp^3$ carbon-carbon bond; an electron-rich aryl chloride reacts with an alkyl borane to give an alkylarene:

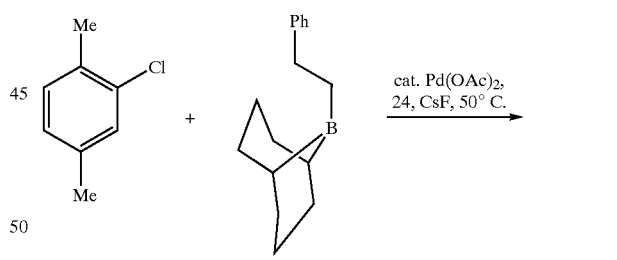

One of ordinary skill in the art will be able to envision intramolecular variants of the subject Suzuki coupling methods. An illustrative embodiment follows:

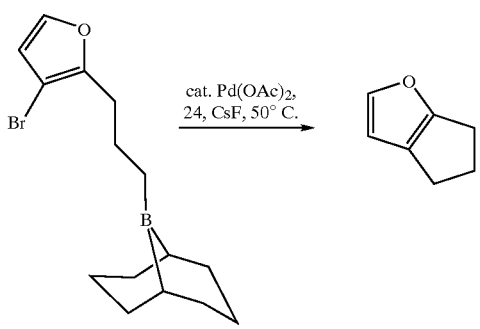

Still another aspect of the Applicants' invention features a transition metal-catalyzed α-arylation of ketones involving the reaction of an enolizable ketone with a substrate aryl bearing an activated group X. The reaction includes at least a catalytic amount of a transition metal catalyst, comprising a novel ligand, and the combination is maintained under conditions appropriate for the metal catalyst to catalyze the α-arylation of the enolizable ketone.

In an embodiment illustrative of the α-arylation aspect of the invention, the subject methods may be exploited in the preparation of 6-methyl-2-(3,4-dimethylphenyl) cyclohexanone, at room temperature, from 1-bromo-3,4-dimethylbenzene and 2-methylcyclohexanone:

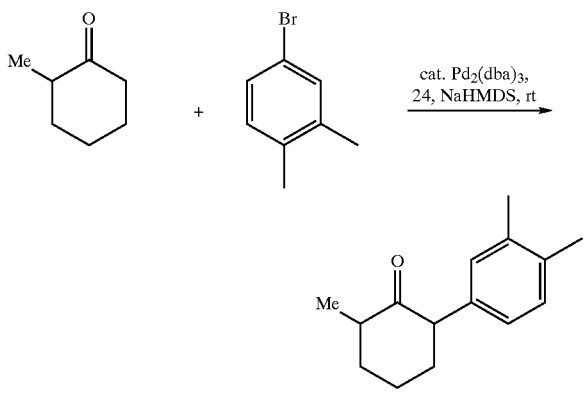

One of ordinary skill in the art will be able to envision intramolecular variants of the subject α-arylation methods. An illustrative embodiment follows:

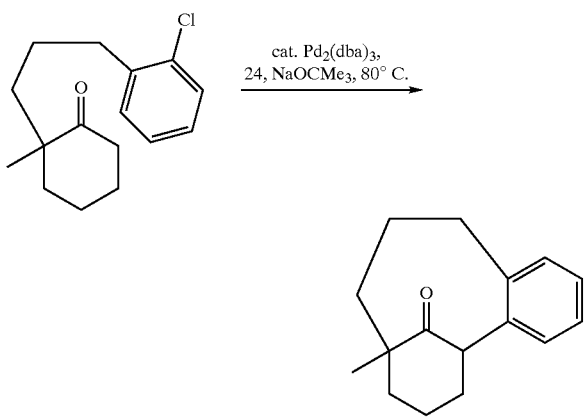

The substrate aryl compounds include compounds derived from simple aromatic rings (single or polycylic) such as benzene, naphthalene, anthracene and phenanthrene; or heteroaromatic rings (single or polycyclic), such as pyrrole, thiophene, thianthrene, furan, pyran, isobenzofuran, chromene, xanthene, phenoxathiin, pyrrole, imidazole, pyrazole, thiazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine and the like. In preferred embodiment, the reactive group, X, is substituted on a five, six or seven membered ring (though it can be part of a larger polycycle).

In preferred embodiments, the aryl substrate may be selected from the group consisting of phenyl and phenyl derivatives, heteroaromatic compounds, polycyclic aromatic and heteroaromatic compounds, and functionalized derivatives thereof. Suitable aromatic compounds derived from simple aromatic rings and heteroaromatic rings, include but are not limited to, pyridine, imidizole, quinoline, furan, pyrrole, thiophene, and the like. Suitable aromatic compounds derived from fused ring systems, include but are not limited to naphthalene, anthracene, tetralin, indole and the like.

Suitable aromatic compounds may have the formula $Z_pArX$, where X is an activated substituent. An activated substituent, X, is characterized as being a good leaving group. In general, the leaving group is a group such as a halide or sulfonate. Suitable activated substituents include, by way of example only, halides such as chloride, bromide and iodide, and sulfonate esters such as triflate, mesylate, nonaflate and tosylate. In certain embodiments, the leaving group is a halide selected from iodine, bromine, and chlorine.

Z represents one or more optional substituents on the aromatic ring, though each occurence of Z (p>1) is independently selected. By way of example only, each incidence of substitution independently can be, as valence and stability permit, a halogen, a lower alkyl, a lower alkenyl, a lower alkynyl, a carbonyl (e.g., an ester, a carboxylate, or a formate), a thiocarbonyl (e.g., a thiolester, a thiolcarboxylate, or a thiolformate), a ketyl, an aldehyde, an amino, an acylamino, an amido, an amidino, a cyano, a nitro, an azido, a sulfonyl, a sulfoxido, a sulfate, a sulfonate, a sulfamoyl, a sulfonamido, a phosphoryl, a phosphonate, a phosphinate, $-(CH_2)_m-R_8$, $-(CH_2)_m-OH$, $-(CH_2)_m-$O-lower alkyl, $-(CH_2)_m-$O-lower alkenyl, $-(CH_2)_m-$O$-(CH_2)_n-R_8$, $-(CH_2)_m-$SH, $-(CH_2)_m-$S-lower alkyl, $-(CH_2)_m-$S-lower alkenyl, $-(CH_2)_m-$S$-(CH_2)_n-R_8$, or protecting groups of the above or a solid or polymeric support; $R_8$ represents a substituted or unsubstituted aryl, aralkyl, cycloalkyl, cycloalkenyl, or heterocycle; and n and m are independently for each occurrence zero or an integer in the range of 1 to 6. P is preferably in the range of 0 to 5. For fused rings, where the number of substitution sites on the aryl group increases, p may be adjusted appropriately.

In certain embodiments, suitable substituents Z include alkyl, aryl, acyl, heteroaryl, amino, carboxylic ester, carboxylic acid, hydrogen, ether, thioether, amide, carboxamide, nitro, phosphonic acid, hydroxyl, sulfonic acid, halide, pseudohalide groups, and substituted derivatives thereof, and p is in the range of 0 to 5. In particular, the reaction is anticipated to be compatible with acetals, amides and silyl ethers. For fused rings, where the number of substitution sites on the aromatic ring increases, p may be adjusted appropriately.

A wide variety of substrate aryl groups are useful in the methods of the present invention. The choice of substrate will depend on factors such as the amine, boronic acid, ketone, or the like to be employed and the desired product, and an appropriate aryl substrate will be made apparent to the skilled artisan by these teachings. It will be understood that the aryl substrate preferably will not contain any interfering functionalities. It will further be understood that not all activated aryl substrates will react with every amine, boronic acid, ketone, or the like.

The reactive the amine, boronic acid, ketone, or the like can be a molecule separate from the substrate aryl group, or a substituent of the same molecule (e.g., for intramolecular variations).

The amine, boronic acid, ketone, or the like is selected to provide the desired reaction product. The amine, boronic acid, ketone, or the like may be functionalized. The amine, boronic acid, ketone, or the like may be selected from a wide variety of structural types, including but not limited to, acyclic, cyclic or heterocyclic compounds, fused ring compounds or phenol derivatives. The aromatic compound and the amine, boronic acid, ketone, or the like may be included as moieties of a single molecule, whereby the arylation reaction proceeds as an intramolecular reaction.

In certain embodiments, the amine, boronic acid, ketone, or the like is generated in situ by conversion of a precursor under the reaction conditions.

In certain embodiments, the aryl substrate and/or the amine, boronic acid, ketone, or the like is attached, either directly or via a tether, to a solid support.

Alternatively, the corresponding salt of the amine, boronic acid, ketone, or the like, may be prepared and used in place of the amine, boronic acid, ketone, or the like. When the corresponding salt of the amine, boronic acid, ketone, or the like is used in the reaction, an additional base may not be required.

The active form of the transition metal catalyst is not well characterized. Therefore, it is contemplated that the "transition metal catalyst" of the present invention, as that term is used herein, shall include any catalytic transition metal and/or catalyst precursor as it is introduced into the reaction vessel and which is, if necessary, converted in situ into the active form, as well as the active form of the catalyst which participates in the reaction.

In preferred embodiments, the transition metal catalyst complex is provided in the reaction mixture is a catalytic amount. In certain embodiments, that amount is in the range of 0.0001 to 20 mol %, and preferably 0.05 to 5 mol %, and most preferably 1–3 mol %, with respect to the limiting reagent, which may be either the aromatic compound the amine, boronic acid, ketone, or the like (or the corresponding salt thereof), depending upon which reagent is in stoichiometric excess. In the instance where the molecular formula of the catalyst complex includes more than one metal, the amount of the catalyst complex used in the reaction may be adjusted accordingly. By way of example, $Pd_2(dba)_3$ has two metal centers; and thus the molar amount of $Pd_2(dba)_3$ used in the reaction may be halved without sacrificing catalytic activity.

Catalysts containing palladium and nickel are preferred. It is expected that these catalysts will perform similarly because they are known to undergo similar reactions, namely oxidative-addition reactions and reductive-elimination reactions, which are thought to be involved in the formation of the products of the present invention. The novel ligands are thought to modify the catalyst performance by, for example, modifying reactivity and preventing undesirable side reactions.

As suitable, the catalysts employed in the subject method involve the use of metals which can mediate cross-coupling of the aryl groups ArX and the amine, boronic acid, ketone, or the like as defined above. In general, any transition metal (e.g., having d electrons) may be used to form the catalyst, e.g., a metal selected from one of Groups 3–12 of the periodic table or from the lanthanide series. However, in preferred embodiments, the metal will be selected from the group of late transition metals, e.g. preferably from Groups 5–12 and even more preferably Groups 7–11. For example, suitable metals include platinum, palladium, iron, nickel, ruthenium and rhodium. The particular form of the metal to be used in the reaction is selected to provide, under the reaction conditions, metal centers which are coordinately unsaturated and not in their highest oxidation state. The metal core of the catalyst should be a zero valent transition metal, such as Pd or Ni with the ability to undergo oxidative addition to Ar—X bond. The zero-valent state, M(0), may be generated in situ, e.g., from M(II).

To further illustrate, suitable transition metal catalysts include soluble or insoluble complexes of platinum, palladium and nickel. Nickel and palladium are particularly preferred and palladium is most preferred. A zero-valent metal center is presumed to participate in the catalytic carbon-heteroatom or carbon-carbon bond forming sequence. Thus, the metal center is desirably in the zero-valent state or is capable of being reduced to metal(0). Suitable soluble palladium complexes include, but are not limited to, tris(dibenzylideneacetone) dipalladium [$Pd_2(dba)_3$], bis(dibenzylideneacetone) palladium [$Pd(dba)_2$] and palladium acetate. Alternatively, particularly for nickel catalysts, the active species for the oxidative-addition step may be in the metal (+1) oxidation state.

Catalysts containing palladium and nickel are preferred. It is expected that these catalysts will perform comparably because they are known in the art to undergo similar reactions, namely cross-coupling reactions, which may be involved in the formation of the products of the present invention, e.g., arylamines, diaryls, α-arylketones, or the like.

The coupling can be catalyzed by a palladium catalyst which palladium may be provided in the form of, for illustrative purposes only, Pd/C, $PdCl_2$, $Pd(OAc)_2$, $(CH_3CN)_2PdCl_2$, $Pd[P(C_6H_5)_3]_4$, and polymer supported Pd(0). In other embodiments, the reaction can be catalyzed by a nickel catalyst which nickel may be provided in the form of, for illustrative purposes only, $Ni(acac)_2$, $NiCl_2[P(C_6H_5)]_2$, Ni(1, 5-cyclooctadiene)$_2$, Ni(1,10-phenanthroline)$_2$, Ni(dppf)$_2$, $NiCl_2$(dppf), $NiCl_2$(1,10-phenanthroline), Raney nickel and the like, wherein "acac" represents acetylacetonate.

The catalyst will preferably be provided in the reaction mixture as metal-ligand complex comprising a bound supporting ligand, that is, a metal-supporting ligand complex.

The ligand effects can be key to favoring, inter alia, the reductive elimination pathway or the like which produces the products, rather than side reactions such as β-hydride elimination. In preferred embodiments, the subject reaction employs bidentate ligands such as bisphosphines or aminophosphines. The ligand, if chiral can be provided as a racemic mixture or a purified stereoisomer. In certain instances, e.g. the improved method for the synthesis of aryl amines, the use of a racemic, chelating ligand is preferred.

The ligand, as described in greater detail below, may be a chelating ligand, such as by way of example only, alkyl and aryl derivatives of phosphines and bisphosphines, amines, diamines, imines, arsines, and hybrids thereof, including hybrids of phosphines with amines. Weakly or non-nucleophilic stabilizing ions are preferred to avoid undesired side reactions involving the counter ion. The catalyst complex may include additional ligands as required to obtain a stable complex. Moreover, the ligand can be added to the reaction mixture in the form of a metal complex, or added as a separate reagent relative to the addition of the metal.

The supporting ligand may be added to the reaction solution as a separate compound or it may be complexed to the metal center to form a metal-supporting ligand complex prior to its introduction into the reaction solution. Supporting ligands are compounds added to the reaction solution which are capable of binding to the catalytic metal center. In some preferred embodiments, the supporting ligand is a chelating ligand. Although not bound by any theory of operation, it is hypothesized that the supporting ligands suppress unwanted side reactions as well as enhance the rate and efficiency of the desired processes. Additionally, they typically prevent precipitation of the catalytic transition metal. Although the present invention does not require the formation of a metal-supporting ligand complex, such complexes have been shown to be consistent with the postulate that they are intermediates in these reactions and it has been observed the selection of the supporting ligand has an affect on the course of the reaction.

The supporting ligand is present in the range of 0.0001 to 40 mol % relative to the limiting reagent, i.e., amine, boronic acid, ketone or the like, or aromatic compound. The ratio of the supporting ligand to catalyst complex is typically in the range of about 1 to 20, and preferably in the range of about 1 to 4 and most preferably 2. These ratios are based upon a single metal complex and a single binding site ligand. In instances where the ligand contains additional binding sites (i.e., a chelating ligand) or the catalyst contains more than one metal, the ratio is adjusted accordingly. By way of example only, the supporting ligand BINAP contains two coordinating phosphorus atoms and thus the ratio of BINAP to catalyst is adjusted downward to about 1 to 10, preferably about 1 to 2 and most preferably 1. Conversely, $Pd_2(dba)_3$ contains two palladium metal centers and the ratio of a non-chelating ligand to $Pd_2(dba)_3$ is adjusted upward to 1 to 40, preferably 1 to 8 and most preferably 4.

In certain embodiments of the subject method, the transition metal catalyst includes one or more phosphine or aminophosphine ligands, e.g., as a Lewis basic ligand that controls the stability and electron transfer properties of the transition metal catalyst, and/or stabilizes the metal intermediates. Phosphine ligands are commercially available or can be prepared by methods similar to known processes. The phosphines can be monodentate phosphine ligands, such as trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, in particular triphenylphosphine, tri(o-tolyl)phosphine, triisopropylphosphine or tricyclohexylphosphine; or a bidentate phosphine ligand such as 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutyl-phosphino)ethane, 1,2-bis(dicyclohexylphosphino)ethane, 1,3-bis(dicyclohexylphosphino)propane, 1,3-bis(diiso-propylphosphino)propane, 1,4-bis(diisopropylphosphino)-butane and 2,4-bis(dicyclohexylphosphino)pentane. The aminophosphines may be monodentate, e.g. each molecule of aminophosphine donates to the catalytic metal atom only a Lewis basic nitrogen atom or a Lewis basic phosphorus atom. Alternatively, the aminophosphine may be a chelating ligand, e.g. capable of donating to the catalytic metal atom both a Lewis basic nitrogen atom and a Lewis basic phosphorus atom.

In some instances, it may be necessary to include additional reagents in the reaction mixture to promote reactivity of either the transition metal catalyst or activated aryl nucleus. In particular, it may be advantageous to include a suitable base. In general, a variety of bases may be used in practice of the present invention. It has not been determined at which point(s) in the mechanisms of the subject transformations the base participates. The base may optionally be sterically hindered to discourage metal coordination of the base in those circumstances where such coordination is possible, i.e., alkali metal alkoxides. Exemplary bases include such as, by way of example only: alkoxides such as sodium tert-butoxide; alkali metal amides such as sodium amide, lithium diisopropylamide, and alkali metal bis(trialkylsilyl)amide, e.g., such as lithium bis(trimethylsilyl)amide (LiHMDS) or sodium bis(trimethylsilyl)amide (NaHMDS); tertiary amines (e.g. triethylamine, trimethylamine, 4-(dimethylamino)pyridine (DMAP), 1,5-diazabicycl[4.3.0]non-5-ene (DBN), 1,5-diazabicyclo[5.4.0] undec-5-ene (DBU); alkali or alkaline earth carbonate, bicarbonate or hydroxide (e.g. sodium, magnesium, calcium, barium, potassium carbonate, phosphate, hydroxide and bicarbonate). By way of example only, suitable bases include NaH, LiH, KH, $K_2CO_3$, $Na_2CO_3$, $Tl_2CO_3$, $Cs_2CO_3$, K(OtBu), Li(OtBu), Na(OtBu) K(OAr), Na(OAr), and triethylamine, or mixtures thereof. Preferred bases include CsF, $K_3PO_4$, DBU, NaOt-Bu, KOt-Bu, $LiN(i-Pr)_2$ (LDA), $KN(SiMe_3)_2$, $NaN(SiMe_3)_2$, and $LiN(SiMe_3)_2$.

Base is used in approximately stoichiometric proportions in the subject methods. The present invention has demonstrated that there is no need for large excesses of base in order to obtain good yields of the desired products under mild reaction conditions. No more than four equivalents of base, and preferably no more than two equivalents, are needed. Furthermore, in reactions using the corresponding salt of an amine, boronic acid, ketone or the like, additional base may not be required.

As is clear from the above discussion, the products which may be produced by the amination, Suzuki coupling, and α-arylation reactions of this invention can undergo further reaction(s) to afford desired derivatives thereof. Such permissible derivatization reactions can be carried out in accordance with conventional procedures known in the art. For example, potential derivatization reactions include esterification, oxidation of alcohols to aldehydes and acids, N-alkylation of amides, nitrite reduction, acylation of alcohols by esters, acylation of amines and the like.

IV. Reaction Conditions

The reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely affect the reactants, the catalyst, or the product. For example, the reaction temperature influences the speed of the reaction, as well as the stability of the reactants and catalyst. The reactions will usually be run at temperatures in the range of 25° C. to 300° C., more preferably in the range 25° C. to 150° C.

In general, the subject reactions are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase with one of the reactants anchored to a solid support.

In certain embodiments it is preferable to perform the reactions under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion. In a order of events that, in some cases, can lead to an enhancement of the reaction rate, the base, e.g. t-BuONa, is the last ingredient to be added to the reaction mixture.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the metal catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, one or more of the reactants can be immobilized or incorporated into a polymer or other insoluble matrix by, for example, derivativation with one or more of substituents of the aryl group.

V. Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (I1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, $_D$-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention may be understood with reference to the following examples, which are presented for illustrative purposes only and which are non-limiting. The substrates utilized in these examples were either commercially available, or were prepared from commercially available reagents.

EXAMPLE 1

A Highly Active Catalyst for Palladium-Catalyzed Cross-Coupling Reactions: Room Temperature Suzuki Couplings and Amination of Unactivated Aryl Chlorides A highly active palladium catalyst which employs the chelating aminophosphine ligand 1-(N,N-dimethylamino)-1'-(dicyclohexylphosphino)biphenyl (2) has been developed. This catalyst is effective for the cross-coupling of aryl chlorides with amines, boronic acids, and ketone enolates. The system is sufficiently reactive to allow for the room temperature amination of aryl bromides and electron-deficient aryl chlorides, and promotes room temperature Suzuki coupling reactions of both electron-rich and electron-deficient aryl chlorides. The coordination of the amine moiety may be key to the enhanced reactivity and catalyst stability of this system.

Palladium-catalyzed C—N bond-forming reactions have evolved into a versatile and efficient synthetic transformation. The use of palladium catalysts supported by bidentate phosphine ligands has made possible substitution of aryl halides and triflates with nitrogen,[1] oxygen,[2] and certain carbon nucleophiles.[3] The lack of a general palladium-based catalyst for aryl chloride substitution reactions,[4,5] as well as the elevated reaction temperatures often required prompted us to search for new ligands which might overcome these limitations.

$^1$H NMR studies in our laboratories of the amination reactions of aryl bromides catalyzed by BINAP/Pd(OAc)$_2$ suggested that oxidative addition was rate limiting.[6] For aryl chlorides, oxidative addition can be anticipated to be even more sluggish. To facilitate this slow step, we began to explore the use of electron-rich phosphine ligands.[4, 5d, 7a] An initial experiment which employed PCy$_3$ as the palladium-supporting ligand demonstrated that although this type of catalyst was capable of activating the carbon-chlorine bond, the process suffered from facile β-hydride elimination and subsequent formation of reduced arene.[5a] Based on our knowledge that bidentate ligands suppressed β-hydride elimination in arylations of primary amines,[1c] we focused our efforts on the preparation of electron-rich bidentate phosphines.[6] We first prepared the known 1,1'-bis (dicyclohexylphosphino)binaphthyl (1).[8] Initial screening demonstrated that 1/Pd(0) constituted a reasonably effective catalyst for the coupling of pyrrolidine with chlorotoluene. This important result, taken together with our experience with bidentate monophosphines PPF—OMe and PPFA[1d] prompted us to prepare aminophosphine ligand 2.[9] In comparison to 1, use of ligand 2 is generally superior and significantly expands the scope of palladium-catalyzed aryl chloride transformations. Herein, we demonstrate that the 2/Pd(0) catalyst system is highly active and allows for the room temperature amination of aryl bromides and the first example of a room temperature amination of an aryl chloride. Moreover, this system functions as the first general catalyst for room temperature Suzuki coupling reactions of aryl chlorides.

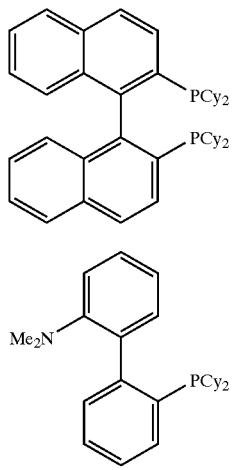

To demonstrate the efficacy of the 2/Pd(0) catalyst system, we have prepared several aniline derivatives from aryl chlorides (Table 1, entries 1–2,4–6, 8–9, 13, 16). Secondary amines give excellent results in the coupling procedure (Table 1, entries 1–2, 4–6, 8–9), and the arylation of a primary aniline can also be accomplished (Table 1, entry 16). Primary alkyl amines are efficient coupling partners provided the aryl chloride is substituted at the ortho position (Table 1, entry 13), or through the use of ligand 1 (Table 1, entries 14,17). Catalyst levels as low as 0.05 mol % Pd have been achieved in the reaction of chlorotoluene with di-n-butylamine (Table 1, entry 1).

Given the high reactivity of this catalyst, we explored the possibility of carrying out room temperature aminations. We found that both aryl iodides and aryl bromides (Table 1, entries 3, 7, 10, 15) reacted readily at room temperature when DME was employed as the solvent. The experimentally simple procedure did not require crown ether or other additives.[1e] Broadly speaking, the room temperature amination of aryl bromides displays the same scope as the reactions of aryl chlorides at 80° C. Aryl bromides containing functional groups sensitive to NaOt-Bu could be converted to the corresponding aniline derivative by using $K_3PO_4$ as the base. In these reactions (Table 1, entries 11 and 12), heating at 80° C. was required due to the decreased basicity and/or solubility of $K_3PO_4$.

Using 2/Pd(0) the first amination of an aryl chloride (albeit an activated one) at room temperature could also be achieved for the first time.[10] Thus, the coupling of p-chlorobenzonitrile and morpholine was catalyzed by 2.5 mol % $Pd_2(dba)_3$, 7.5 mol % 2 and NaOt-Bu in DME at room temperature to provide the corresponding aniline derivative in 96% yield (Table 1, entry 9).

TABLE 1

Catalytic Amination[a] of Aryl Chlorides and Bromides

R—C6H4—X + HN(R)R′ → (cat. $Pd_2(dba)_3$/Ligand 2, NaOtBu, toluene, rt–100° C.) → R—C6H4—N(R)R′

1: R = 4-Me, X = Cl; 95%
2: R = 4-MeO, X = Cl; 90%
3: R = 4-Me, X = Br; 96%[b, c, k]

4: R = 4-Me, X = Cl; 98%
5: R = 4-MeO, X = Cl; 95%
6: R = 2,5-Me$_2$, X = Cl; 96%
7: R = 4-Me, X = Br; 95%[b, l]

8: R = 4-MeO, X = Cl; 91%
9: R = 4-CN, X = Cl; 96%[b, d, k]
10: R = 2,5-Me$_2$, X = Br; 97%[b, c, l]
11: R = 4-CO$_2$Me, X = Br; 81%[e]
12: R = 4-C(O)Me, X = Br 82%[f, g]

TABLE 1-continued

Catalytic Amination[a] of Aryl Chlorides and Bromides

R—C₆H₄—X + HN(R)R' →[cat. Pd₂(dba)₃/Ligand 2][NaOtBu, toluene, rt–100° C.] R—C₆H₄—N(R)R'

13: R = 2,5-Me₂, X = Cl; 99%  
14: R = 4-CO₂Me, X = Cl; 83%[h,i]  
16: X = Cl, 93%[h]  
17: X = Cl, 89%[j,m]

15: R = 2,6-Me₂, X = Br; 88%[b, d, k]

☐ = Reaction run at rt.

[a]Reaction Conditions: 1.0 equiv. aryl halide, 1.2 equiv. amine, 1.4 equiv. NaOtBu, 0.5 mol % Pd₂(dba)₃, 1.5 mol % ligand (1.5 L/Pd), toluene (2 mL/mmol halide), 80° C. Reactions were complete in 11–27 h; reaction times have not been minimized.
[b]Reaction run at room temperature in DME solvent.
[c]Reaction run with 1.5 mol % Pd₂(dba)₃.
[d]Reaction run with 2.5 mol % Pd₂(dba)₃.
[e]Reaction run using $K_3PO_4$, DME solvent
[f]Reaction run using Pd(OAc)₂, $K_3PO_4$, DME solvent
[g]One of two runs only proceeded to 98% conversion.
[h]Reaction run at 100° C.
[i]Reaction run with Pd(OAc)₂, ligand 1, $Cs_2CO_3$ as catalyst, ligand, and base.
[j]Using1 as ligand.
[k][ArBr] = 1 M.
[l][ArBr] = 2M.
[m]1.5 equiv. benzylamine used In light of the high reactivity of this new catalyst system in amination reactions, we proceeded to examine its utility in several different Pd-catalyzed C—C bond forming reactions. Pd-catalyzed Suzuki coupling reactions[11] which use aryl chlorides as substrates generally require fairly high reaction temperatures (>90° C.), and are usually inefficient if the aryl halide does not contain electron-withdrawing substituents.[7] While nickel catalysts are more efficient at promoting Suzuki coupling reactions of electronically-neutral or electron-rich aryl chlorides, sterically hindered substrates are often problematic due to the small size of nickel relative to palladium.[12] Furthermore, examples of Suzuki coupling reactions which proceed at room temperature are rare,[13] and often require stoichiometric amounts of highly toxic thallium hydroxide.[13b,c,d] To the best of our knowledge, no examples of room temperature Suzuki couplings of an aryl chloride have been reported.

We have found that Suzuki coupling reactions of both aryl bromides and aryl chlorides proceed in high yield at room temperature using the 2/Pd(0) catalyst system and CsF[14] in dioxane solvent (Table 2, entries 2,5,7–10).[15,16] These conditions allow for the coupling of both electron-rich and electron-deficient aryl chlorides, and tolerate the presence of base-sensitive functional groups. An aryl-alkyl coupling reaction of an aryl chloride using an alkylboron reagent generated in situ from 1-hexene and 9-BBN[17] was achieved at 50° C.; the higher temperature presumably being necessary due to the increased size of the boron reagent and the slower rate of transmetallation of alkyl groups relative to aryl groups.[17] Suzuki coupling reactions of electron-rich aryl chlorides could also be carried out using inexpensive $K_3PO_4$ with only 0.5 mol % palladium catalyst, although temperatures of 100° C. were required.

We also found the 2/Pd(0) catalyst system was effective for the Pd-catalyzed α-arylation of ketones.[3] Coupling of 5-bromo-m-xylene with 2-methyl-3-pentanone was performed at room temperature using NaHMDS as base (Table 2, entry 12). Interestingly, while the BINAP catalyst system was selective at promoting the monoarylation of methyl ketones, 2/Pd was selective for the diarylation of methyl ketones (Table 2, entry 11). This may be due to the decreased steric bulk of the dimethylamine portion of 2 relative to the diphenylphosphine group of BINAP.

Other Pd-catalyzed cross couplings of aryl chlorides were surveyed using this catalyst. Stille couplings,[18] Sonogashira couplings,[19] and cross-couplings of aryl halides with organozinc reagents gave no detectable products.[20] The Heck arylation[21] of styrene gave some conversion to product at 110° C.

TABLE 2

Suzuki Coupling[a] and Ketone Arylation

| Entry | Halide | Coupling Partner | Temp | mol % Pd | Yield | Product |
|---|---|---|---|---|---|---|
| 1 | Me—C₆H₄—Cl | PhB(OH)₂ | 100 | 0.5 | 96[b] | Me—C₆H₄—Ph |
| 2 | Me—C₆H₄—Cl | | rt | 2.0 | 94 | Me—C₆H₄—Ph |

TABLE 2-continued

Suzuki Coupling[a] and Ketone Arylation

| Entry | Halide | Coupling Partner | Temp | mol % Pd | Yield | Product |
|---|---|---|---|---|---|---|
| 3 | | o-MeOPhB(OH)$_2$ | 100 | 1.0 | 94[d] | 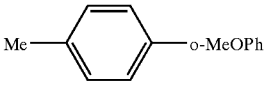 |
| 4 | 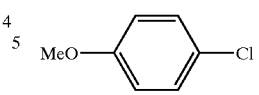 | PhB(OH)$_2$ | 100 | 0.5 | 93[b] |  |
| 5 | | | rt | 2.0 | 92 | |
| 6 | |  | 50 | 2.0 | 88[c] | 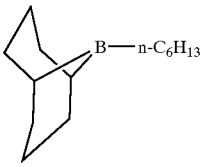 |
| 7 | 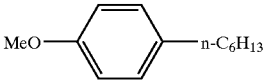 | PhB(OH)$_2$ | rt | 1.0 | 92 | 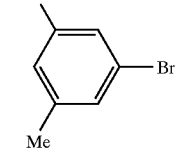 |
| 8 | 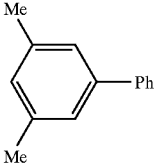 | m-TolB(OH)$_2$ | rt | 2.0 | 94 | 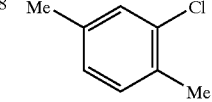 |
| 9 | 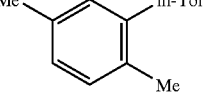 | PhB(OH)$_2$ | rt | 2.0 | 90 | 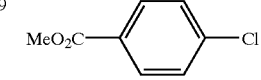 |
| 10 | 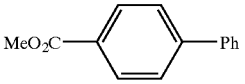 | m-TolB(OH)2 | rt | 2.0 | 92 | 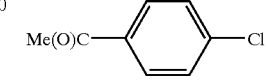 |
| 11 |  | 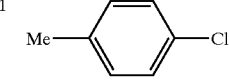 | 80 | 3.0 | 79[d] | 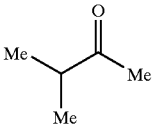 |
| 12 | 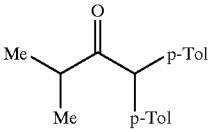 | 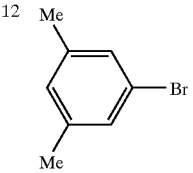 | rt | 3.0 | 82[e] | 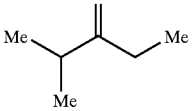 |

[a]Reaction Conditions: 1.0 equiv. aryl halide, 1.5 equiv. boron reagent, 3.0 equiv. CsF, 0.5–2.0 mol % Pd(OAc)$_2$, 0.75–3.0 mol % 2 (1.5 L/Pd), dioxane (3 mL/mmol halide). Reactions were complete in 19–30h; reaction times have not been minimized.
[b]2.0 equiv. K$_3$PO$_4$ used in place of CsF.
[c]One of two runs only proceeded to 98% conversion.
[d]Pd$_2$(dba)$_3$, NaOtBu used as catalyst, base.
[e]Pd$_2$(dba)$_3$, NaHMDS used as catalyst, base While the precise mechanistic details of the reactions promoted by the 2/Pd(0) catalyst system remain unknown, we believe that the overall catalytic cycle for the amination reaction is similar to that postulated for the BINAP/Pd catalyzed amination of aryl bromides.[1c] However, in reactions catalyzed by 2/Pd there may be different pathways available for the amine coordination/deprotonation step. Our current view is a pathway which involves binding of the amine to four-coordinate complex I, followed by deprotonation of the resulting five-coordinate complex II to give III (FIG. 1, path A). Alternatively, coordination of the amine substrate may occur after initial dissociation of the dimethylamino moiety of the ligand, followed by nucleophilic attack of the amine substrate on three-coordinate[22b] complex IV to give V. Deprotonation of V is followed by rapid recomplexation of the ligand amine group to give III (FIG. 1, path B).[22] If path B is operative, the recomplexation of the amine is presumably fast relative to β-hydride elimination since little or no reduced side product is observed. This notion is supported by the fact that Cy$_2$PPh was not an effective ligand for any of these Pd-catalyzed processes;[15,16] amination reactions conducted with electron-rich monodentate phosphines as ligands such as Cy$_3$P or Cy$_2$PPh demonstrated that reduction via β-hydride elimination can be a significant problem without a chelating group on the ligand. The relatively small size of the amine group in 2 allows for the efficient coupling of both cyclic and acyclic secondary amines.[1d] That 2/Pd(0) can be employed in an amination procedure at the 0.05 mol % level (Table 1, entry 1) suggests that the dimethylamino group also contributes to the stability of the catalyst.

FIG. 1

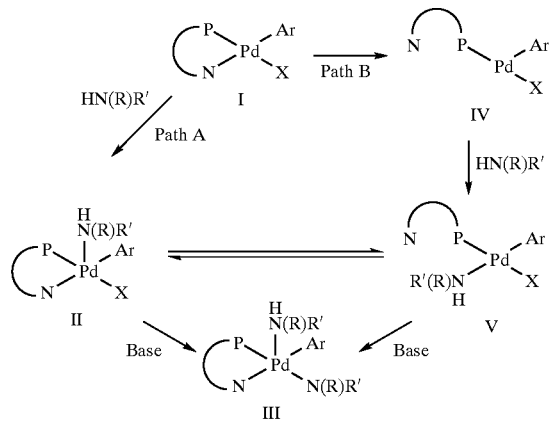

The failure of the 2/Pd(0) catalyst system to promote the Heck, Stille, Sonogashira, and zinc cross-coupling reactions suggests the C—C bond forming reactions discussed in this paper proceed through four-coordinate intermediates with both the amine and phosphine moieties bound to the metal during the key steps in the catalytic cycle. If the ligand is bound in a bidentate fashion, transmetallation from Sn, Cu or Zn, or olefin coordination would be slow.[21,23] This argument is supported by the fact that Suzuki couplings and ketone arylation reactions are generally efficient with chelating phosphine ligands, while Stille reactions are not. Although in some cases Heck reactions are efficient with chelating ligands, these are usually with cationic complexes or for intramolecular reactions.[21]

We hope that modification of the design of this ligand or further optimization of reaction conditions may lead to efficient Heck olefinations of electron-rich aryl chlorides.[24] Further studies towards development of highly active catalysts for these and other processes are currently underway.

References and Notes for Example 1

(1) (a) Guram, A. S.; Rennels, R. A.; Buchwald, S. L. *Angew. Chem. Int. Ed. Engl.* 1995, 34, 1348–1349; (b) Wolfe, J. P.; Rennels, R. A.; Buchwald, S. L. *Tetrahedron* 1996, 52, 7525–7546. (c) Wolfe, J. P.; Wagaw, S.; Buchwald, S. L. *J. Am. Chem. Soc.* 1996, 118, 7215–7216; (d) Marcoux, J. -F.; Wagaw, S.; Buchwald, S. L. *J. Org. Chem.* 1997, 62, 1568–1569; (e) Wolfe, J. P.; Buchwald, S. L. *J. Org. Chem.* 1997, 62, 6066–6068. (f) Wolfe, J. P.; Wagaw, S.; Marcoux, J. -F.; Buchwald, S. L. *Acc. Chem. Res.* Submitted for publication; (g) Louie, J.; Hartwig, J. *Tetrahedron Lett.* 1995, 36, 3609–3612; (h) Driver, M. S.; Hartwig, J. F. *J. Am. Chem. Soc.* 1996, 118, 7217–7218; (i) Baranano, D.; Mann, G.; Hartwig, J. F. *Cur. Org. Chem.* 1997, 1, 287–305. (j) Hartwig, J. F. *Synlett* 1997, 329–340.

(2) (a) Palucki, M.; Wolfe, J. P.; Buchwald, S. L. *J. Am. Chem. Soc.* 1996, 118, 10333–10334; (b) Palucki, M.; Wolfe, J. P.; Buchwald, S. L. *J. Am. Chem. Soc.* 1997, 119, 3395–3396; (d) Mann, G.; Hartwig, J. F. *J. Am. Chem. Soc.* 1996, 118, 13109–13110; (e) Mann, G.; Hartwig, J. F. *J. Org. Chem.* 1997, 62, 5413–5418.

(3) (a) Palucki, M.; Buchwald. S. L. *J. Am. Chem. Soc.* 1997, 119, 11108–11109; (b) Åhman, J.; Wolfe, J. P.; Troutman, M. V.; Palucki, M.; Buchwald, S. L. *J. Am. Chem. Soc.* 1998, 120, 1918; (c) Hamann, B. C.; Hartwig, J. F. *J. Am. Chem. Soc.* 1997, 119, 12382–12383; (d) Satoh, T.; Kawamura, Y.; Miura, M.; Nomura, M. *Angew. Chem. Int. Ed. Engl.,* 1997, 46, 1740–1742.

(4) Aryl chlorides are attractive starting materials from the perspective of cost and availability, but are less reactive than aryl bromides and iodides. See: Grushin, V. V.; Alper, H. *Chem. Rev.* 1994, 94, 1047–1062.

(5) Existing protocols for the amination of aryl chlorides include our work in nickel catalysis as well as two palladium-based methods. Our nickel-based work, while quite effective for a wide variety of aryl chloride substrates, is not effective for amination of other aryl halides and does not tolerate base-sensitive functional groups. The palladium methods are quite limited in scope and often result in mixtures of products. See: (a) Wolfe, J. P.; Buchwald, S. L; *J. Am. Chem. Soc.* 1997, 119, 6054–6058; (b) Beller, M.; Riermeier, T. H.; Reisinger, C. -P.; Herrmann, W. A. *Tetrahedon Lett.* 1997, 38, 2073–2074; (c) Riermeier, T. H.; Zapf, A.; Beller, M. *Top. Catal.* 1997, 4, 301–309; (d) Reddy, N. P.; Tanaka, M. *Tetrahedon Lett.* 1997, 38, 4807–4810. (e) Nishiyama, M.; Yamamoto, T.; Koie, Y. *Tetrahedron Lett.* 1998, 39, 617–620; (f) Yamamoto, T.; Nishiyama, M.; Koie, Y. *Tetrahedron Lett.* 1998, 39, 2367–2370.

(6) Hartwig and Hamann have recently reported similar NMR experiments. They have also shown that electron-rich bidentate bis-phosphines can be used for the Pd-catalyzed amination of aryl chlorides: Hartwig, J. F.; Hamann, B. C. Submitted for Publication.

(7) (a) Shen, W. *Tetrahedron Lett.* 1997, 38, 5575–5578. (b) Beller, M.; Fischer, H.; Herrmann, W. A.; Öfele, K.; Brossmer, C. *Angew. Chem. Int. Ed. Engl.* 1995, 34, 1848–1849.

(8) Zhang, X.; Mashima, K.; Koyano, K.; Sayo, N.; Kumobayashi, H.; Akutagawa, S.; Takaya, H. *J. Chem. Soc. Perkin Trans. I* 1994, 2309–2322.

(9) Ligand 2 was prepared in 3 steps from N,N-dimethyl-2-bromoaniline. The ligand is obtained as a crystalline solid and is stored and handled in the air without any special precautions. Under these conditions, the ligand is stable for at least a month without any detectable oxidation. See supporting information for complete experimental details.

(10) Control experiments conducted in the absence of palladium afforded no coupled products after 24 h at room temperature.

(11) Suzuki, A. in *Metal-Catalyzed Cross-Coupling Reactions* Diederich, F.; Stang, P. J. Eds., Wiley-VCH, Weinheim, Germany, 1998, Ch. 2. (c) Bumagin, N. A.;

Bykov. V. V. *Tetrahedron* 1997, 53, 14437–14450. (d) Mitchell, M. B.; Wallbank, P. J. *Tetrahedron Lett.* 1991, 32, 2273–2276. (e) Firooznia, F.; Gude, C.; Chan, K.; Satoh, Y. *Tetrahedron Lett.* 1998, 39, 3985–3988. (f) Cornils, B. *Orgn. Proc. Res. Dev.* 1998, 2, 121–127.

(12) (a) Indolese, A. F. *Tetrahedron Lett.* 1997, 38, 3513–3516. (b) Saito, S.; Oh-tani, S.; Miyaura, N. *J. Org. Chem.* 1997, 62, 8024–8030.

(13) (a) Campi, E. M.; Jackson, W. R.; Marcuccio, S. M.; Naeslund, C. G. M *J. Chem. Soc., Chem. Commun.* 1994, 2395. (b) Anderson, J. C.; Namli, H.; Roberts, C. A. *Tetrahedron* 1997, 53, 15123–15134. (c) Anderson, J. C.; Namli, H. *Synlett* 1995, 765–766. (d) Uenishi, J. -i.; Beau, J. -M.; Armstrong, R. W.; Kishi, Y. *J. Am. Chem. Soc.* 1987, 109, 4756–4758.

(14) Wright, S. W.; Hageman, D. L.; McClure, L. D. *J. Org. Chem.* 1994, 59, 6095–6097.

(15) See supporting information for complete experimental details.

(16) Control experiments conducted using dicyclohexylphenylphosphine in place of 2 gave low conversions and low yields of products.[15]

(17) Miyaura, N.; Ishiyama, T.; Sasaki, H.; Ishikawa, M.; Satoh, M.; Suzuki, A. *J. Am. Chem. Soc.* 1989, 111, 314–321.

(18) Stille, J. K. *Angew. Chem. Int. Ed. Engl.* 1986, 25, 508.

(19) Sonogashira, K. in ref 11, Ch 5.

(20) Knochel, P. in ref 11, Ch 9.

(21) (a) de Meijere, A.; Meyer, F. E. *Angew. Chem. Int. Ed. Engl.* 1994, 33, 2379–2411; (b) Bräse, S.; de Meijere, A. in ref. 11, Ch. 3.

(22) (a) It is also possible that reductive elimination occurs from a 3-coordinate intermediate[1j] formed by deprotonation of V. (b) There is precedent for the dissociation of one phosphine of a chelating bis-phosphine.[1j] (c) In reactions which employ NaOt-Bu as base it is possible that complexes shown in FIG. 1 may contain X=OtBu.[2d] In reactions which employ $Cs_2CO_3$ or $K_3PO_4$ as base it is unlikely that carbonate or phosphate complexes form due to the low solubility and low nucleophilicity of $Cs_2CO_3$ and $K_3PO_4$ relative to NaOt-Bu.

(23) Farina, V. *Pure Appl. Chem.* 1996, 68, 73–78.

(24) Heck reactions of aryl chlorides generally require high reaction temperatures, and are often inefficient for electron-rich aryl chlorides. See ref 5a and references therein. (a) Herrmann, W. A.; Brossmer, C.; Reisinger, C. -P.; Riermeier, T. H.; Öfele, K.; Beller, M. *Chem. Eur. J* 1997, 3, 1357–1364. (b) Reetz, M. T.; Lohmer, G.; Schwickardi, R. *Angew. Chem. Int. Ed. Engl.* 1998, 37, 481–483. (c) Ohff, M.; Ohff, A.; van der Boom, M. E.; Milstein, D. *J. Am. Chem. Soc.* 1997, 119, 11687–11688.

Supporting Information for Example 1

General. All reactions were carried out under an argon atmosphere in oven-dried glassware. Elemental analyses were performed by E & R Microanalytical Laboratory Inc., Parsippany, N.J. Toluene was distilled under nitrogen from molten sodium. THF was distilled under argon from sodium benzophenone ketyl. Unless stated otherwise, commercially obtained materials were used without purification. Aryl halides were purchased from Aldrich Chemical company except for 4-chloroacetophenone which was purchased from Fluka Chemical company. N,N-dimethyl-2-bromoaniline[1] was prepared by alkylation of 2-bromoaniline with iodomethane in DMF in the presence of sodium carbonate. Tribasic potassium phosphate was purchased from Fluka Chemical company. Cesium fluoride was purchased from Strem Chemical company and was ground with a mortar and pestle before use. Cesium carbonate was obtained from Chemetal and was ground with a mortar and pestle before use. Phenylboronic acid, chlorodicyclohexylphosphine, palladium acetate, tris(dibenzylideneacetone)dipalladium(0), (±)-2,2'-dibromo-1,1'-binaphthyl, and n-butyllithium were purchased from Strem Chemical company. 2-Methoxyphenylboronic acid[2] and 3-methylphenylboronic acid[2] were prepared by lithiation of the corresponding halide and reaction with $B(OMe)_3$ according to a general literature procedure.[2] These boronic acids were obtained in ~85–95% purity following crystallization from pentane/ether and were used without further purification. Trimethyl borate, triisopropyl borate, 9-BBN (0.5 M THF solution), NaHMDS (95%), 2-methyl-3-pentanone, 3-methyl-2-butanone, anhydrous dioxane, anhydrous DME, dicyclohexylphenylphosphine, and 1-hexene were purchased from Aldrich Chemical company. (±)-2,2'-Bis(dicyclohexylphosphino)-1,1'-binaphthyl 1[3] was prepared by metallation of the corresponding dibromobinaphthyl with t-butyllithium and quenching with chlorodicyclohexylphosphine using a procedure analogous to the synthesis of (±)-BINAP.[4] It was characterized by elemental analysis and by comparison of its $^1$H and $^{31}$P NMR spectra with literature data.[3] Tetrakis(triphenylphosphine)palladium was prepared according to a literature procedure.[5] Sodium t-butoxide was purchased from Aldrich Chemical Company; the bulk of this material was stored under nitrogen in a Vacuum Atmospheres glovebox. Small portions (1–2 g) were removed from the glovebox in glass vials, stored in the air in desiccators filled with anhydrous calcium sulfate, and weighed in the air. IR spectra reported in this paper were obtained by placing neat samples directly on the DiComp probe of an ASI REACTIR in situ IR instrument. Yields in Tables 1 and 2 refer to isolated yields (average of two runs) of compounds estimated to be ˃95% pure as determined by $^1$H NMR, and GC analysis or combustion analysis. Entries 1,[6] 2,[7] 3,[6] 4,[6] 5,[8] 6,[9] 7,[6] 8,[6] 9,[11] 13,[6] and 14,[10] from Table 1 have been previously reported by this group and were characterized by comparison of their $^1$H NMR spectra to those of samples prepared prior to this work; their purity was confirmed by GC analysis. The procedures described in this section are representative, thus the yields may differ from those given in Tables 1 and 2.

2-(N,N-Dimethylamino)-2'-(dicyclohexylphosphino)biphenyl (2)

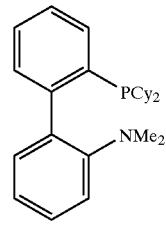

2

N,N-dimethylamino-2-bromoaniline[1] (4.0 g, 20.0 mmol) was loaded into an oven-dried flask which had been cooled to room temperature under an argon purge. The flask was purged with argon and THF (20 mL) was added. The solution was cooled to −78° C. and n-butyllithium (13.1 mL, 21.0 mmol, 1.6 M in hexanes) was added dropwise with stirring. After the addition was complete the reaction mixture was stirred at −78° C. for 75 min during which time a white precipitate formed. An additional 70 mL of THF was added, and the aryllithium suspension was then transferred via cannula to a separate flask containing a solution of triisopropyl borate (9.2 mL, 40.0 mmol) in THF (20 mL) which had been cooled to −78° C. The reaction mixture was stirred at −78° C. for 1 h, then warmed to room temperature and allowed to stir overnight (25 h). The reaction was quenched with 1 M aqueous HCl (250 mL), and stirred at room temperature for 15 min. The pH of the mixture was adjusted to pH 7 with 6 M aqueous NaOH, and the mixture was transferred to a separatory funnel. The mixture was extracted with ether (3×150 mL), and the combined organic extracts were dried over anhydrous magnesium sulfate, and concentrated in vacuo to give a brown oil which contained substantial amounts of N,N-dimethylaniline. This oil was then taken up in ether (100 mL), and extracted with 1 M aqueous NaOH (3×100 mL). The organic layer was discarded and the aqueous extracts were adjusted to pH 7 with 6 M aqueous HCl. The aqueous phase was then extracted with ether (3×100 mL), and the combined organic layers were dried over anhydrous magnesium sulfate, filtered, and concentrated in vacuo to give 1.85 g of 2-(N,N-dimethylamino)phenylboronic acid[12] as a viscous tan oil which was found to be ~50–60% pure by $^1$H NMR. This material was used without further purification.

The crude boronic acid was taken up in ethanol (5 mL) and was added to a flask containing a solution of tetrakis (triphenylphosphine)palladium[5] (700 mg, 0.61 mmol, 5 mol %) and 2-bromoiodobenzene (4.1 g, 14.5 mmol) in DME (100 mL) under argon. A solution of $Na_2CO_3$ (6.42 g, 60.6 mmol) in degassed water (30 mL) was added to the reaction vessel, and the mixture was heated to reflux for 48 h. The reaction mixture was then cooled to room temperature, diluted with ether (200 mL), and poured into a separatory funnel. The layers were separated, and the aqueous layer was extracted with ether (200 mL). The layers were separated and the aqueous layer was discarded. The combined organic layers were then washed with 1 M aqueous NaOH (50 mL), and the aqueous wash was discarded. The combined organic fractions were then extracted with 1 M aqueous HCl (4×150 mL). The organic fraction was discarded, and the combined aqueous acid extracts were basified to pH 14 with 6 M aqueous NaOH. The aqueous phase was extracted with ether (3×150 mL), and the combined organic layers were dried over anhydrous magnesium sulfate, filtered, and concentrated in vacuo to give 2.1 g of a white solid which was judged to be ~90–95% pure by $^1$H NMR. This material was used without further purification.

An oven-dried round-bottomed flask was cooled to room temperature under an argon purge and charged with the crude 1-(N,N-dimethylamino)-1'-bromobiphenyl. The flask was purged with argon, and THF (120 mL) was added. The solution was cooled to −78° C. with stirring, and n-butyllithium (5.2 mL, 8.37 mmol, 1.6 M in hexanes) was added dropwise. The solution was stirred at −78° C. for 35 min, then a solution of chlorodicyclohexylphosphine (2.21 g, 9.51 mmol) in THF (30 mL) was added dropwise to the reaction vessel. The reaction mixture was stirred at −78° C. and allowed to warm slowly to room temperature overnight. The reaction was then quenched with saturated aqueous $NH_4Cl$ (30 mL), diluted with ether (200 mL), and poured into a separatory funnel. The layers were separated and the aqueous phase was extracted with ether (50 mL). The combined organic layers were dried over anhydrous sodium sulfate, filtered, and concentrated to give a white solid. The crude material was recrystallized from degassed, hot ethanol under an argon atmosphere to afford 2.25 g (29% overall yield for 3 steps) of a white solid: mp 110° C.; $^1$H NMR (300 MHz, $CDCl_3$) δ 7.54 (d, 1H, J=6.8 Hz), 7.26–7.40 (m, 4H), 7.02–7.05 (m, 1H), 6.93–6.98 (m, 3H), 2.44 (s, 6H), 1.98–2.05 (m, 1H), 1.40–1.82 (m, 11 H), 0.75–1.38 (m, 10 H); $^{13}$C NMR (125 MHz, $CDCl_3$) δ 151.5, 149.8, 149.5, 135.8, 135.5, 135.3, 132.7, 132.4, 130.54, 130.49, 128.5, 128.1, 125.8, 120.6, 117.3, 43.2, 36.8, 36.7, 33.5, 33.4, 30.9, 30.8, 30.6, 30.4, 29.8, 29.7, 28.5, 27.6, 27.54, 27.46, 27.3, 27.2, 26.7, 26.4 (observed complexity due to P-C splitting; definitive assignments have not yet been made); $^{31}$P NMR (121.5 MHz, $CDCl_3$) δ −9.2; IR (neat, $cm^{-1}$) 2922, 1444, 745. Anal Calcd for $C_{26}H_{36}NP$: C, 79.35; H, 9.22. Found: C, 79.43; H, 9.48.

General procedure for the palladium-catalyzed amination of aryl chlorides: An oven-dried Schlenk tube or test tube fitted with a rubber septum was purged with argon and charged with tris(dibenzylidineacetone)dipalladium (0.005 mmol, 1 mol % Pd), ligand 2 (0.015 mmol, 1.5 mol %), and NaOt-Bu (1.4 mmol). The tube was purged with argon, and toluene (2.0 mL), the aryl chloride (1.0 mmol) and the amine (1.2 mmol) were added. The mixture was stirred in an 80° C. oil bath until the starting aryl chloride had been completely consumed as judged by GC analysis. The reaction mixture was then cooled to room temperature, diluted with ether (20 mL), filtered through celite and concentrated in vacuo. The crude material was then purified by flash chromatography on silica gel.

N-(4-methylphenyl)-p-anisidine.[13]

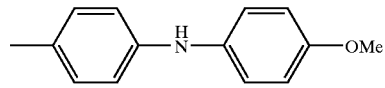

The general procedure except using a reaction temperature of 100° C. gave 198 mg (93%) of a tan solid: mp 80–81° C. (lit.[13] mp 84–85° C.). $^1$H NMR (300 MHz, $CDCl_3$) δ 6.98–7.05 (m, 4H), 6.80–6.86 (m, 4H), 5.37 (s, br 1H), 3.76 (s, 3H), 2.26 (s, 3H); $^{13}$C NMR (125 MHz, $CDCl_3$) δ 154.8, 142.4, 136.7, 129.7, 129.3, 121.1, 116.6, 114.7, 55.6, 20.5; IR (neat, $cm^{-1}$) 3416, 2910, 1513, 1304, 815.

N-benzyl-p-toluidine[14]

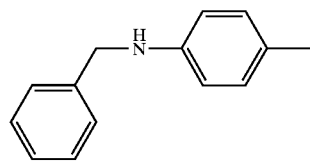

The general procedure except using 1 as the ligand, and 1.5 equiv of benzyl amine, gave 177 mg (90%) of a pale yellow oil: $^1$H NMR (250 MHz, $CDCl_3$) δ 7.25–7.39 (m, 5H), 6.98 (d, 2H, J=8.1 Hz), 6.56 (d, 2H, J=8.5 Hz), 4.31 (s, 2H), 3.90 (br s, 1H), 2.23 (s, 3H); $^{13}$C NMR (125 MHz, $CDCl_3$) δ 145.9, 139.7, 129.7, 128.5, 127.4, 127.1, 126.7, 113.0, 48.6, 20.3; IR (neat, $cm^{-1}$) 3416, 3026, 1521, 807.

N-(4-Cyanophenyl)morpholine[11]

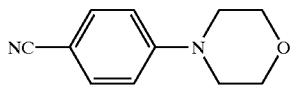

An oven-dried resealable Schlenk tube was purged with argon and charged with $Pd_2(dba)_3$ (11.5 mg, 0.025 mmol, 5 mol % Pd), 2 (14.8 mg, 0.075 mmol, 7.5 mol %), NaOt-Bu (68 mg, 0.71 mmol) and 4-chlorobenzonitrile (69 mg, 0.50 mmol). The tube was purged with argon then DME (0.5 mL) and morpholine (53 µL, 0.61 mmol) were added through a rubber septum. The septum was removed, the tube was sealed with a teflon screw cap and the mixture was stirred at room temperature for 26 h, then diluted with EtOAc, filtered through celite and concentrated in vacuo. The crude material was purified by flash chromatography on silica gel to afford 91 mg (96%) of a tan solid.

Amination using 0.05 mol % Pd. An oven-dried resealable Schlenk tube was purged with argon and charged with $Pd_2(dba)_3$ (2.3 mg, 0.0025 mmol, 0.05 mol % Pd), ligand 2 (2.9 mg, 0.0075 mmol, 0.075 mol %), and NaOt-Bu (1.34 g, 13.9 mmol). Toluene (10 mL), di-n-butylamine (2.00 mL, 11.9 mmol), and 4-chlorotoluene (1.18 mL, 10.0 mmol) were added and the mixture was degassed using three freeze-pump-thaw cycles. The reaction vessel was placed under argon, sealed with a teflon screw cap, and stirred in a 100° C. oil bath for 20 h after which time GC analysis showed the aryl halide had been completely consumed. The reaction mixture was cooled to room temperature, diluted with ether (100 mL) and extracted with 1 M HCl (3×100 mL). The combined aqueous acid phase was basified with 3N NaOH, then extracted with ether (3×150 mL). The ethereal extracts were dried over anhydrous sodium sulfate, filtered and concentrated to afford 2.01 g (95%) of di-n-butyltoluidine[6] as a pale yellow oil.

General procedure for the room-temperature palladium-catalyzed amination of aryl bromides: An oven-dried resealable Schlenk tube was purged with argon and charged with $Pd_2(dba)_3$ (0.005–0.025 mmol, 1–5 mol % Pd), ligand 2 (0.015–0.075 mmol, 1.5–7.5 mol %), and NaOt-Bu (1.4 mmol) [see Table 1 for amount of Pd and ligand used]. The tube was purged with argon, fitted with a rubber septum and then DME (0.5 mL–1.0 mL), the aryl bromide (1.0 mmol) and the amine (1.2 mmol) were added via syringe. The septum was removed, the tube was sealed with a teflon screw cap and the mixture was stirred at room temperature for 24 h. The reaction mixture was then diluted with ether (20 mL), filtered through celite and concentrated in vacuo. The crude material was purified by flash chromatography on silica gel.

2,6-Dimethyl-N-(n-hexyl)aniline

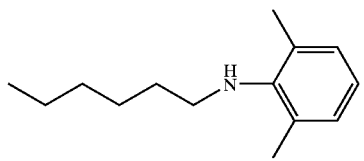

The general procedure was conducted with with 0.5 mmol of aryl bromide and afforded 90 mg (87%) of a colorless oil: $^1H$ NMR (300 MHz, $CDCl_3$) δ 6.98 (d, 2H, J=7.5 Hz), 6.79 (t, 1H, J=7.5 Hz), 2.97 (t, 2H, J=7.2 Hz), 2.94–2.99 (br, 1H), 2.28 (s, 6H), 1.52–1.60 (m, 2H), 1.28–1.41 (m, 6H), 0.89 (t, 3H, J=6.8 Hz); $^{13}C$ NMR (125 MHz, $CDCl_3$) δ 146.5, 129.1, 128.8, 121.5, 48.7, 31.7, 31.2, 26.9, 22.6, 18.5, 14.0; IR (neat, cm−1) 3384, 2926, 1472, 1256, 1219, 762. Anal Calcd for $C_{14}H_{23}N$: C, 81.89; H, 11.29. Found: C,; H,.

N-(2,5-Dimethylphenyl)morpholine

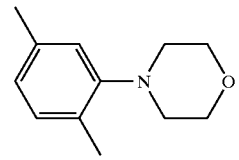

The general procedure was conducted at 2.0 M concentration and afforded 185 mg (95%) of a colorless oil: $^1H$ NMR (300 MHz, $CDCl_3$) δ 7.06 (d, 1H, J=7.7 Hz), 6.80–6.82 (m, 2H), 3.84 (t, 4H, J=4.6 Hz), 2.89 (t, 4H, J=4.6 Hz), 2.31 (s, 3H), 2.26 (s, 3H); $^{13}C$ NMR (125 MHz, $CDCl_3$) δ 151.1, 136.2, 131.0, 129.3, 124.0, 119.7, 67.5, 52.3, 21.1, 17.4; IR (neat, $cm^{-1}$) 2955, 2851, 1505, 1242, 1117, 807. Anal Calcd for $C_{12}H_{17}NO$: C, 75.35; H,.8.96. Found: C,; H,.

N-(4-carbomethoxyphenyl)morpholine[15]

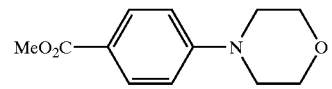

The general procedure was conducted with 0.5 mmol of aryl bromide except using $K_3PO_4$ in place of NaOt-Bu at 80° C., EtOAc as the workup solvent and gave 89 mg (80%) of a colorless solid: mp 152–154° C. (lit.[15] mp 157–160° C.). $^1H$ NMR (300 MHz, $CDCl_3$) δ 7.94 (d, 2H, J=8.6 Hz), 6.86 (d, 2H, J=8.8 Hz), 3.87 (s, 3H), 3.86 (t, 4H, J=4.8 Hz), 3.29 (t, 4H, J=4.8 Hz); $^{13}C$ NMR (125 MHz, $CDCl_3$) δ 167.0, 154.2, 131.2, 120.4, 113.5, 66.6, 51.6, 47.8; IR (neat, $cm^{-1}$) 2968, 1698, 1289, 1116, 768. Anal Calcd for $C_{12}H_{15}NO_3$: C, 65.14; H, 6.83. Found: C,; H,.

N-(4-acetylphenyl)morpholine[16]

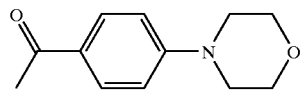

The general procedure except using $Pd(OAc)_2$, $K_3PO_4$ in place of $Pd_2(dba)_3$, NaOtBu, at a reaction temperature of 80° C., and 1/1 $Et_2O$/EtOAc as the workup solvent gave 169 mg (82%) of a pale yellow solid: m.p. 93–94° C. (lit.[14] mp 97–98° C.). $^1H$ NMR (300 MHz, $CDCl_3$) δ 7.89 (d, 2H, J=9.1 Hz), 6.87 (d, 2H, J=9.1 Hz), 3.86 (t, 4H, J=4.8 Hz), 3.31 (t, 4H, J=5.1 Hz), 2.54 (s, 3H); $^{13}C$ NMR (125 MHz, $CDCl_3$) δ 196.4, 154.1, 130.2, 128.1, 113.2, 66.5, 47.5, 26.0; IR (neat, $cm^{-1}$) 2972, 1660, 1243, 1119, 818. Anal Calcd for $C_{12}H_{15}NO_2$: C, 70.22; H, 7.37. Found: C, 70.31; H, 7.22.

Aminations with dicyclohexylphenylphosphine as the supporting ligand. The coupling of 4-chlorotoluene and di-n-butylamine following the general procedure for catalytic amination of aryl chlorides using dicyclohexylphenylphosphine in place of 2 led to 96% conversion (17% GC yield) in 12 h. In the same amount of time, the reaction using ligand 2 was complete, affording a 97% isolated yield of the desired product. The coupling of 2-bromo-p-xylene and morpholine following the room temperature procedure above, replacing 2 with dicyclohexylphenylphosphine (1.5 L/Pd), led to 2.5% consumption of the starting aryl bromide, with a trace amount of product detected (GC). When a ratio of 3 L/Pd was used, no reaction was observed.

General procedure for the room-temperature Suzuki coupling of aryl halides: An oven-dried resealable Schlenk tube was purged with argon and charged with Pd(OAc)$_2$ (0.02 mmol, 2 mol %), ligand 2 (0.03 mmol, 3 mol %), the boronic acid (1.5 mmol), and cesium fluoride (3.0 mmol). The tube was purged with argon, and dioxane (3 mL) and the aryl halide (1.0 mmol) were added through a rubber septum. The septum was removed, the tube was sealed with a teflon screw cap and the mixture was stirred at room temperature until the starting aryl halide had been completely consumed as judged by GC analysis. The reaction mixture was then diluted with ether (20 mL) and poured into a separatory funnel. The mixture was washed with 1 M NaOH (20 mL), and the layers were separated. The aqueous layer was extracted with ether (20 mL), and the combined organic layers were dried over anhydrous magnesium sulfate, filtered, and concentrated in vacuo. The crude material was then purified by flash chromatography on silica gel.

3,5-Dimethylbiphenyl[17]

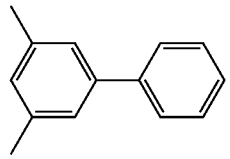

The general procedure using 1 mol % Pd(OAC)$_2$ and 1.5 mol % ligand 2 gave 171 mg (94%) of a colorless oil. $^1$H NMR (300 MHz, CDCl$_3$) δ 7.57 (d, 2H, J=6.8 Hz), 7.42 (t, 2H, J=7.2 Hz), 7.31–7.34 (m, 1H), 7.21 (s, 2H), 7.00 (s, 1H), 2.38 (s, 6H); $^{13}$C NMR (125 MHz, CDCl$_3$) δ 141.5, 141.3, 138.2, 128.9, 128.6, 127.2, 127.0, 125.1, 21.4; IR (neat, cm$^{-1}$) 3030, 1602, 849, 760. Anal Calcd for C$_{14}$H$_{14}$: C, 92.26; H, 7.74. Found: C, 91.98; H, 8.02.

2,5,3'-Trimethylbiphenyl.[18]

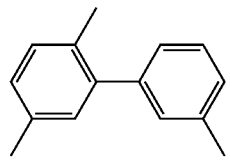

The general procedure gave 192 mg (98%) of a colorless oil which contained 4% 3,3'-dimethylbiphenyl as determined by $^1$H NMR: $^1$H NMR (300 MHz, CDCl$_3$) δ 7.25–7.28 (m, 1H), 7.04–7.16 (m, 6H), 2.39 (s, 3H), 2.34 (s, 3H), 2.23 (s, 3H); $^{13}$C NMR (125 MHz, CDCl$_3$) δ 142.1, 141.9, 137.5, 135.0, 132.1, 130.5, 130.2, 129.9, 127.85, 127.80, 127.3, 126.2, 21.4, 20.9, 19.9; IR (neat, cm$^{-1}$) 2949, 1451, 811, 703. Anal Calcd for C$_{15}$H$_{15}$: C, 92.26; H, 7.74. Found: C, 92.34; H, 7.66.

4-Acetyl-3'-methylbiphenyl[19]

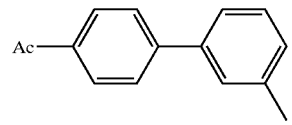

The general procedure gave 190 mg (90%) of a white solid: mp 84–86° C. (lit.[19] mp 92° C.). $^1$H NMR (300 MHz, CDCl$_3$) δ 8.02 (d, 2H, J=8.5 Hz), 7.68 (d, 2H, J=8.5 Hz), 7.33–7.44 (m, 3H), 7.20–7.26 (m, 1H), 2.64 (s, 3H), 2.43 (s, 3H); $^{13}$C NMR (125 MHz, CDCl$_3$) δ 197.6, 145.8, 139.7, 138.5, 135.7, 128.9, 128.8, 127.9, 127.1, 124.3, 26.5, 21.4; IR (neat, cm$^{-1}$) 3019, 1683, 1270, 787. Anal Calcd for C$_{15}$H$_{14}$O: C, 85.68; H, 6.71. Found: C, 85.79; H, 6.92

Methyl 4-phenylbenzoate[20]

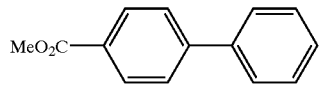

The general procedure (except using water for the aqueous workup in place of 1 M aqueous NaOH) gave 193 mg (91%) of a white solid: mp 113° C. (lit.[20] mp 117–118° C.). $^1$H NMR (300 MHz, CDCl$_3$) δ 8.11 (d, 2H, J=8.3 Hz), 7.61–7.68 (m, 4H), 7.39–7.49 (m, 3H), 3.94 (s, 3H); $^{13}$C NMR (125 MHz, CDCl$_3$) δ 166.9, 145.5, 139.9, 130.0, 128.8, 128.1, 127.2, 126.9, 52.0; IR (neat, cm$^{-1}$) 2945, 1710, 1270, 1112, 749. Anal Calcd for C$_{14}$H$_{13}$O$_2$: C, 78.85; H, 6.14. Found: C, 79.04; H, 6.16.

4-Hexylanisole[21]

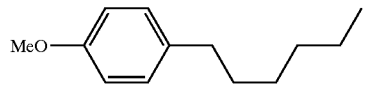

An oven-dried resealable Schlenk tube was capped with a rubber septum, cooled under an argon purge, charged with 1-hexene (0.19 mL, 1.5 mmol), and cooled to 0° C. A solution of 9-BBN in THF (3 mL, 1.5 mmol, 0.5 M) was added, the flask was stirred at 0° C. for 15 min, then warmed to room temperature and stirred for 5 h. 4-Chloroanisole (0.12 mL, 1.0 mmol) was added, the septum was removed, and palladium acetate (4.4 mg, 0.02 mmol, 2 mol %), ligand 2 (11.9 mg, 0.03 mmol, 3 mol %), and cesium fluoride (456 mg, 3.0 mmol) were added under a stream of argon. The septum was replaced and the flask was purged with argon for 30 s. Dioxane (2 mL) was added, the septum was removed, the tube was sealed with a teflon screw cap, and the mixture was stirred at rt for 2 min. The reaction mixture was then heated to 50° C. with stirring for 22 h, at which time GC analysis showed the aryl chloride had been completely consumed. The mixture was cooled to room temperature, diluted with ether (20 mL), and poured into a separatory funnel. The mixture was washed with 1 M aqueous NaOH (20 mL), the layers were separated, and the aqueous phase was extracted with ether (20 mL). The combined organic layers were dried over anhydrous magnesium sulfate, filtered, and concentrated in vacuo. The crude material was purified by flash chromatography to afford 170 mg (89%) of a colorless oil: $^1$H NMR (300 MHz, CDCl$_3$) δ 7.09 (d, 2H, J=8.8 Hz), 6.82 (d, 2H, J=8.6 Hz), 3.78 (s, 3H), 2.54 (t, 2H, J=7.5 Hz), 1.54–1.60 (m, 2H), 1.28–1.35 (m, 6H), 0.88 (t, 3H, J=6.8 Hz); $^{13}$C NMR (125 MHz, CDCl$_3$) δ 157.6, 135.0, 129.2, 113.6, 55.2, 35.0, 31.73, 31.70; 28.9, 22.6, 14.1; IR (neat, cm$^{-1}$) 2926, 1513, 1243, 1038, 822. Anal Calcd for C$_{13}$H$_{20}$O: C, 81.20; H, 10.48. Found: C, 81.19; H, 10.62.

General procedure for K$_3$PO$_4$ promoted Suzuki coupling of aryl chlorides: An oven-dried resealable Schlenk tube was purged with argon and charged with Pd(OAc)$_2$ (0.01 mmol, 0.5 mol %), ligand 2 (0.015 mmol, 0.75 mol %), the boronic acid (3.0 mmol), and potassium phosphate (4.0 mmol). The tube was purged with argon, and dioxane (6 mL) and 4-chlorotoluene (2.0 mmol) were added through a rubber septum. The septum was removed, the tube was sealed with a teflon screw cap and the mixture was stirred at room temperature for 2 min, then heated to 100° C. with stirring until the starting aryl chloride had been completely consumed as judged by GC analysis. The reaction mixture was then cooled to room temperature, diluted with ether (20 mL) and poured into a separatory funnel. The mixture was washed with 1 M NaOH (20 mL), and the layers were separated. The aqueous layer was extracted with ether (20 mL), and the combined organic layers were dried over anhydrous magnesium sulfate, filtered, and concentrated in vacuo. The crude material was then purified by flash chromatography on silica gel.

4-Methoxybiphenyl[22]

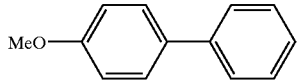

The general procedure gave 347 mg (94%) of a white solid: mp 83–84° C. (lit.[22] mp 87° C.); $^1$H NMR (250 MHz, CDCl$_3$) δ 7.52–7.58 (m, 4H), 7.42 (t, 2H, J=7.8 Hz), 7.26–7.38 (m, 1H), 6.97 (d, 2H, J=6.7 Hz), 3.86 (s, 3H); $^{13}$C NMR (125 MHz, CDCl$_3$) δ 159.1, 140.8, 133.7, 128.7, 128.1, 126.7, 126.6, 114.2, 55.3; IR (neat, cm$^{-1}$) 3003, 1251, 1034, 834, 760. Anal Calcd for C$_{13}$H$_{12}$O: C, 84.75; H, 6.57. Found: C, 85.06; H, 6.72.

4-Methylbiphenyl[23]

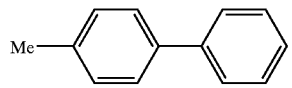

The general procedure gave 319 mg (95%) of a white solid: mp 44–46° C. (lit.[23] mp 49–50° C.); $^1$H NMR (250 MHz, CDCl$_3$) δ 7.57 (d, 2H, J=8.8 Hz), 7.39–7.51 (m, 4H), 7.23–7.35 (m, 3H), 2.40 (s, 3H); $^{13}$C NMR (125 MHz, CDCl$_3$) δ 141.2, 138.4, 136.9, 129.4, 128.7, 126.94, 126.92, 21.0; IR (neat, cm$^{-1}$) 3030, 1486, 822, 753. Anal Calcd for C$_{13}$H$_{12}$: C, 92.81; H, 7.19. Found: C, 92.86; H, 7.15.

4-Methyl-2'-methoxybiphenyl[24]

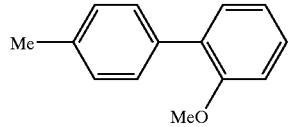

The general procedure was conducted on a 1 mmol scale using 1 mol % Pd(OAc)$_2$, 1.5 mol % ligand 2, and 3 eq CsF in place of K$_3$PO$_4$ to give 196 mg (99%) of a white solid, mp 74–75° C. (lit.[24] mp 70–72° C.); $^1$H NMR (250 MHz, CDCl$_3$) δ 7.42 (d, 2H, J=8.1 Hz), 7.21–7.33 (m, 4H), 7.16–7.04 (m, 2H), 3.81 (s, 3H), 2.39 (s, 3H); $^{13}$C NMR (125 MHz, CDCl$_3$) δ 156.5, 136.5, 135.6, 130.7, 129.4, 128.6, 128.3, 120.8, 111.2, 55.5, 21.2; IR (neat, cm$^{-1}$) 2964, 1227, 1023,757. Anal Calcd for C$_{14}$H$_{14}$O: C, 84.81; H, 7.12. Found: C, 84.94; H, 7.36.

Suzuki coupling with dicyclohexylphenylphosphine as the supporting ligand. Two coupling reactions of 4-chlorotoluene with phenylboronic acid using the general procedures for Suzuki couplings described above were carried out with dicyclohexylphenylphosphine (2 L/Pd) in place of 2. The reaction conducted at room temperature with CsF as the base proceeded to 10% conversion (5% GC yield) after 2 days, while the reaction at 100° C. with K$_3$PO$_4$ as the base proceeded to 27% conversion (18% GC yield) in 2 days.

2-Methyl-4-(3,5-xylyl)-3-pentanone

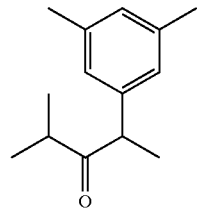

An oven-dried resealable Schlenk tube was charged with NaHMDS (238 mg, 1.3 mmol) under nitrogen in a Vacuum Atmospheres glovebox. The tube was capped with a teflon screw cap and removed from the glovebox. The screwcap was removed and Pd$_2$(dba)$_3$ (13.7 mg, 0.015 mmol, 3 mol % Pd) and 2 (14.1 mg, 0.036 mmol, 3.6 mol %) were added under a stream of argon. The tube was capped with a rubber septum and toluene (3 mL) was added with stirring. The flask was then charged with 5-bromo-m-xylene (0.135 mL, 1.0 mmol), 2-methyl-3-pentanone (0.15 mL, 1.2 mmol), and additional toluene (3 mL). The septum was replaced with a teflon screw cap and the reaction mixture was stirred at room temperature for 22 h until the starting aryl bromide had been completely consumed as judged by GC analysis. The reaction was quenched with 5 mL of saturated aqueous NH4Cl, diluted with ether (20 mL), and poured into a separatory funnel. The layers were separated, and the aqueous phase was extracted with ether (10 mL). The combined organic layers were dried over anhydrous magnesium sulfate, filtered, and concentrated in vacuo. The crude material was purified by flash chromatography on silica gel to give 163 mg (80%) of a colorless oil. GC and NMR analysis showed the material obtained was a mixture of the desired product and a regioisomer containing the aryl group at the 2-position of the ketone (46/1 ratio by GC analysis; 40/1 ratio by $^1$H NMR analysis). NMR data are given for the major product only. $^1$H NMR (250 MHz, CDCl$_3$) δ 6.88 (s, 1H), 6.81 (s, 2H), 3.83 (q, 1H, J=6.9 Hz), 2.68 (p, 1H, J=6.9 Hz), 2.29 (s, 6H), 1.34 (d, 3H, J=6.9 Hz), 1.07 (d, 3H, J=7.0 Hz), 0.92 (d, 3H, J=6.6 Hz); $^{13}$C NMR (125 MHz, CDCl$_3$) δ 214.7, 140.7, 138.3, 128.6, 125.7, 50.9, 39.0, 21.2, 19.3, 18.2, 18.1; IR (neat, cm$^{-1}$) 2972, 1710, 1101, 849. Anal (for the mixture) Calcd for C$_{14}$H$_{20}$O: C, 82.3; H, 9.87. Found: C, 82.09; H, 9.85.

1,1-Bis(4-methylphenyl)-3-methyl-2-butanone

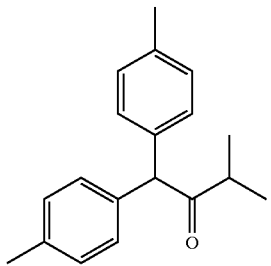

An oven-dried Schlenk tube was cooled under an argon purge and charged with Pd$_2$(dba)$_3$ (13.7 mg, 0.015 mmol, 3 mol % Pd), 2 (14.1 mg, 0.036 mmol, 3.6 mol %), and NaOtBu (211 mg, 2.2 mmol). The flask was purged with argon, and toluene (3 mL) was added with stirring. The flask was then charged with 4-chlorotoluene (0.24 mL, 2.0 mmol), 3-methyl-2-butanone (0.105 mL, 1.0 mmol), and additional toluene (3 mL). The reaction mixture was stirred at room temperature for 2 min, then heated to 80° C. with stirring for 22 h at which time GC analysis showed the starting aryl chloride had been completely consumed. The reaction mixture was cooled to room temperature, quenched with saturated aqueous NH$_4$Cl (5 mL), diluted with ether (20 mL), and poured into a separatory funnel. The layers were separated and the aqueous phase was extracted with ether (10 mL). The combined organic fractions were dried over anhydrous magnesium sulfate, filtered, and concentrated in vacuo. The crude material was purified by flash chromatography on silica gel to give 210 mg (79%) of a white solid: mp 48–51° C.; $^1$H NMR (300 MHz, CDCl$_3$) δ 7.00–7.18 (m, 8H), 5.22 (s, 1H), 2.79 (p, 1H, J=6.8 Hz), 2.31 (s, 6H), 1.10 (d, 6H, J=6.8 Hz); $^{13}$C NMR (125 MHz, CDCl$_3$) δ 212.3, 136.6, 135.8, 129.24, 129.16, 128.9, 128.7, 61.4, 40.7, 21.0, 18.6; IR (neat, cm$^{-1}$) 2972, 1718, 1513, 1038, 803. Anal Calcd for C$_{14}$H$_{20}$O: C, 85.67; H, 8.32. Found: C, 86.02; H, 8.59.

References for Supporting Information for Example 1

(1) Parham, W. E.; Piccirilli, R. M. *J. Org. Chem.* 1977, 42, 257–260.
(2) Thompson, W. J.; Gaudino, J. *J. Org. Chem.* 1984, 49, 5237–5243.
(3) Zhang, X.; Mashima, K.; Koyano, K.; Sayo, N.; Kumobayashi, H.; Akutagawa, S.; Takaya, H. *J. Chem. Soc. Perkin Trans.* 1 1994, 2309–2322.
(4) Miyashita, A.; Takaya, H.; Souchi, T.; Noyori, R. *Tetrahedron* 1984, 40, 1245–1253.
(5) Hegedus, L. S. in *Organometallics in Synthesis Schlosser*, M. Ed., John Wiley and Sons, West Sussex, England, 1994, p 448.
(6) Wolfe, J. P.; Buchwald, S. L. *J. Org. Chem.* 1996, 61, 1133–1135.
(7) Marcoux, J. -F.; Wagaw, S.; Buchwald, S. L. *J. Org Chem.* 1997, 62, 1568–1569.
(8) Wolfe, J. P.; Buchwald, S. L. *J. Am. Chem. Soc.* 1997, 119, 6054–6058.
(9) Wolfe, J. P.; Buchwald, S. L. *J. Am. Chem. Soc.* 1996, 118, 7215–7216.
(10) Wolfe, J. P.; Buchwald, S. L. *Tetrahedron Lett.* 1997, 38, 6359–6362.
(11) Wolfe, J. P.; Buchwald, S. L. *J. Org. Chem.* 1997, 62, 1264–1267.
(12) Lauer, M.; Wulff, G. *J. Organomet. Chem.* 1983, 256, 1–9.
(13) Abe, M.; Takahashi, M. *Synthesis* 1990, 939–942.
(14) Watanabe, Y.; Tsuji, Y.; Ige, H.; Ohsugi, Y.; Ohta, T. *J. Org. Chem.* 1984, 49, 3359–3363.
(15) Behringer, H.; Heckrnaier, P. *Chem. Ber.* 1969, 102, 2835–2850.
(16) Kotsuki, H.; Kobayashi, S.; Matsumoto, K.; Suenaga, H.; Nishizawa, H. *Synthesis* 1990, 1147–1148.
(17) Häfelinger, G.; Beyer, M.; Burry, P.; Eberle, B.; Ritter, G.; Westermayer, G.; Westermayer, M. *Chem. Ber.* 1984, 117, 895–903.
(18) Novrocik, J.; Novrocikova, M.; Titz, M. *Coll. Czech. Chem. Commun.* 1980, 3140–3149.
(19) Wirth, H. O.; Kern, W.; Schmitz, E. *Makromol. Chem.* 1963, 68, 69–99.
(20) Barba, I.; Chinchilla, R.; Gomez, C. *Tetrahedron* 1990, 46, 7813–7822.
(21) Skraup, S.; Nieten, F. *Chem. Ber.* 1924, 1294–1310.
(22) Darses, S.; Jeffery, T.; Brayer, J. -L.; Demoute, J. -P.; Genet, J. -P. *Bull. Soc. Chim. Fr.* 1996, 133, 1095–1102.
(23) Rao, M. S. C.; Rao, G. S. K. *Synthesis* 1987, 231–233.
(24) Hatanaka, Y. Goda, K. -i.; Okahara, Y.; Hiyama, T. *Tetrahedron* 1994, 50, 8301–8316.

EXAMPLE 2

Synthesis of N-(2,5-Dimethylphenyl)-N-methylaniline

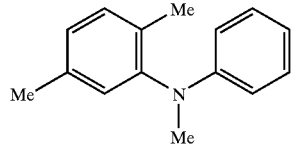

An oven-dried test tube was purged with argon and charged with Pd$_2$(dba)$_3$ (4.6 mg, 0.005 mmol, 1.0 mol % Pd), 2 [Example 1] (6.0 mg, 0.015 mmol, 1.5 mol %), and NaOt-Bu (135 mg, 1.40 mmol). The test tube was fitted with a septum, then toluene (2.0 mL), N-methylaniline (135 µL, 1.25 mmol), and 2-chloro-p-xylene (135 µL, 1.01 mmol) were added. The mixture was stirred at 80° C. for 13 h, then cooled to room temperature, diluted with ether (20 mL), filtered and concentrated. The crude material was purified by flash chromatography on silica gel to afford 202 mg (95%) of a colorless oil.

EXAMPLE 3

Synthesis of Di-n-butyl-p-toluidine

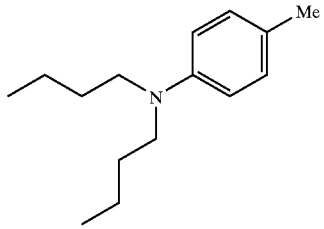

An oven-dried resealable Schlenk tube was purged with argon and charged with Pd$_2$(dba)$_3$ (2.3 mg, 0.0025 mmol, 0.05 mol % Pd), 2 [Example 1] (2.9 mg, 0.0075 mmol, 0.075 mol %), and NaOt-Bu (1.34 g, 13.9 mmol). Toluene (10 mL), di-n-butylamine (2.00 mL, 11.9 mmol), and 4-chlorotoluene (1.18 mL, 10.0 mmol) were added and the mixture was degassed using three freeze-pump-thaw cycles. The reaction vessel was placed under argon, sealed with a teflon screw cap, and stirred in a 100° C. oil bath for 20 h after which time GC analysis showed the aryl halide had been completely consumed. The reaction mixture was cooled to room temperature, diluted with ether (100 mL) and extracted with 1 M HCl (3×100 mL). The combined aqueous acid phase was basified with 3N NaOH, then extracted with ether (3×150 mL). The ethereal extracts were dried over anhydrous sodium sulfate, filtered and concentrated to afford 2.01 g (95%) of a pale yellow oil.

EXAMPLE 4

Synthesis of N-(4-Cyanophenyl)morpholine

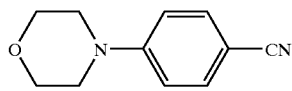

An oven-dried resealable Schlenk tube was purged with argon and charged with Pd$_2$(dba)$_3$ (11.5 mg, 0.025 mmol, 5 mol % Pd), 2 [Example 1] (14.8 mg, 0.075 mmol, 7.5 mol %), NaOt-Bu (68 mg, 0.71 mmol) and 4-chlorobenzonitrile (69 mg, 0.50 mmol). The tube was purged with argon then DME (0.5 mL) and morpholine (53 ILL, 0.61 mmol) were added through a rubber septum. The septum was removed, the tube was sealed with a teflon screw cap and the mixture was stirred at room temperature for 26 h. The reaction was then diluted with EtOAc (20 mL), filtered through celite and concentrated in vacuo. The crude material was purified by flash chromatography on silica gel to afford 91 mg (96%) of a tan solid.

EXAMPLE 5

Synthesis of N-(2,5-Dimethylphenyl)morpholine

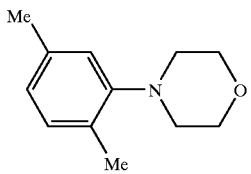

An oven-dried resealable Schlenk tube was purged with argon and charged with Pd$_2$(dba)$_3$ (13.9 mg, 0.015 mmol, 3.0 mol % Pd), 2 [Example 1] (17.9 mg, 0.045 mmol, 4.5 mol %), and NaOt-Bu (140 mg, 1.4 mmol). The tube was purged with argon, fitted with a rubber septum and then DME (0.5 mL), 2-bromo-p-xylene (140 µL, 1.01 mmol) and morpholine (105 µL, 1.2 mmol) were added via syringe. The septum was removed, the tube was sealed with a teflon screw cap and the mixture was stirred at room temperature for 24 h. The reaction mixture was then diluted with ether (20 mL), filtered through celite and concentrated in vacuo. The crude material was purified by flash chromatography on silica gel to afford 185 mg (95%) of a colorless oil.

EXAMPLE 6

Synthesis of N-(4-Carbomethoxyphenyl)morpholine

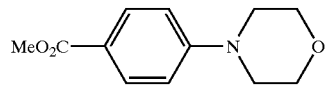

An oven-dried resealable Schlenk tube was purged with argon and charged with Pd$_2$(dba)$_3$ (2.3 mg, 0.0025 mmol, 1.0 mol % Pd), 2 [Example 1] (3.0 mg, 0.0076 mmol, 1.5 mol %), K$_3$PO$_4$ (150 mg, 0.71 mmol), and methyl 4-bromobenzoate (108 mg, 0.50 mmol). The tube was purged with argon, fitted with a rubber septum and then DME (1.0 mL) and morpholine (55 µL, 0.63 mmol) were added. The septum was removed, the tube was sealed with a teflon screw cap and the mixture was stirred at 80° C. for 24 h. The reaction mixture was then cooled to room temperature, diluted with EtOAc (20 mL), filtered through celite and concentrated in vacuo. The crude material was purified by flash chromatography on silica gel to afford 89 mg (80%) of a colorless solid.

EXAMPLE 7

Synthesis of N-benzyl-p-toluidine

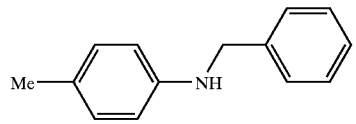

An oven dried Schlenk tube was purged with argon and charged with Pd$_2$(dba)$_3$ (4.6 mg, 0.005 mmol, 1.0 mol % Pd), Cy-BINAP (9.6 mg, 0.015 mmol, 1.5 mol %), and NaOtBu (135 mg, 1.4 mmol). The tube was purged with argon and charged with toluene (2 mL), 4-chlorotoluene (0.12 mL, 1.0 mmol), and benzylamine (0.165 mL, 1.5 mmol). The mixture was heated to 100° C. with stirring until the starting aryl chloride had been completely consumed as judged by GC analysis. The reaction mixture was cooled to room temperature, diluted with ether (20 mL), filtered through celite, and concentrated in vacuo. The crude material was then purified by flash chromatography on silica gel to give 177 mg (90%) of a pale yellow oil.

EXAMPLE 8

Synthesis of 3,5-dimethylbiphenyl Via Suzuki Coupling

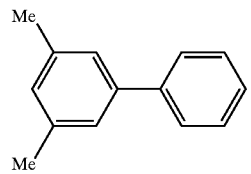

An oven dried resealable Schlenk tube was purged with argon and charged with palladium acetate (2.2 mg, 0.01 mmol, 1 mol %), ligand 2 [Example 1] (5.9 mg, 0.015 mmol, 1.5 mol %), phenylboron dihydroxide (183 mg, 1.5 mmol), and cesium fluoride (456 mg, 3.0 mmol). The tube was purged with argon, and dioxane (3 mL) and 5-bromo-m- xylene (0.135 mL, 1.0 mmol) were added through a rubber septum. The septum was removed, the tube was sealed with a teflon screw cap and the mixture was stirred at room temperature until the starting aryl bromide had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 171 mg (94%) of a colorless oil.

EXAMPLE 9

Synthesis of 4-methylbiphenyl Via Suzuki Coupling

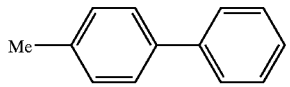

An oven dried resealable Schlenk tube was purged with argon and charged with palladium acetate (4.4 mg, 0.02 mmol, 2 mol %), ligand 2 [Example 1] (11.9 mg, 0.03 mmol, 3 mol %), phenylboron dihydroxide (183 mg, 1.5 mmol), and cesium fluoride (456 mg, 3.0 mmol). The tube was purged with argon, and dioxane (3 mL) and 4-chlorotoluene (0.12 mL, 1.0 mmol) were added through a rubber septum. The septum was removed, the tube was sealed with a teflon screw cap and the mixture was stirred at room temperature until the starting aryl chloride had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 157 mg (93%) of a glassy solid.

EXAMPLE 10

Synthesis of 3-methyl-4'-acetylbiphenyl Via Suzuki Coupling

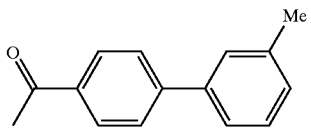

An oven dried resealable Schlenk tube was purged with argon and charged with palladium acetate (4.4 mg, 0.02 mmol, 2 mol %), ligand 2 [Example 1] (11.9 mg, 0.03 mmol, 3 mol %), 3-methylphenylboronic acid (204 mg, 1.5 mmol), and cesium fluoride (456 mg, 3.0 mmol). The tube was purged with argon, and dioxane (3 mL), and 4-chloroacetophenone (0.13 mL, 1.0 mmol) were added through a rubber septum. The septum was removed, the tube was sealed with a teflon screw cap and the mixture was stirred at room temperature until the starting aryl chloride had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 195 mg (93%) of a white solid.

EXAMPLE 11

Synthesis of 4-methoxybiphenyl Via Suzuki Coupling

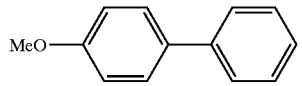

An oven dried resealable Schlenk tube was purged with argon and charged with palladium acetate (2.2 mg, 0.01 mmol, 0.5 mol %), ligand 2 [Example 1] (5.9 mg, 0.015 mmol, 0.75 mol %), phenylboron dihydroxide (366 mg, 3.0 mmol), and potassium phosphate (850 mg, 4.0 mmol). The tube was purged with argon, and dioxane (6 mL), and 4-chloroanisole (0.24 mL, 2.0 mmol) were added through a rubber septum. The septum was removed, the tube was sealed with a teflon screw cap and the mixture was stirred at room temperature for two minutes, then heated to 100° C. with stirring until the starting aryl chloride had been completely consumed as judged by GC analysis. The reaction mixture was then diluted with ether (40 mL) and poured into a separatory funnel. The mixture was washed with 1M NaOH (40 mL), and the layers were separated. The aqueous layer was extracted with ether (40 mL), and the combined organic extracts were dried over anhydrous magnesium sulfate, filtered, and concentrated in vacuo. The crude material was then purified by flash chromatography on silica gel to give 347 mg (94%) of a white solid.

EXAMPLE 12

Synthesis of 2-amino-2'-bromo-1,1'-binaphthyl benzophenone imine

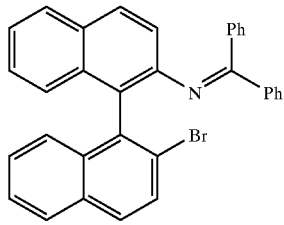

An oven-dried 100 mL round-bottom flask was fitted with a reflux condenser, purged with argon and charged with 2,2'-dibromo-1,1'-binaphthyl (5.0 g, 12.1 mmol), benzophenone imine (2.9 g, 15.7 mmol), NaOt-Bu (1.7 g, 18.0 mmol), Pd$_2$(dba)$_3$ (110 mmol, 0.12 mmol), bis(2-(diphenylphosphino)phenyl)ether (129 mg, 0.24 mmol), and toluene (50 mL). The mixture was stirred for 18 hours at 100° C. then cooled to room temperature and two-thirds of the solvent was removed under reduced pressure. Ethanol (25 mL) and water (3 mL) were added to the resulting mixture. The yellow crystals were collected on a Buchner funnel and washed with ethanol (10 mL) to afford 5.7 g (92%) of crude material which was used in the following Example without further purification.

EXAMPLE 13

Synthesis of 2-amino-2'-bromo-1,1'-binaphthyl

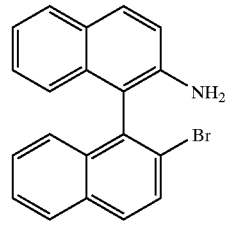

The crude imine from Example 12 (3.0 g, 5.9 mmol) was suspended in dichloromethane (100 mL) in a 300 mL round bottom flask. Concentrated hydrochloric acid (1.5 mL, 17.6 mmol) was added to the suspension which became homogeneous within 15 min. The reaction mixture was stirred for 18 hours at room temperature during which time a precipitate formed. The mixture was them treated with 1M NaOH (25 mL), and the layers were separated. The aqueous layer was extracted with additional dichloromethane (10 mL). The combined organic layers were washed with brine, dried over anhydrous magnesium sulfate, filtered, and concentrated in vacuo. The crude material was then purified by flash chromatography on silica gel to give 1.5 g (73%) of colorless crystals.

EXAMPLE 14

Synthesis of 2-N,N-dimethylamino-2'-bromo-1,1'-binaphthyl

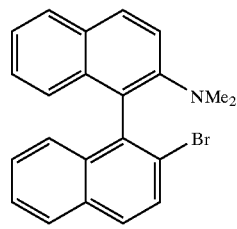

A 20 mL round-bottom flask was charged with amine from Example 13 (480 mg, 1.4 mmol), iodomethane (0.25 mL, 4.2 mmol), sodium carbonate (318 mg, 3.0 mmol), and DMF (8 mL), and then purged with argon. The mixture was heated to 50° C. and stirred until the starting material had been completely consumed. The reaction mixture was diluted with ether (5 mL) and water (1 mL) and then passed through a plug of silica gel. The filtrate was dried over anhydrous magnesium sulfate, filtered, and concentrated in vacuo to give 473 mg (91%) of colorless crystals.

EXAMPLE 15

Synthesis of 2-N,N-dimethylamino-2'-diphenylphosphino-1,1-binaphthyl (26)

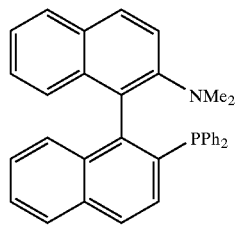

26

An oven-dried 20 mL round-bottom flask was charged with bromide from Example 14 (300 mg, 0.8 mmol) and THF (8 mL). The mixture was purged with argon and cooled to −78° C., then n-butyllithium (0.6 mL, 0.9 mmol) was added dropwise. The solution and stirred at −78° C. for 45 min, then chlorodiphenylphosphine (229 mg, 1.0 mmol) was added dropwise. The reaction was stirred for 1 hour at −78° C., then was allowed to warm to room temperature and stirred for 18 hours. Saturated aqueous ammonium chloride (2 mL) was added and the reaction mixture was extracted with ether (2×10 mL). The combined organic extracts were dried over anhdrous magnesium sulfate, filtered, and concentrated in vacuo. The crude material was purified by flash chromatography on silica gel to give 340 mg (88%) of 26 as colorless crystals.

EXAMPLE 16

Synthesis of 2-N,N-dimethylamino-2'-dicyclohexylphoshino-1,1'-binaphthyl (27)

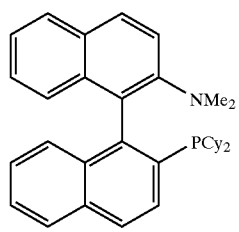

27

An oven-dried 20 mL round-bottom flask was charged with bromide from Example 14 (600 mg, 1.6 mmol) and THF (16 mL). The mixture was purged with argon and cooled to −78° C., then n-butyllithium (1.1 mL, 1.8 mmol) was added dropwise. The solution was stirred at −78° C. for 45 min, then chlorodicyclohexylphosphine (484 mg, 2.1 mmol) was added dropwise. The reaction was stirred for 1 hour at −78° C., then was allowed to warm to room temperature and stirred for 18 hours. Saturated aqueous ammonium chloride (2 mL) was added and the reaction mixture was extracted with ether (2×10 mL). The combined organic extracts were dried over anhdrous magnesium sulfate, filtered, and concentrated in vacuo. The crude material was recrystalized from dichloromethane and methanol to give 623 mg (79%) of 27 as colorless crystals.

EXAMPLE 17

Synthesis of N-(4-methoxyphenyl)pyrrolidine

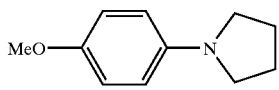

An oven dried test tube was charged with Pd$_2$(dba)$_3$ (4.5 mg, 0.005 mmol), 27 (7.4 mg, 0.015 mmol), 4-chloroanisole (140 mg, 0.98 mmol), pyrrolidine (85 mg, 1.2 mmol), NaOt-Bu (135 mg, 1.4 mmol), toluene (2 mL), and purged with argon. The mixture was heated to 80° C. and stirred for 18 hours. The reaction mixture was cooled to room temperature, diluted with ether (5 mL), filtered through a plug of celite, and concentrated in vacuo. The residue was purified by flash chromatography on silica gel to give 165 mg (95%) of the title product as colorless crystals.

EXAMPLE 18

Synthesis of N-benzyl-p-toluidine

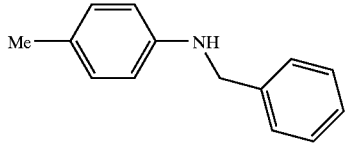

An oven dried resealable Schlenk tube was purged with argon and charged with Pd$_2$(dba)$_3$ (4.6 mg, 0.005 mmol, 1.0 mol % Pd), 27 (7.4 mg, 0.015 mmol, 1.5 mol %), and NaOtBu (135 mg, 1.4 mmol). The tube was purged with argon and toluene (2 mL), 4-chlorotoluene (0.12 mL, 1.0 mmol), and benzylamine (0.165 mL, 1.5 mmol) were added through a rubber septum. The septum was replaced with a teflon screw cap, the tube was sealed, and the mixture was heated to 100° C. with stirring until the starting aryl chloride had been completely consumed as judged by GC analysis. A small amount of diarylated benzylamine was detected in the crude reaction mixture (GC ratio of product/diarylated benzylamine=16/1). The reaction mixture was cooled to room temperature, diluted with ether (20 mL), and extracted with 1 M HCl (5×40 mL). The organic phase was discarded and the combined aqueous extracts were basisified to pH 14 with 6M NaOH and extracted with ether (4×50 mL). The combined organic extracts were dried over anhydrous magnesium sulfate, filtered, and concentrated in vacuo to give give 175 mg (89%) of a pale yellow oil.

EXAMPLE 19

Synthesis of N-(4-methylphenyl)indole

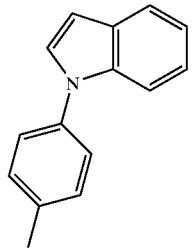

An oven-dried resealable Schlenk tube was purged with argon and charged with Pd$_2$(dba)$_3$ (11.2 mg, 0.012 mmol, 2.5 mol % Pd), 2 [Example 1] (14.4 mg, 0.036 mmol, 7.5 mol %), NaOt-Bu (130 mg, 1.35 mmol) and indole (115 mg, 0.98 mmol). The tube was purged with argon then toluene (1.0 mL) and 4-bromotoluene (120 µL, 0.98 mmol) were added through a rubber septum. The septum was removed, the tube was sealed with a teflon screw cap and the mixture was stirred at 100° C. for 21 h. The reaction was then diluted with ether (20 mL), filtered through celite and concentrated in vacuo. The crude material was purified by flash chromatography on silica gel to afford 191 mg (94%) of a colorless oil.

EXAMPLE 20

Synthesis of N-(4-fluorophenyl)indole

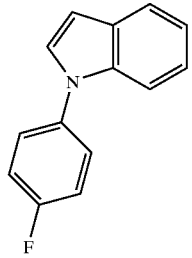

An oven-dried resealable Schlenk tube was purged with argon and charged with Pd$_2$(dba)$_3$ (11.5 mg, 0.013 mmol, 5 mol % Pd), 2 [Example 1] (14.8 mg, 0.038 mmol, 7.5 mol %), NaOt-Bu (68 mg, 0.71 mmol) and indole (60 mg, 0.51 mmol). The tube was purged with argon then toluene (0.5 mL) and 1-bromo4-fluorobenzene (55 µL, 0.50 mmol) were added through a rubber septum. The septum was removed, the tube was sealed with a teflon screw cap and the mixture was stirred at 100° C. for 36 h. The reaction was then diluted with ether (20 mL), filtered through celite and concentrated in vacuo. The crude material was purified by flash chromatography on silica gel to afford 81 mg (77%) of a colorless oil.

EXAMPLE 21

Synthesis of N-(4-methylphenyl)indole

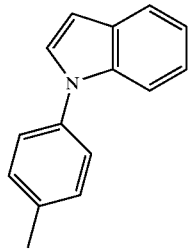

An oven-dried resealable Schlenk tube was purged with argon and charged with $Pd_2(dba)_3$ (11.6 mg, 0.012 mmol, 5 mol % Pd), 2 [Example 1] (11.0 mg, 0.028 mmol, 5.5 mol %), $Cs_2CO_3$ (230 mg, 0.75 mmol) and indole (60 mg, 0.51 mmol). The tube was purged with argon then toluene (1.0 mL) and 4-chlorotoluene (60 µL, 0.51 mmol) were added through a rubber septum. The septum was removed, the tube was sealed with a teflon screw cap and the mixture was stirred at 100° C. for 24 h. The reaction was then diluted with ether (20 mL), filtered through celite and concentrated in vacuo. The crude material was purified by flash chromatography on silica gel to afford 94 mg (89%) of a colorless oil.

EXAMPLE 22

Synthesis of 2-Bromo-2'-methoxy-1,1'-biphenyl

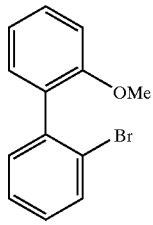

2-Bromoiodobenzene (640 µL, 5.0 mmol) was added to a suspension of $Pd(PPh_3)_4$ (305 mg, 0.26 mmol) in DME (100 mL) at room temperature under argon. After 15 min at room temperature, a solution of 2-methoxyphenylboronic acid (760 mg, 5.0 mmol) in ethanol (2 mL) was added, followed by aqueous $Na_2CO_3$ (2.0 M, 5 mL, 10 mmol). The reaction vessel was fitted with a reflux condenser and heated to reflux under argon for 22.5 h. The reaction mixture was then cooled to room temperature and filtered through Celite. The filter cake was washed with ether and water, and the filtrate was concentrated in vacuo. The resulting aqueous residue was diluted with brine and extracted with ether. The ethereal layer was dried ($MgSO_4$), filtered and concentrated. The crude residue was purified by flash chromatography on silica gel to afford 823 mg (63%) of a colorless oil.

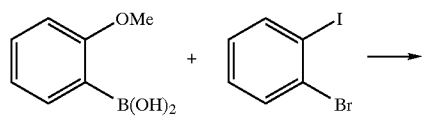

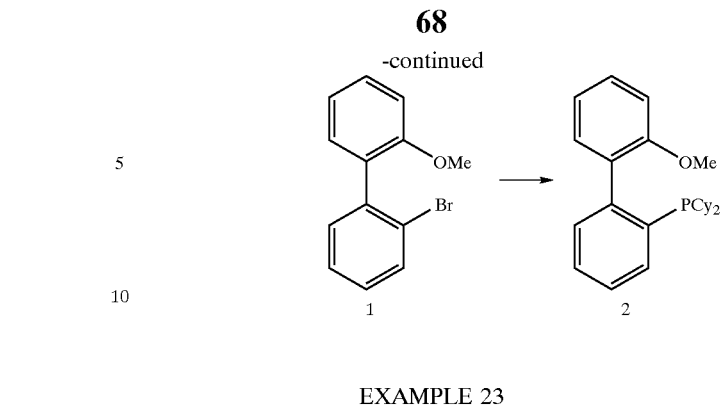

EXAMPLE 23

Synthesis of 2-Dicyclohexylphosphino-2'-methoxy-1,1'-biphenyl

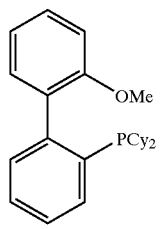

A solution of 1 (535 mg, 2.03 mmol) in THF (20 mL) was cooled to −78° C. under argon, then n-BuLi (1.6 M in hexane, 1.35 mL, 2.16 mmol) was added dropwise. After 2.5 h at −78° C., a solution of chlorodicyclohexylphosphine (570 mg, 2.45 mmol) in THF (3 mL) was added over 10 min. The reaction mixture was then allowed to warm to room temperature overnight, then quenched with saturated aqueous $NaHCO_3$ and concentrated in vacuo. The resulting aqueous suspension was extracted with ether (2×50 mL), and the combined ethereal layers were dried ($Na_2SO_4$), filtered and concentrated in vacuo. The resulting crude solid was recrystallized from ethanol to afford 420 mg (54%) of a white solid.

EXAMPLE 24

Synthesis of N-(4-methylphenyl)indole

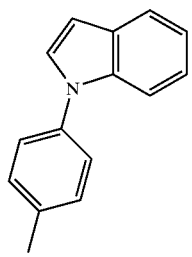

An oven-dried test tube was purged with argon and then charged with 2-dicyclohexylphosphino-2'-methoxy-1,1'-biphenyl (14.5 mg, 0.038 mmol, 7.5 mol %) and $Pd_2(dba)_3$ (11.6 mg, 0.013 mmol, 5.0 mol % Pd). Toluene (1.0 mL), indole (71 mg, 0.61 mmol), 4-chlorotoluene (60 mL, 0.51 mmol), and NaOt-Bu (70 mg, 0.73 mmol) were then added. The tube was fitted with a septum, purged with argon and heated at 100° C. for 28 h. The reaction was then cooled to room temperature, diluted with ether (20 mL), filtered through Celite and concentrated in vacuo. The residue was purified by flash chromatography on silica gel to afford 99 mg (94%) of a colorless oil.

EXAMPLE 25

Synthesis of 2-(di-tert-butylphosphino)biphenyl

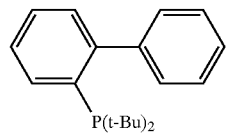

A solution of 2-bromobiphenyl (5.38 g, 23.1 mmol) and a few iodine crystals in 40 mL of THF with magnesium turnings (617 mg, 25.4 mmol) was heated to a reflux for 2 h. Heat was temporarily removed for the addition of cuprous chloride (2.40 g, 24.2 mmol) followed by chlorodi-tert-butylphosphine. Heating was resumed for 8 h. The reaction mixture was then removed from heat and allowed to cool to rt. The reaction mixture was poured onto 200 mL of 1:1 hexane/ether. The suspension was filtered and the filtercake was washed with 60 mL of hexane. The solid was partitioned between 150 mL of 1:1 hexane/ethyl acetate and 60 mL of concentrated ammonium hydroxide with 100 mL of water. The organic layer was washed with 100 mL of brine, dried over anhydrous sodium sulfate, and concentrated in vacuo. The white solid was recrystallized from 30 mL of MeOH to give white crystals of 2-(di-tert-butylphosphino)biphenyl (4.01 g, 58%). A second crop (464 mg, 67%) was obtained by recrystallization from 50 mL of MeOH and 25 mL of water.

EXAMPLE 26

General Procedure for Determining the Effect of Various Additives on the Preparation of 4-methylbiphenyl via Suzuki Coupling

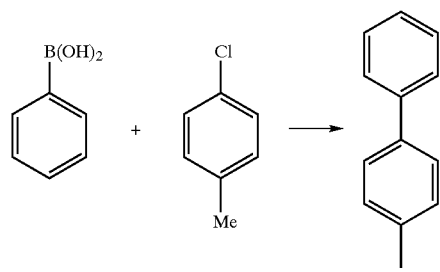

An oven dried resealable Schlenk tube was evacuated and backfilled with argon and charged with palladium acetate (2.2 mg, 0.01 mmol, 1.0 mol %), 2-(di-tert-butylphosphino)biphenyl (4.5 mg, 0.015 mmol, 1.5 mol %), phenylboron dihydroxide (183 mg, 1.5 mmol), additive (3.0 mmol), and 4-chlorotoluene (0.12 mL, 1.0 mmol). The tube was evacuated and backfilled with argon, and THF (2 mL) was added through a rubber septum. The reaction mixture was stirred at room temperature for 20 hours. The reaction mixture was then diluted with ethyl acetate (30 mL) and poured into a separatory funnel. The mixture was washed with 2.0M NaOH (20 mL), followed by brine (20 mL). The organic layer was submitted for GC analysis giving the results tabulated below.

| Additive | Conversion |
| --- | --- |
| Cesium Fluoride | 55% |
| Potassium-Fluoride | 62% |
| Potassium Carbonate | 10% |
| Potassium Phosphate | 38% |
| Sodium Acetate | 0% |

EXAMPLE 27

Synthesis of 4-t-butylbiphenyl Using $K_3PO_4$ as Base with 0.1 mol % Pd

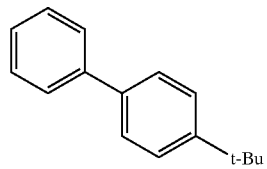

An oven dried resealable Schlenk tube was evacuated and backfilled with argon and charged with phenylboron dihydroxide (183 mg, 1.5 mmol), and potassium phosphate (425 mg, 2.0 mmol). The tube was evacuated and backfilled with argon, and DME (1.5 mL) and 1-bromo-4-t-butylbenzene (0.17 mL, 1.0 mmol) were added through a rubber septum. A separate flask was charged with $Pd_2(dba)_3$ (4.6 mg, 0.005 mmol), 2-(di-tert-butylphosphino)biphenyl (4.5 mmol, 0.015 mmol), and DME (1 mL). The mixture was stirred for 1 minute at room temperature, then 100 μL of this solution (0.1 mol % Pd, 0.15 mol % 2-(di-tert-butylphosphino)biphenyl) was added to the Schlenk tube followed by additional THF (1.5 mL). The septum was removed, the tube was sealed with a teflon screw cap and the mixture was stirred at room temperature for 2 minutes, then heated to 80° C. with stirring until the starting aryl bromide had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 199 mg (95%) of a glassy solid.

EXAMPLE 28

Synthesis of 4-t-butylbiphenyl Using CsF as Base with 0.05 mol % Pd

An oven dried resealable Schlenk tube was evacuated and backfilled with argon and charged with phenylboron dihydroxide (183 mg, 1.5 mmol), and cesium fluoride (456 mg, 3.0 mmol). The tube was evacuated and backfilled with argon, and THF (1.5 mL) and 1-bromo-4-t-butylbenzene (0.17 mL, 1.0 mmol) were added through a rubber septum. A separate flask was charged with $Pd_2(dba)_3$ (4.6 mg, 0.005 mmol), 2-(di-tert-butylphosphino)biphenyl (4.5 mmol, 0.015 mmol), and THF (1 mL). The mixture was stirred for 1 minute at room temperature, then 50 μL of this solution (0.05 mol % Pd, 0.075 mol % 2-(di-tert-butylphosphino)biphenyl) was added to the Schlenk tube followed by additional THF (1.5 mL). The septum was removed, the tube was sealed with a teflon screw cap and the mixture was stirred at room temperature for 2 minutes, then heated to 80° C. with stirring until the starting aryl bromide had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 202 mg (96%) of a glassy solid.

EXAMPLE 29

Optimized Synthesis of 4-methylbiphenyl Utilizing KF

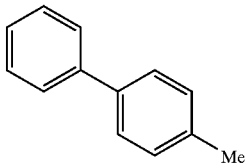

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), phenylboron dihydroxide (183 mg, 1.5 mmol), and potassium fluoride (174 mg, 3.0 mmol). The tube was evacuated and backfilled with argon, and THF (1 mL) and 4-chlorotoluene (0.12 mL, 1.0 mmol) were added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL) and poured into a separatory funnel. The mixture was washed with 1.0 M NaOH (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 158 mg (94%) of the title compound.

EXAMPLE 30

Synthesis of 2-cyanomethylbiphenyl

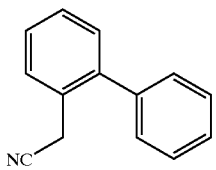

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), phenylboron dihydroxide (183 mg, 1.5 mmol), and potassium fluoride (174 mg, 3.0 mmol). The tube was evacuated and backfilled with argon, and THF (1 mL) and 2-chlorobenzyl cyanide (152 mg, 1.0 mmol) were added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL) and poured into a separatory funnel. The mixture was washed with 1.0 M NaOH (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 178 mg (92%) of the title compound.

EXAMPLE 31

Synthesis of 4-carbomethoxy-3'-acetylbiphenyl

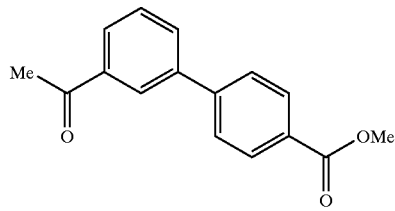

An oven dried resealable Schlenk tube was evacuated and backfilled with argon and charged with palladium acetate (2.2 mg, 0.01 mmol, 1.0 mol %), 2-di-tert-butylphosphino) biphenyl (6.0 mg, 0.020 mmol, 2.0 mol %), 3-acetylphenyl boronic acid (246 mg, 1.5 mmol), potassium fluoride (174 mg, 3.0 mmol), and methyl-4-chlorobenzoate (171 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 229 mg (90%) of the title compound.

EXAMPLE 32

Synthesis of 4-cyanobiphenyl

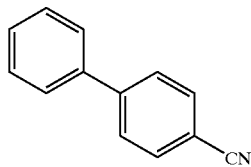

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), phenylboronic acid (183 mg, 1.5 mmol), potassium fluoride (174 mg, 3.0 mmol), and 4-chlorobenzonitrile (136 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 159 mg (89%) of the title compound.

EXAMPLE 33

Synthesis of 4-formyl-4'-ethoxybiphenyl

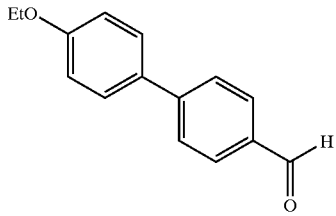

An oven dried resealable Schlenk tube was evacuated and backfilled with argon and charged with palladium acetate (1.1 mg, 0.005 mmol, 0.5 mol %), 2-(di-tert-butylphosphino)biphenyl (3.0 mg, 0.01 mmol, 1.0 mol %), 4-ethoxyphenylboronic acid (249 mg, 1.5 mmol), potassium fluoride (174 mg, 3.0 mmol), and 4-bromobenzaldehyde (185 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl bromide had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 203 mg (90%) of the title compound.

EXAMPLE 34

Synthesis of 4-hydroxybiphenyl

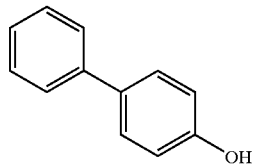

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.02 mmol, 2.0 mol %), phenylboronic acid (183 mg, 1.5 mmol), potassium fluoride (174 mg, 3.0 mmol), and 4-bromophenol (173 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl bromide had been completely consumed as judged by GC analysis. The reaction mixture was then diluted with ether (30 mL), filtered through celite, and concentrated. The crude material was purified by flash chromatography on silica gel to afford 154 mg (91%) of the title compound.

EXAMPLE 35

Synthesis of 2-hydroxymethylbiphenyl

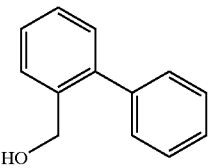

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.02 mmol, 2.0 mol %), phenylboronic acid (183 mg, 1.5 mmol), potassium fluoride (174 mg, 3.0 mmol), and 2-bromobenzyl alcohol (187 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl bromide had been completely consumed as judged by GC analysis. The reaction mixture was then diluted with ether (30 mL), filtered througth celite, and concentrated. The crude material was purified by flash chromatography on silica gel to afford 153 mg (83%) of the title compound.

EXAMPLE 36

Synthesis of 2,5-dimethylbiphenyl

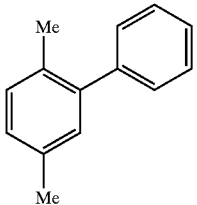

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.020 mmol, 2.0 mol %), phenylboronic acid (183 mg, 1.5 mmol), and potassium fluoride (174 mg, 3.0 mmol). The tube was evacuated and backfilled with argon, and THF (1 mL) and 2-bromo-p-xylene (0.138 mL, 1.0 mmol) were added through a rubber septum. The tube was sealed with a teflon screwcap, and the reaction mixture was stirred at room temperature until the starting aryl bromide had been completely consumed as judged by GC analysis. The reaction mixture was then diluted with ether (30 mL), filtered through celite, and concentrated. The crude material was purified by flash chromatography on silica gel to afford 149 mg (82%) of the title compound.

EXAMPLE 37

Synthesis of 4-methoxybiphenyl

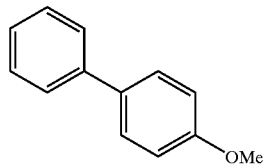

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.020 mmol, 2.0 mol %), phenylboronic acid (183 mg, 1.5 mmol), and potassium fluoride (174 mg, 3.0 mmol). The tube was evacuated and backfilled with argon, and THF (1 mL) and 4-chloroanisole (0.123 mL, 1.0 mmol) were added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL), filtered through celite, and concentrated. The crude material was purified by flash chromatography on silica gel to afford 176 mg (96%) of the title compound.

EXAMPLE 38

Synthesis of N-acetyl-4-aminobiphenyl

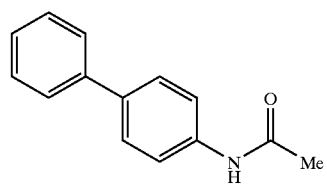

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.02 mmol, 2.0 mol %), phenylboronic acid (183 mg, 1.5 mmol), potassium fluoride (174 mg, 3.0 mmol), and 4'-bromoacetanilide (214 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl bromide had been completely consumed as judged by GC analysis. The reaction mixture was then diluted with ether (30 mL), filtered through celite, and concentrated. The crude material was purified by flash chromatography on silica gel to afford 182 mg (86%) of the title compound.

EXAMPLE 39

Synthesis of 4-nitrobiphenyl

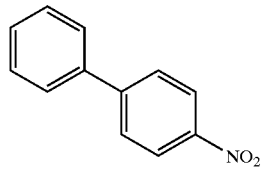

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.02 mmol, 2.0 mol %), phenylboronic acid (183 mg, 1.5 mmol), potassium fluoride (174 mg, 3.0 mmol), and 1-chloro-4-nitrobenzene (158 mg, 1.0 mmol). The tube was evacuated and backfilled with argon, and THF (1 mL) was added through a rubber septum. The tube was sealed with a teflon screwcap, and the reaction mixture was stirred at room temperature until the starting aryl chloride had been completely consumed as judged by GC analysis. The reaction mixture was then diluted with ether (30 mL), filtered through celite, and concentrated. The crude material was purified by flash chromatography on silica gel to afford 196 mg (98%) of the title compound.

EXAMPLE 40

Synthesis of 2,6-dimethylbiphenyl

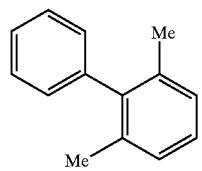

An oven dried resealable Schlenk tube was evacuated and backfilled with argon and charged with palladium acetate (2.2 mg, 0.01 mmol, 1.0 mol %), 2-(di-tert-butylphosphino)biphenyl (6.0 mg, 0.020 mmol, 2.0 mol %), phenylboronic acid (183 mg, 1.5 mmol), and potassium fluoride (174 mg, 3.0 mmol). The tube was evacuated and backfilled with argon, and THF (1 mL) and 2-bromo-m-xylene (0.144 mL, 1.0 mmol) were added through a rubber septum. The tube was sealed with a teflon screwcap, and the reaction mixture was stirred at 65° C. until the starting aryl bromide had been completely consumed as judged by GC analysis. The reaction mixture was then diluted with ether (30 mL), filtered through celite, and concentrated. The crude material was purified by flash chromatography on silica gel to afford 144 mg (79%) of the title compound.

EXAMPLE 41

Synthesis of 2-methoxy-4'-methylbiphenyl

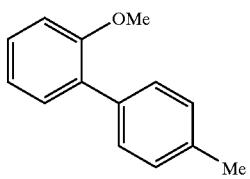

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), 2-methoxyphenylboronic acid (228 mg, 1.5 mmol), and potassium fluoride (174 mg, 3.0 mmol). The tube was evacuated and backfilled with argon, and THF (1 mL) and 4-chlorotoluene (0.144 mL, 1.0 mmol) were added through a rubber septum. The tube was sealed with a teflon screwcap, and the reaction mixture was stirred at 65° C. until the starting aryl chloride had been completely consumed as judged by GC analysis. The reaction mixture was then diluted with ether (30 mL), filtered through celite, and concentrated. The crude material was purified by flash chromatography on silica gel to afford 188 mg (95%) of the title compound.

EXAMPLE 42

Synthesis of 2-methoxy-2'-acetylbiphenyl

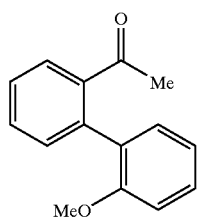

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), 2-methoxyphenylboronic acid (228 mg, 1.5 mmol), and potassium phosphate (425 mg, 2.0 mmol). The tube was evacuated and backfilled with argon, and toluene (3 mL) and 2'-chloroacetophenone (0.13 mL, 1.0 mmol) were added through a rubber septum. The tube was sealed with a teflon screwcap, and the reaction mixture was heated to 65° C. with stirring until the starting aryl chloride had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 201 mg (89%) of the title compound.

EXAMPLE 43

Synthesis of 3-(3-acetylphenyl)pyridine

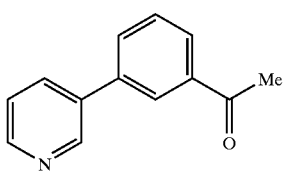

An oven dried resealable Schlenk tube was evacuated and backfilled with argon and charged with palladium acetate (2.2 mg, 0.01 mmol, 1.0 mol %), 2-(di-tert-butylphosphino) biphenyl (6.0 mg, 0.020 mmol, 2.0 mol %), 3-acetylphenylboronic acid (246 mg, 1.5 mmol), and potassium fluoride (173 mg, 3.0 mmol). The tube was evacuated and backfilled with argon, and THF (1 mL) and 3-chloropyridine (0.095 mL, 1.0 mmol) were added through a rubber septum. The tube was sealed with a teflon screwcap, and the reaction mixture was heated to 50° C. with stirring until the starting aryl chloride had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 181 mg (92%) of the title compound.

EXAMPLE 44

Synthesis of 4-acetylbiphenyl from an Aryl Chloride Utilizing 0.02 mol % Pd

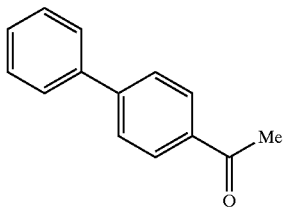

An oven dried resealable Schlenk tube was evacuated and backfilled with argon and charged with phenylboronic acid (228 mg, 1.5 mmol), and potassium phosphate (425 mg, 2.0 mmol). The tube was evacuated and backfilled with argon, and toluene (1.5 mL) and 4-chloroacetophenone (0.13 mL, 1.0 mmol) were added through a rubber septum. In a separate flask, palladium acetate (2.2 mg, 0.01 mmol) and 2-(di-tert-butylphosphino)biphenyl (6.0 mg, 0.02 mmol) were dissolved in 5 mL THF under argon. A portion of this solution (100 µL, 0.0002 mmol Pd, 0.02 mol % Pd) was added to the reaction mixture, followed by additional toluene (1.5 mL) through a rubber septum. The tube was sealed with a teflon screwcap, and the reaction mixture was heated to 100° C. with stirring until the starting aryl chloride had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magne-

EXAMPLE 45

Synthesis of 4-acetylbiphenyl from an Aryl Bromoide Utilizing 0.000001 mol % Pd

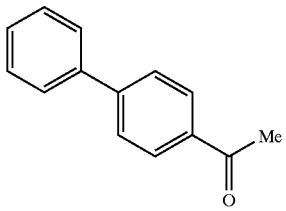

An oven dried resealable Schlenk tube was evacuated and backfilled with argon and charged with phenylboronic acid (228 mg, 1.5 mmol), and potassium phosphate (425 mg, 2.0 mmol), and 4-bromoacetophenone (199 mg, 1.0 mmol). The tube was evacuated and backfilled with argon, and toluene (1.5 mL) was added through a rubber septum. In a separate flask in a nitrogen filled glovebox, palladium acetate (4.5 mg, 0.02 mmol) and 2-(di-tert-butylphosphino)biphenyl (12.0 mg, 0.04 mmol) were dissolved in 20 mL THF under argon. A portion of this solution (10 µL, 0.00001 mmol Pd, 0.001 mol % Pd) was added to a second flask contaninig 10 mL THF). A portion of this second solution (10 µL, 0.00000001 mmol Pd, 0.000001 mol % Pd) was added to the reaction mixture, followed by additional toluene (1.5 mL) through a rubber septum. The tube was sealed with a teflon screwcap, and the reaction mixture was heated to 100° C. with stirring until the starting aryl bromide had been completely consumed as judged by GC analysis. The reaction mixture was then diluted with ether (30 mL) and poured into a separatory funnel. The mixture was washed with water (20 mL), and the aqueous layer was extracted with ether (20 mL). The combined organic layers were washed with brine (20 mL), dried over anhydrous magnesium sulfate, filtered, and concentrated. The crude material was purified by flash chromatography on silica gel to afford 176 mg (90 %) of the title compound.

EXAMPLE 46

Optimized Synthesis of 2-acetylbiphenyl Utilizing Potassium Fluoride

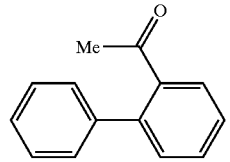

An oven dried Schlenk tube was evacuated and backfilled with argon and charged with palladium acetate (4.5 mg, 0.02 mmol, 1.0 mol %), 2-(di-tert-butylphosphino)biphenyl (11.9 mg, 0.040 mmol, 2.0 mol %), phenylboron dihydroxide (366 mg, 3.0 mmol), and potassium fluoride (349 mg, 6.0 mmol). The tube was evacuated and backfilled with argon, and THF (2 mL) and 2-chloroacetophenone (0.26 mL, 2.0 mmol) were added through a rubber septum. The reaction mixture was stirred at room temperature until the starting aryl chloride had been completely consumed as judged by GC analysis. The reaction mixture was then diluted with ethyl acetate (30 mL) and poured into a separatory funnel. The mixture was washed with 2.0M NaOH (20 mL). The organic layer was washed with brine (20 mL), dried over anhydrous sodium sulfate, filtered, and concentrated. The crude material was purified by flash chromatography on silica gel to afford 369 mg (94%) of the title compound.

EXAMPLE 47

Optimized Synthesis of 2-formyl-4'-diphenylketiminebiphenyl Utilizing Potassium Fluoride

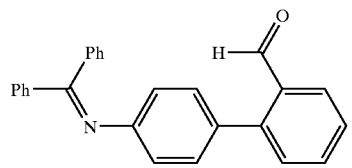

An oven dried Schlenk tube was evacuated and backfilled with argon and charged with palladium acetate (4.5 mg, 0.02 mmol, 1.0 mol %), 2-(di-tert-butylphosphino)biphenyl (11.9 mg, 0.040 mmol, 2.0 mol %), 4-diphenylketiminephenyl bromide (672 mg, 2.0 mmol), 2-formylphenylboron dihydroxide (450 mg, 3.0 mmol), and potassium fluoride (349 mg, 6.0 mmol). The tube was evacuated and backfilled with argon, and THF (2 mL) was added through a rubber septum. The reaction mixture was stirred at room temperature until the starting aryl bromide had been completely consumed as judged by GC analysis. The reaction mixture was then diluted with ethyl acetate (30 mL) and poured into a separatory funnel. The mixture was washed with 2.0M NaOH (20 mL). The organic layer was washed with brine (20 mL), dried over anhydrous sodium sulfate, filtered, and concentrated. The crude material was purified by flash chromatography on silica gel to afford 647 mg (90%) of the title compound.

EXAMPLE 48

Synthesis of 3-acetyl-3',5'-dimethoxybiphenyl

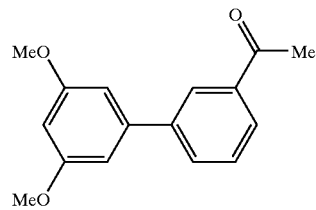

An oven dried Schlenk tube was evacuated and backfilled with argon and charged with palladium acetate (2.2 mg, 0.01 mmol, 1.0 mol %), 2-(di-tert-butylphosphino)biphenyl (6.0 mg, 0.020 mmol, 2.0 mol %), 3,5-dimethoxyphenyl chloride (173 mg, 1.0 mmol), 3-acetylphenylboron dihydroxide (246 mg, 1.5 mmol), and potassium fluoride (174 mg, 3.0 mmol). The tube was evacuated and backfilled with argon, and THF (1 mL) was added through a rubber septum. The reaction mixture was stirred at room temperature until the starting aryl chloride had been completely consumed as judged by GC analysis. The reaction mixture was then diluted with ethyl acetate (30 mL) and poured into a separatory funnel.

The mixture was washed with 2.0 M NaOH (20 mL). The organic layer was washed with brine (20 mL), dried over anhydrous magnesium sulfate, filtered, and concentrated. The crude material was purified by flash chromatography on silica gel to afford 232 mg (91%) of the title compound.

EXAMPLE 49

Synthesis of 2-phenylthiophene

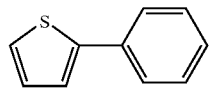

An oven dried Schlenk tube was evacuated and backfilled with argon and charged with palladium acetate (2.2 mg, 0.01 mmol, 1.0 mol %), 2-(di-tert-butylphosphino)biphenyl (6.0 mg, 0.020 mmol, 2.0 mol %), phenylboron dihydroxide (183 mg, 1.5 mmol), and potassium fluoride (174 mg, 3.0 mmol). The tube was evacuated and backfilled with argon, and THF (1 mL) and 2-bromothiophene ( 0.097 mL, 1.0 mmol) were added through a rubber septum. The reaction mixture was stirred at room temperature until the starting aryl bromide had been completely consumed as judged by GC analysis. The reaction mixture was then diluted with ethyl acetate (30 mL) and poured into a separatory funnel. The mixture was washed with 2.0M NaOH (20 mL). The organic layer was washed with brine (20 mL), dried over anhydrous magnesium sulfate, filtered, and concentrated. The crude material was purified by flash chromatography on silica gel to afford 159 mg (99%) of the title compound.

EXAMPLE 50

Room Temperature Synthesis of 4-methylbiphenyl Utilizing the Ligand 2,6-dimethoxyphenyl-di-t-butylphosphine An oven dried resealable Schlenk tube was evacuated and backfilled with argon and charged with palladium acetate (4.4 mg, 0.01 mmol, 1 mol %), 2,6-dimethoxyphenyl-di-t-butylphosphine (4.2 mg, 0.015 mmol, 1.5 mol %), phenylboron dihydroxide (183 mg, 1.5 mmol), and cesium fluoride (456 mg, 3.0 mmol). The tube was evacuated and backfilled with argon, and THF (3 mL) and 4-chlorotoluene (0.12 mL, 1.0 mmol) were added through a rubber septum. The septum was removed, the tube was sealed with a teflon screw cap and the mixture was stirred at room temperature until the starting aryl chloride had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 164 mg (98%) of a glassy solid.

EXAMPLE 51

Room Temperature Synthesis of 4-methylbiphenyl Utilizing the Ligand 2,4,6-trimethoxyphenyl-di-t-butylphosphine An oven dried resealable Schlenk tube was evacuated and backfilled with argon and charged with palladium acetate (4.4 mg, 0.01 mmol, 1 mol %), 2,4,6-trimethoxyphenyl-di-t-butylphosphine (4.7 mg, 0.015 mmol, 1.5 mol %), phenylboron dihydroxide (183 mg, 1.5 mmol), and cesium fluoride (456 mg, 3.0 mmol). The tube was evacuated and backfilled with argon, and THF (3 mL) and 4-chlorotoluene (0.12 mL, 1.0 mmol) were added through a rubber septum. The septum was removed, the tube was sealed with a teflon screw cap and the mixture was stirred at room temperature until the starting aryl chloride had been completely consumed as judged by GC analysis. The reaction mixture was then diluted with ether (20 mL) and poured into a separatory funnel. The mixture was washed with 1M NaOH (20 mL), and the layers were separated. The aqueous layer was extracted with ether (20 mL), and the combined organic extracts were dried over anhydrous magnesium sulfate, filtered, and concentrated in vacuo. The crude material was then purified by flash chromatography on silica gel to give 165 mg (98%) of a glassy solid.

EXAMPLE 52

Synthesis of 4-(trifluoromethyl)phenylboronic acid

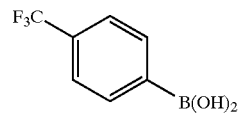

An oven dried Schlenk tube was charged with magnesium turnings (766 mg, 31.5 mmol), evacuated, and backfilled with argon. To the reaction vessel was added 10 mL of ether followed by 4-(trifluoromethyl)phenyl bromide (4.20 mL, 30.0 mmol). The reaction mixture was stirred without external heating for 1 hour, during which time an exotherm occurred and then subsided. The solution was diluted with ether (10 mL) and transferred via cannula to a flask containing triisopropylborate (13.8 mL, 60.0 mmol) in 1:1 THF/ether (20 mL) at −78° C. The resulting reaction mixture was kept at −78° C. for 15 minutes and then was allowed to warm to room temperature. After stirring at room temperature for 15 minutes, the reaction mixture was poured onto 2.0 M HCl (60 mL). The mixture was transferred to a separatory funnel, extracted with ethyl acetate (60 mL), washed with water (60 mL), and brine (60 mL). The organic solution was dried over anhydrous sodium sulfate and concentrated in vacuo. The crude material was dissolved in 2:1 hexane/ethyl acetate (90 mL) and activated charcoal was added. The mixture was filtered and the product crystallized upon cooling. The crystals were collected by filtration to afford 1.98 g (35%) of pale yellow needles.

EXAMPLE 53

Synthesis of 2-bromo-4'-(trifluoromethyl)biphenyl

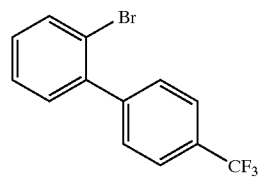

An oven dried Schlenk tube was evacuated and backfilled with argon and charged with tetrakis(triphenylphosphine)palladium (289 mg, 0.25 mmol, 5.0 mol %), 2-bromoiodobenzene (0.83 mL, 6.50 mmol), 4-(trifluoromethyl)phenylboronic acid (950 mg, 5.0 mmol), and sodium carbonate (2.86 g, 27.0 mmol). The tube was evacuated and backfilled with argon. To the tube was added (degassed) dimethoxyethane (45 mL), ethanol (2 mL), and water (15 mL) through a rubber septum. The reaction mixture was heated to 85° C. with stirring for 32 hours. The reaction mixture was then diluted with 2:1 hexane/ethyl acetate (100 mL) and poured into a separatory funnel. The mixture was washed with water (80 mL), and brine (80 mL). The organic layer was dried over anhydrous sodium sulfate, decanted, and concentrated in vacuo. The crude material was purified by flash chromatography on silica gel to afford 1.01 g (67%) of the product.

EXAMPLE 54

Synthesis of 2-(di-t-butylphosphino)-4'-(trifluoromethyl)biphenyl

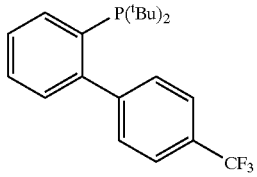

An oven dried Schlenk tube was evacuated and backfilled with argon and charged with magnesium turnings (90 mg, 3.69 mmol), 2-bromo-4'-(trifluoromethyl)biphenyl (1.01 g, 3.35 mmol), and a crystal of iodine. The tube was purged with argon for 5 minutes, then THF (6 mL) was added through a rubber septum and the reaction mixture was heated to reflux for 1 hour. The reaction mixture was cooled to room temperature and cuprous chloride (365 mg, 3.69 mmol) and chloro-di-t-butylphosphine (0.765 mL, 4.03 mmol) were added. Heating was resumed for 14 hours. The reaction mixture was then cooled to room temperature and diluted with ether (40 mL). The suspension was filtered to isolate the solid. The solid was partitioned between ethyl acetate (60 mL) and 38% ammonium hydroxide (75 mL). The aqueous layer was extracted with ethyl acetate (60 mL). The combined organic layers were washed with brine (50 mL), dried over anhydrous sodium sulfate, decanted, and concentrated in vacuo. The product was crystallized from MeOH (10 mL) to afford 131 mg (11%) of pale yellow needles. A second crop was isolated by concentrating the mother liquor and recrystallizing the solid from MeOH (20 mL) and water (2 mL) to afford 260 mg (21 %) of the product.

EXAMPLE 55

Synthesis of 2-(di-1-adamantylphosphino)biphenyl

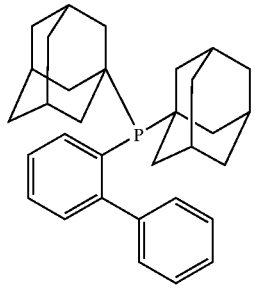

An oven-dried, round-bottom flask was charged with magnesium turnings (15.3 g, 0.63 mol) and 1-bromoadamantane (9.0 g, 0.041 mol). The flask was evacuated and backfilled with argon two times. To the reaction vessel 45 mL ether was added and the mixture was gently refluxed for 15 hours, without mechanical stirring. The resulting solution of Grignard reagent was taken up in a syringe, and added very slowly dropwise to a separate flame-dried, two-necked, round-bottom flask equipped with a reflux condenser which had been charged with $PCl_3$ (0.9 mL, 10 mmol) and 15 mL ether which had been coooled to −40° C. During the addition the temperature was monitored and kept below −25° C. The resulting mixture was stirred for 30 minutes at −45° C., then the cooling bath was removed and the reaction mixture was allowed to warm slowly to room temperature. After stirring for an additional 30 minutes at room temperature, the reaction vessel was placed into a heated oilbath (37° C.) and was gently refluxed for 22 hours. The mixture was cooled to room temperature, and the solution was filtered through a cannula filter. The solvent as well as some of the adamantane byproduct was removed in vacuo, without exposing the product to air to afford crude di-1-adamantylchlorophosphine.

An oven dried Schlenk tube was charged with magnesium turnings (240 mg, 9.89 mmol), 2-bromo-biphenyl (1.55 mL, 7.5 mmol). The tube was evacuated and backfilled with argon two times. To the above mixture THF (15 mL) was added through a rubber septum and the reaction mixture was heated to a mild reflux for 3 hours. The reaction mixture was then temporarily cooled to room temperature for the addition of cuprous chloride (930 mg, 9.45 mmol) followed by a solution of the di-l-adamantylchlorophosphine in 5 mL THF. Heating was resumed for an addtional 3 hours. The reaction mixture was cooled to room temperature, and ether (50 mL) and pentane (50 mL) were added. The resulting suspension was stirred for 10 minutes, during which time a heavy dark-brown precipitate formed. The suspension was filtered and the solid was collected on a fritted funnel. The solid was partitioned between ethyl acetate-ether (100 mL 1:1) and 38% ammonium hydroxide-water (100 mL 1:1). The mixture was vigorously shaken several times over 30 minutes. The aqueos layer washed twice with ether-ethyl acetate (1:1, 100 mL). The combined organic layers were washed with brine (2×50 mL), dried over anhydrous magnesium sulfate, decanted, and concentrated in vacuo. The product was crystallized from toluene/methanol to afford 450 mg (5.8%) product as a white solid.

EXAMPLE 56

Synthesis of 2-(di-t-butylphosphino)-2'-(isopropyl)biphenyl

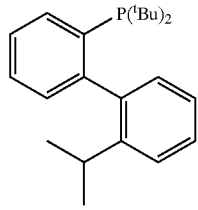

A flame-dried Schlenk tube was evacuated and backfilled with argon two times, and was charged with 2-(bromo)-2'-(isopropyl)biphenyl (1.5 g, 5.45 mmol) and ether (15 mL) The reaction mixture was cooled to −78° C., and t-BuLi (6.7 mL, 1.7 M in penate) was added dropwize via a syringe, through a rubber septum. After the addition was complete, the reaction mixture was stirred for an additional 15 minutes at −78° C. The cooling bath was removed, and t-Bu$_2$PCl was added dropwise. After reaching room temperature, the reaction vessel was placed into a heated oil bath (37° C.), and the reaction mixture was refluxed for 48 hours. The mixture was cooled to room temperature, a saturated solution of aqueous ammonium chloride (10 mL) was added, and the resulting mixture was partitioned between ether (100 mL) and water (50 mL). The organic layer was dried over a 1:1 mixture of anhydrous magnesium sulfate and sodium sulfate, decanted and concentrated in vacuo. The product was crystallized from MeOH to afford 601 mg (30%) of white needles.

EXAMPLE 57

Synthesis of di-tbutyl-(o-cyclohexyl)phenyl phosphine (3)

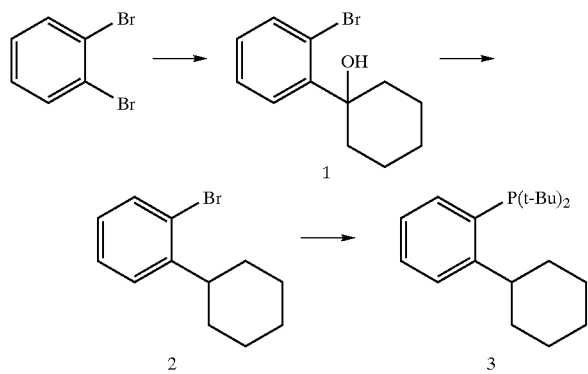

An oven-dried Schlenk flask was allowed to cool to room temperature under an argon purge, and was charged with 1,2-dibromobenzene (1.2 mL, 10.0 mmol), ether (20 mL), and THF (20 mL). The mixture was cooled to −119° C. with stirring using an ethanol/N$_2$ cold bath. n-butyllithium in hexanes (5.8 mL, 1.6 M, 9.3 mmol) was added slowly dropwise. The mixture was stirred at −119° C. for 45 min, then cyclohexanone (0.98 mL, 9.5 mmol) was added to the mixture. The mixture was stirred at −78° C. for 30 min, then warmed to room temperature and stirred for 17 h. The mixture was quenched with saturated aqueous ammonium chloride (20 mL), diluted with ether (50 mL), and poured into a separatory funnel. The layers were separated and the aqueous phase was extracted with ether (1×20 mL). The organic layers were combined and washed with brine (20 mL), dried over anhydrous magnesium sulfate, filtered, and concentrated in vacuo. The crude material was purified by flash chromatography on silica gel to afford 1.91 g of 1 which was judged to be ~86% pure by GC analysis. This material was used without further purification.

A round bottomed flask was purged with argon and charged with alcohol 1 (1.78 g, 7.0 mmol), dichloromethane (28 mL), triethylsilane (1.5 mL, 9.1 mmol), and trifluoroacetic acid (1.1 mL, 14.7 mmol). The mixture was stirred at room temperature for 1.5 h, then was quenched with solid potassium carbonate (ca 2 g). The mixture was diluted with ether (50 mL) and transferred to a separatory funnel. The mixture was washed with saturated aqueous NaHCO$_3$ (50 mL), and the organic phase was dried over anhydrous magnesium sulfate, filtered, and concentrated in vacuo to afford a mixture of 2 and 1-(2-bromophenyl)cyclohexene. The crude material was placed into a round bottomed flask, and the flask was purged with argon. THF (2 mL) was added, and the mixture was cooled to 0° C. with stirring. A solution of BH$_3$ in THF (7 mL, 1M, 7.0 mmol) was added dropwise to the mixture. The mixture was stirred at 0° C. for 1.5 h, then warmed to room temperature and stirred for 19 h. Acetic acid (4 mL) was added and the mixture was stirred at room temperature for 6h. The mixture was then diluted with ether (50 mL) and poured into a separatory funnel. The mixture was washed with 1M NaOH (50 mL), the layers were separated, and the aqueous phase was extracted with ether (50 mL). The combined organic phases were washed with brine (50 mL), dried over anhydrous magnesium sulfate, filtered, and concentrated in vacuo. The crude material was purified by flash chromatography on silica gel to afford 555 mg of 2 which was judged to be 93% pure by GC analysis. This material was used without further purification.

An oven-dried Schlenk tube was cooled to room temperature under an argon purge, and was charged with magnesium turnings (27 mg, 1.1 mmol), THF (1 mL), and 1,2-dibromoethane (8 μL). The mixture was stirred at room temperature for 10 min, then 2 (239 mg, 1.0 mmol) was added in one portion. The mixture was stirred at rt for 20 min, then heated to 60° C. for 15 min. The mixture was cooled to room temperature, the septum was removed from the flask, and copper (I) chloride (104 mg, 1.05 mmol) was added. The tube was capped with the septum and purged with argon for 1 min. The tube was charged with di-t-butylchlorophosphine (23 mL, 1.2 mmol) and additional THF (1 mL). The mixture was heated to 60° C. with stirring for 26 h. The mixture was cooled to room temperature and filtered, and the solids were washed with ether/hexanes (50 mL, 1/1 v/v). The organic solution was poured into a separatory funnel and washed with ammonium hydroxide solution (3×50 mL), and brine (50 mL). The organic phase was then dried over anhydrous sodium sulfate, filtered, and concentrated. The crude material was purified by flash chromatography on silica gel to afford 3 as a white solid (141 mg), which was judged to be 92% pure by GC analysis. This material was recrystallized from hot methanol to afford 101 mg (~3% overall from 1,2-dibromobenzene) of 3 as a white, crystalline solid.

EXAMPLE 58

Preparation of o-di-t-butylphosphino-o-terphenyl (3)

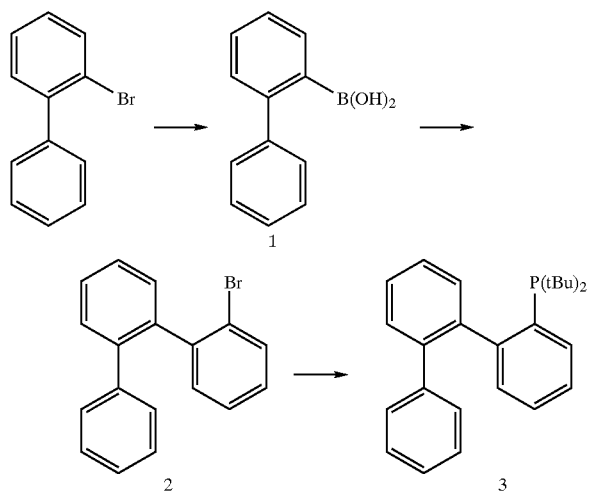

An oven-dried Schlenk tube was cooled to room temperature under an argon purge, and was charged with magnesium turnings (243 mg, 11.0 mmol), ether (7 mL), and 1,2-dibromoethane (38 µL). The mixture was stirred at room temperature until the evolution of gases ceased, then a solution of 2-bromobiphenyl (1.7 mL, 10.0 mmol) in 5 mL ether was added dropwise. The mixture was stirred at room temperature for 1.75 h. The solution was then transferred to a separate flask containing a solution of triisopropyl borate (4.6 mL, 20.0 mmol) in THF (20 mL) which had been cooled to 0° C. The mixture was stirred at 0° C. for 15 min, then warmed to room temperature and stirred for 21 h. The reaction was quenched with 1M HCl (40 mL) and stirred at room temperature for 10 min. The solution was basisified to pH 14 with 6M NaOH, then extracted with ether (1×10 mL). The organic phase was discarded and the aqueous phase was acidified to pH 2 with 6M HCl. The aqueous phase was extracted with ether (3×50 mL), and the combined organic layers were dried over anhydrous sodium sulfate, filtered, and concentrated in vacuo. The crude material was recrystallized from ether/pentane at −20° C. to afford 1.0 g (51%) of 1 as a white, crystalline solid.

An oven-dried Schlenk flask was cooled to room temperature under an argon purge, and was charged with tetrakis(triphenylphosphine)palladium (289 mg, 0.25 mmol, 5 mol %) sodium carbonate (2.86 g, 27 mmol), and 1 (1.0 g, 5.0 mmol). The flask was purged with argon and DME (50 mL), ethanol (2 mL), water (15 mL), and 2-bromoiodobenzene (0.83 mL, 6.05 mmol) were added through a rubber septem. The mixture was heated to 85° C. with stirring for 3 days. The mixture was cooled to room temperature, diluted with ether (100 mL), and poured into a separatory funnel. The layers were separated and the organic phase was washed with 1M NaOH (2×50 mL), washed with brine, dried over anhydrous magnesium sulfate, filtered, and concentrated in vacuo. The crude material was purified by flash chromatography on silica gel to afford 1.23 g (79%) of 2 as a colorless oil.

An oven-dried Schlenk tube was cooled to room temperature under an argon purge, and was charged with magnesium turnings (54 mg, 2.2 mmol), THF (2 mL), and 1,2-dibromoethane (9 µL). The mixture was stirred at room temperature for 15 min, then a solution of 2 (618 mg, 2.0 mmol) in 1 mL THF was added dropwise. The mixture was stirred at rt for 1 h, then the septum was removed from the flask, and copper (I) chloride (283 mg, 2.1 mmol) was added. The tube was capped with the septum and purged with argon for 1 min. The tube was charged with di-t-butylchlorophosphine (0.46 mL, 2.4 mmol) and additional THF (1 mL). The mixture was heated to 60° C. with stirring for 26 h. The mixture was cooled to room temperature and filtered, and the solids were washed with ether/hexanes (50 mL, 1/1 v/v). The organic solution was poured into a separatory funnel and washed with ammonium hydroxide solution (3×5 mL), and brine (50 mL) The organic phase was then dried over anhydrous sodium sulfate, filtered, and concentrated. The crude material was recrystallized from hot methanol to afford 191 mg (26%) of 3 as a white, crystalline solid.

All publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for forming a compound represented by Ar—Ar', comprising the step of:

combining a compound represented by ArX, a compound represented by Ax'B(OH)$_2$, a transition metal, a ligand and a base; wherein Ar and Ar' are independently selected from the group consisting of optionally substituted monocyclic and polycyclic aromatic and heteroaromatic moieties;

X is selected from the group consisting of Cl, Br, I, —OS(O)$_2$alkyl, and —OS(O)$_2$aryl;

the transition metal is selected from the group consisting of the Group VIIIA metals;

the ligand is selected from the group consisting of a compound represented by 2:

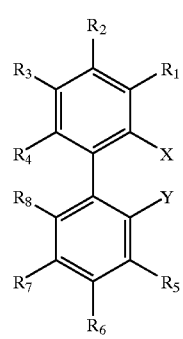

wherein

Q represent P(R)$_2$;

Y represents H, alkyl, N(R)$_2$, OR, or SR;

R, R$_1$, R$_2$, R$_3$, R$_4$, R$_5$, R$_6$, R$_7$, and R$_8$, independently for each occurrence represent hydrogen, halogen, alkyl, alkenyl, alkynyl, hydroxyl, alkoxyl, silyloxy, amino, nitro, sulfhydryl, alkylthio, imino, carboxamido, phosphoryl, phosphonate, phosphine, carbonyl, carboxyl, silyl, thioalkyl, alkylsulfonyl, alrylsulfonyl, selenoalkyl, formyl, acyl, aldehyde, ester, heteroalkyl, nitrile, guanidine, amidine, acetal, ketal, amine oxide, aryl, heteroaryl, azide, aziridine, carbamate, epoxide, hydroxamic acid, imide, oxime, sulfonamide, thioamide, thiocarbamate, urea, thiourea, or —$(CH_2)_m$—$R_{80}$;

$R_{80}$ represents independently for each occurrence an unsubstituted or substituted aryl, a cycloalkyl, a cycloalkenyl, a heterocycle, or a polycycle;

m is independently for each occurrence an integer in the range 0 to 8 inclusive; and the ligand, when chiral, may be provided in the form of a mixture of enantiomers or as a single enantiomer; and the base is selected from the group consisting of carbonates, phosphates, fluorides, alkoxides, amides, carbanions, and silyl anions.

2. The method of claim 1, wherein the transition metal is palladium; and the base is an alkoxide, amide, fluoride, phosphate, or carbonate.

3. The method of claim 1 or 2 wherein

Y is hydrogen, and Q represents $P(alkyl)_2$; and

X represents Cl or Br.

4. The method of claim 1, wherein:

the transition metal is palladium;

Q represents $P(alkyl)_2$; Y represents H or $N(alkyl)_2$; and the base is an alkoxide, amide, carbonate, or fluoride.

5. The method of claim 4, wherein:

X represents Cl or Br; and the reaction occurs at room temperature.

6. The method of claim 1, wherein $R_1$, $R_2$, $R_3$, $R_4$, $R_5$, $R_6$, $R_7$, and $R_8$ represent hydrogen; Q represents $P(t-Bu)_2$ or $PCy_2$; Y represents H or $NMe_2$; the transition metal is palladium; and the base is cesium fluoride or potassium fluoride.

7. The method of claim 1, wherein the product is provided in a yield of greater than 50%.

8. The method of claim 1, wherein the product is provided in a yield of greater than 70%.

9. The method of claim 1, wherein the product is provided in a yield of greater than 85%.

10. The method of claim 1, wherein the reaction occurs at ambient temperature.

11. The method of claim 1, wherein the transition metal and the ligand are independently present in less than 0.01 mol % relative to the limiting reagent.

12. The method of claim 1, wherein the transition metal and the ligand are independently present in less than 0.0001 mol % relative to the limiting reagent.

13. The method of claim 1, wherein X is chloride.

14. The method of claim 1, wherein the limiting reagent is consumed in less than 48 hours.

15. The method of claim 1, wherein the limiting reagent is consumed in less than 24 hours.

16. The method of claim 1, wherein the limiting reagent is consumed in less than 12 hours.

17. The method of claim 1, wherein the yield of the product is greater than 50% in less than 48 hours.

18. The method of claim 1, wherein the yield of the product is greater than 50% in less than 24 hours.

19. The method of claim 1, wherein the yield of the product is greater than 50% in less than 12 hours.

* * * * *

UNITED STATES PATENT AND TRADEMARK OFFICE
CERTIFICATE OF CORRECTION

PATENT NO. : 6,946,560 B2  
APPLICATION NO. : 10/420950  
DATED : September 20, 2005  
INVENTOR(S) : Stephen L. Buchwald et al.

Page 1 of 1

It is certified that error appears in the above-identified patent and that said Letters Patent is hereby corrected as shown below:

In the Claims

In claim 1, at column 88, line 45, the structure " 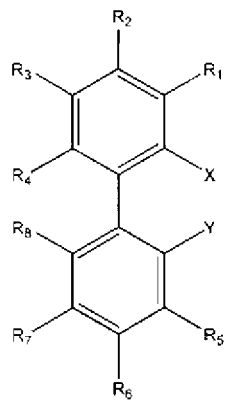 " should be replaced with the structure -- 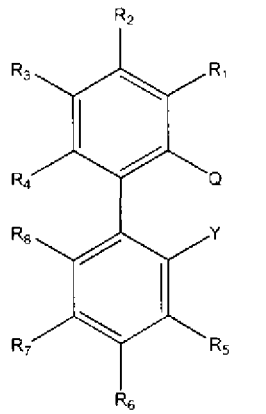 --.

Signed and Sealed this  
Twenty-fifth Day of August, 2015

Michelle K. Lee  
*Director of the United States Patent and Trademark Office*